United States Patent
Lee et al.

(10) Patent No.: US 10,590,423 B2
(45) Date of Patent: *Mar. 17, 2020

(54) TREATMENT OF AGE-RELATED MACULAR DEGENERATION USING RNA COMPLEXES THAT TARGET MYD88 OR TLR3

(71) Applicant: OliX Pharmaceuticals, Inc., Suwon-Si (KR)

(72) Inventors: Dong-ki Lee, Seoul (KR); Sun Woo Hong, Seoul (KR); Isu Hong, Seoul (KR); Jihye Hwang, Geonggi-Do (KR)

(73) Assignee: OliX Pharmaceuticals, Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,833

(22) Filed: Jul. 23, 2018

(65) Prior Publication Data

US 2018/0327755 A1 Nov. 15, 2018

Related U.S. Application Data

(62) Division of application No. 15/352,322, filed on Nov. 15, 2016, now Pat. No. 10,059,949.

(60) Provisional application No. 62/255,878, filed on Nov. 16, 2015.

(51) Int. Cl.
C12N 15/113 (2010.01)

(52) U.S. Cl.
CPC ........ *C12N 15/1138* (2013.01); *C12N 15/113* (2013.01); *C12N 2310/14* (2013.01); *C12N 2310/315* (2013.01); *C12N 2310/321* (2013.01); *C12N 2320/32* (2013.01)

(58) Field of Classification Search
CPC combination set(s) only.
See application file for complete search history.

(56) References Cited

U.S. PATENT DOCUMENTS

| | | | |
|---|---|---|---|
| 5,837,258 A | 11/1998 | Grotendorst | |
| 7,078,196 B2 | 7/2006 | Tuschl et al. | |
| 7,691,997 B2 | 4/2010 | Khvorova et al. | |
| 7,700,541 B2 | 4/2010 | Tanaka et al. | |
| 8,410,260 B2 | 4/2013 | Collin-Djangone et al. | |
| 8,614,309 B2 | 12/2013 | Feinstein et al. | |
| 8,802,733 B2 | 8/2014 | Ganesan et al. | |
| 8,822,428 B2 | 9/2014 | Collin-Djangone et al. | |
| 8,980,273 B1 | 3/2015 | Clube | |
| 9,453,226 B2 | 9/2016 | Ambati et al. | |
| 9,637,742 B2 | 5/2017 | Lee | |
| 9,707,235 B1 | 7/2017 | Ambati | |
| 10,059,949 B2 | 8/2018 | Lee et al. | |
| 10,064,801 B2 | 9/2018 | Hong et al. | |
| 10,125,362 B2 | 11/2018 | Hong | |
| 10,214,744 B2 | 2/2019 | Lee | |
| 10,358,648 B2 | 7/2019 | Lee et al. | |
| 2004/0138163 A1 | 7/2004 | McSwiggen et al. |
| 2004/0180351 A1 | 9/2004 | Giese et al. |
| 2004/0266707 A1 | 12/2004 | Leake et al. |
| 2005/0119202 A1 | 6/2005 | Kreutzer et al. |
| 2005/0282188 A1 | 12/2005 | Haeberli et al. |
| 2006/0069050 A1 | 3/2006 | Rana |
| 2006/0094032 A1 | 5/2006 | Fougerolles et al. |
| 2006/0105976 A1 | 5/2006 | Soutschek et al. |
| 2006/0134787 A1 | 6/2006 | Zamore et al. |
| 2006/0142228 A1 | 6/2006 | Ford et al. |
| 2006/0160123 A1 | 7/2006 | Quay |
| 2007/0218495 A1 | 9/2007 | Birmingham et al. |
| 2007/0275914 A1 | 11/2007 | Manoharan et al. |
| 2008/0125386 A1 | 5/2008 | Rana et al. |
| 2008/0188430 A1 | 8/2008 | Usman et al. |
| 2009/0004668 A1 | 1/2009 | Chen et al. |
| 2009/0012022 A1 | 1/2009 | Milner et al. |
| 2009/0130751 A1 | 5/2009 | Davidson et al. |
| 2009/0191625 A1 | 7/2009 | Khvorova et al. |
| 2009/0208564 A1 | 8/2009 | Li et al. |
| 2010/0197023 A1 | 8/2010 | Leake et al. |
| 2010/0254945 A1 | 10/2010 | Ge et al. |
| 2010/0291681 A1 | 11/2010 | Khvorova et al. |
| 2011/0028534 A1 | 2/2011 | Shepard et al. |
| 2011/0054160 A1 | 3/2011 | Manoharan |
| 2011/0237647 A1 | 9/2011 | Shirasawa et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |

(Continued)

FOREIGN PATENT DOCUMENTS

| CN | 102719432 | 10/2012 |
|---|---|---|
| EP | 2631291 | 8/2013 |

(Continued)

OTHER PUBLICATIONS

Ambati et al., "Mechanisms of Age-Related Macular Degeneration," Neuron, 75: 26-39 (2012).
Bolcato-Bellemin et al., "Sticky overhangs enhance siRNA-mediated gene silencing," PNAS, vol. 104, No. 41, pp. 16050-16055 (2007).
Bramsen et al., "Improved silencing properties using small internally segmented interfering RNAs," Nucleic Acids Research, (2007), 35:5886-5897.
Bushati et al., "MicroRNAs in Neurodegeneration," Current Opin Neurobiol, 18: 292-296 (2008).
Caplen et al., "Specific inhibition of gene expression by small double-stranded RNAs in invertebrate and vertebrate systems," Proc. Natl. Acad. Sci. USA, (2001), pp. 9742-9747, vol. 98, No. 17.

(Continued)

*Primary Examiner* — Jennifer Pitrak McDonald
(74) *Attorney, Agent, or Firm* — Morgan, Lewis & Bockius LLP

(57) ABSTRACT

In certain aspects, provided herein are RNA complexes that inhibit Myeloid differentiation primary response gene 88 (MyD88) and/or Toll-like receptor 3 (TLR3) and are useful in the treatment of age-related macular degeneration (AMD). In certain aspects, provided herein are pharmaceutical compositions comprising such RNA complexes and methods of using such RNA complexes and pharmaceutical compositions.

19 Claims, 20 Drawing Sheets

Specification includes a Sequence Listing.

(56) References Cited

U.S. PATENT DOCUMENTS

| | | | |
|---|---|---|---|
| 2011/0269816 | A1 | 11/2011 | Kaspar et al. |
| 2012/0016011 | A1 | 1/2012 | Pickering et al. |
| 2012/0238017 | A1 | 9/2012 | Lee et al. |
| 2013/0011922 | A1 | 1/2013 | Quay et al. |
| 2013/0035368 | A1 | 2/2013 | Avkin-Nachum et al. |
| 2013/0115613 | A1 | 5/2013 | Madiraiu et al. |
| 2013/0123342 | A1 | 5/2013 | Brown |
| 2013/0131142 | A1 | 5/2013 | Libertine et al. |
| 2013/0190387 | A1 | 7/2013 | Feinstein |
| 2013/0273657 | A1 | 10/2013 | Lee |
| 2013/0317080 | A1 | 11/2013 | Rajeev et al. |
| 2014/0094501 | A1 | 4/2014 | Puri et al. |
| 2014/0227266 | A1 | 8/2014 | Lee et al. |
| 2014/0249304 | A1 | 9/2014 | Lee et al. |
| 2014/0328903 | A1 | 11/2014 | Santel et al. |
| 2014/0350068 | A1 | 11/2014 | Feinstein et al. |
| 2015/0111948 | A1 | 4/2015 | Hong |
| 2015/0184163 | A1 | 7/2015 | Wilson et al. |
| 2016/0017056 | A1 | 1/2016 | Clube |
| 2016/0122764 | A1 | 5/2016 | Chae et al. |
| 2016/0319278 | A1 | 11/2016 | Khvorova et al. |
| 2017/0298358 | A1 | 10/2017 | Lee et al. |
| 2017/0369882 | A1 | 12/2017 | Khvorova et al. |

FOREIGN PATENT DOCUMENTS

| | | |
|---|---|---|
| JP | 2012502991 | 2/2012 |
| KR | 101207561 | 12/2012 |
| WO | WO0244321 | 6/2002 |
| WO | WO02055693 | 7/2002 |
| WO | WO2005062937 | 7/2005 |
| WO | WO2005079533 | 9/2005 |
| WO | WO2007002470 | 2/2007 |
| WO | WO2007128477 | 11/2007 |
| WO | WO2008109377 | 9/2008 |
| WO | WO2009020344 | 2/2009 |
| WO | WO2009029688 | 3/2009 |
| WO | WO2009029690 | 3/2009 |
| WO | WO2009078685 | 6/2009 |
| WO | WO2009105260 | 8/2009 |
| WO | WO 2010/017436 A2 | 2/2010 |
| WO | WO2010033247 | 3/2010 |
| WO | WO2010090762 | 8/2010 |
| WO | WO201119887 | 9/2011 |
| WO | WO2012078536 | 6/2012 |
| WO | WO2012118911 | 9/2012 |
| WO | WO2014043291 | 3/2014 |
| WO | WO2015002513 | 1/2015 |
| WO | WO2015015498 | 2/2015 |
| WO | WO2015171641 | 11/2015 |
| WO | WO2017017523 | 2/2017 |
| WO | WO2017085550 | 5/2017 |
| WO | WO2017134525 | 8/2017 |
| WO | WO2017134526 | 8/2017 |
| WO | WO2017178883 | 8/2017 |
| WO | WO2018004284 | 1/2018 |
| WO | WO2018146557 | 8/2018 |

OTHER PUBLICATIONS

Chang et al., "Structural diversity repertoire of gene silencing small interfering RNAs," Nucleic acid therapeutics, (2011), 21(3), 125-131.

Chang et al., "The design, preparation, and evaluation of asymmetric small interfering RNA for specific gene silencing in mammalian cells," Methods Mol Biol. 2013; 942:135-52.

Chang et al., "Asymmetric shorter-duplex siRNA structures trigger efficient gene silencing with reduced nonsoecific effects," Mol Ther, (2009), 7(4): 725-732.

Chiu et al., "siRNA Function in RNAi: A Chemical Modification Analysis," RNA, 9: 1034-1048 (2003).

Doench et al., "siRNAs Can Function as miRNAs," Gene Dev, 17(4): 438-442 (2003).

Doench et al., "Specificity of MicroRNA Target Selection in Translation Repression," Gene Dev, 18: 504-511 (2004).

Elbashir et al., "Duplexes of 21-nucleotide RNAs mediate RNA interference in cultured mammalian cells," Nature, (2001), 411:494-498.

Elbashir et al., "Functional anatomy of siRNAs for mediating efficient RNAi in *Drosophila melanogaster* embryo lysate," The EMBO Journal, (2001), pp. 6877-6888, vol. 20, No. 23.

Fire, "RNA-triggered gene silencing," Trends in Genetics, (1999), vol. 15, No. 9, pp. 358-363.

Fire et al., "Potent and specific genetic interference by double-stranded RNA in Caenorhabditis elegans," Nature, (1998), pp. 806-811, vol. 391.

Grimm, "Small silencing RNAs: State of the art," Advanced Drug Delivery Reviews, 61: 672-703 (2009).

Hammond et al., "Post-Transcriptional Gene Silencing by Double-Stranded RNA," Nature Reviews Genetics, (2001), vol. 2: 110-119.

Hong et al., "Effect of the guide strand 3'-end structure on the gene-silencing potency of asymmetric siRNA," Biochemical Journal, (2014), 461(3): 427-434.

Huang et al., "Targeting the ANGPT-TIE2 Pathway in Malignancy," Nat Rev Cancer, 10: 575-585 (2010).

Hwang, "Development of Cell-Penetrating Asymmetric Interfering RNA Targeting Connective Tissue Growth Factor," Journal of Investigative Dermatology, (2016), 136(11), 2305-2313.

Jackson et al., "Expression Profiling Reveals Off-Target Gene Regulation by RNAi," Nat Biotechnol, 21: 635-637 (2003).

Jang et al., "Gene Delivery From Polymer Scaffolds for Tissue Engineering," Expert Rev Med Devic, 1(1): 127-138 (2004).

Jeong et al., "siRNA conjugate delivery systems," Bioconjugate Chem, 20:5-14 (2009).

Jo et al., "Selection and optimization of asymmetric siRNA targeting the human c-MET gene," Mol Cell, 32:(6) 543-548 (2011).

Joshi et al., "siRNA: novel therapeutics from functional genomics," Biotechnology and Genetic Enginnering Reviews (2014) vol. 30, No. 1, pp. 1-30.

Kelly et al., "Cell Type-Specific Regulation of Angiogenic Growth Factor Gene Expression and Induction of Angiogenesis in Nonischemic Tissue by a Constitutively Active Form of Hypoxia-inducible Factor 1," Circ Res, 93: 1074-1081 (2003).

Kim et al., "Synthetic dsRNA Dicer substrates enhance RNAi potency and efficacy," Nature Biotechnology, 23: 222-226 (2005).

Kore et al., "Chemical modification of synthetic RNAi agents and in vivo delivery techniques," Curr Bioactive Compounds, 4:6-14 (2008).

Kubo et al., "Modified 27nt dsRNAs with Dramatically Enhanced Stability in Serum and Long-Term RNAi Activity," Oligonucleotides, 17:445-464 (2007).

Kulkarni et al., "Evidence of Off-Target Effects Associated with Long dsRNAs in *Drosophila melanogaster* Cell-Based Assays," Nat Methods, 3: 833-838 (2006).

Lee et al., "Asymmetric RNA Duplexes as Next Generation RNAi Inducers," Gene Silencing: Theory, Techniques and Applications, (2010), pp. 343-348.

Li et al., "Inhibition of connective tissue growth factor by siRNA prevents liver fibrosis in rats," The Journal of Gene Medicine, (2006), 8:889-900.

Lima et al., "Human Dicer Binds Short Single-strand and Double-strand RNA with High Affinity and Interacts with Different Regions of the Nucleic Acids," The Journal of Biological Chemistry (2009), 284:2535-2548.

Luo et al., "Inhibition of Connective Tissue Growth Factor by Small Interfering RNA Prevents Renal Fibrosis in Rats Undergoing Chronic Allograft Nephropathy," Transplantation Proceedings, (2008), 40:2365-2369.

Marques et al., "A structural basis for discriminating between self and nonself double-stranded RNAs in mammalian cells," Nature Biotechnology, 24: 559-565 (2006).

Martinez et al., "Singe-Stranded Antisense siRNAs Guide Target RNA Cleavage in RNAi," Cell, 110: 563-574 (2002).

Opalinska et al., "Nucleic-acid Therapeutics: Basic Principles and Recent Applications," Nature Rev, 1 (7): 503-514 (2002).

(56) References Cited

OTHER PUBLICATIONS

Paroo et al., "Challenges for RNAi in vivo," Trends in Biotech, 22(8): 390-394 (2004).

Patel et al., "A Novel Protective Role for the Innate Immunity Toll-Like Receptor 3 (TLR3) in the Retina via Stat3," Mol Cell Neurosci, 63: 38-48 (2014).

Raouane et al., "Lipid conjugated oligonucleotides: a useful strategy for delivery," Bioconjugate Chem, 23:1091-104 (2012).

Rose et al., "Functional Polarity is Introduced by Dicer Processing of Short Substrate RNAs," Nucleic Acids Res, 33: 4140-4156 (2005).

Sano et al., "Effect of asymmetric terminal structures of short RNA duplexes on the RNA interference activity and strand selection," Nucleic Acids Research (2008), 36: 5812-5821.

Sharp et al., "RNA-interference-2001," Genes & Development, (2001), 15:485-490.

Sioud et al., "Cationic liposome-mediated delivery of siRNAs in adult mice," Biochem Biophys Res Commun. Dec. 26, 2003; 312(4):1220-5.

Sisco et al., "Antisense Inhibition of Connective Tissue Growth Factor (CTGF/CCN2) mRNA Limits Hypertrophic Scarring Without Affecting Wound Healing in Vivo," Wound Repair Regen, 16: 661-673 (2008).

Song et al., "The Crystal Structure of the Argonaute2 PAZ Domain Reveals an RNA Binding Motif in RNAi Effector Complexes," Nat Struct Biol, 10(12): 1026-1032 (2003).

Soutschek et al., "Therapeutic Silencing of an Endogenous Gene by Systemic Adminstration of Modified siRNAs," Nature, 432: 173-178 (2004).

Sun et al., "Asymmetic RNA duplexes mediate RNA interference in mammalian cells," Nature Biotechnology, 26: 1379-1382 (2008).

Ui-Tei et al., "Essential Notes Regarding the Design of Functional siRNAs for Efficient Mammalian RNAi," J Biomed Biotechnol, 2006; 2006(4):65052. doi: 10.1155/JBB/2006/65052.

Ui-Tei et al., "Guidelines for the selection of highly effective siRNA sequences for mammalian and chick RNA interference," (2004), Nucleic Acids Research, vol. 32, pp. 936-948.

Vasdudevan et al., "Switching from Repression to Activation: MicroRNAs Can Up-Regulate Translation," Science, 318: 1931-1934 (2007).

Wang et al., "Nucleation, Propagation and Cleavage of Target RNAs in Ago Silencing Complexes," Nature, 461: 754-762 (2009).

Yang et al., "HENI recognizes 21-24 nt small RNA duplexes and deposits a methyl group onto the 2' OH of the 3' terminal nucleotide," Nucleic Acids Research, 34: 667-675 (2006).

Yuan et al., "Asymmetric siRNA: New Strategy to Improve Specificity and Reduce Off-Target Gene Expression", Human Gene Therapy 23:521-532 (2013).

Zamore, "RNA interference: listening to the sound of silence," Nature Structural Biology, (2001), 8(9):746-750.

TREATMENT OF AGE-RELATED MACULAR DEGENERATION USING RNA COMPLEXES THAT TARGET MYD88 OR TLR3

RELATED APPLICATIONS

This application is a divisional of U.S. patent application Ser. No. 15/352,322, which claims priority to U.S. Provisional Patent Application No. 62/255,878, filed Nov. 16, 2015, the disclosure of each of which is hereby incorporated by reference in its entirety.

SEQUENCE LISTING

The instant application contains a Sequence Listing which has been filed electronically in ASCII format and is hereby incorporated by reference in its entirety. Said ASCII copy, created on Jul. 27, 2017, is named OPH-00601(32896-00601) SL.txt and is 105,629 bytes in size.

BACKGROUND

Age-related macular degeneration (AMD) is a disease that results from the degeneration of the retinal pigmented epithelium lining in the eye's macula, which leads to vision loss. The macula is a small area in the retina made up of the light-sensitive tissues lining the back of the eye and plays a critical role in central vision. AMD is one of the leading causes of blindness worldwide.

AMD occurs in "wet" and "dry" forms. Wet AMD is the result of abnormal blood vessel growth in the retina. In wet AMD, increased amount of vascular endothelial growth factor (VEGF) contributes to this neovascularization, so therapeutic options include the use of VEGF inhibitors are used. However, many patients treated with VEGF inhibitors develop geographic atrophy (GA), which is a primary symptom of late dry macular degeneration, within a few years of treatment. The disease pathogenesis of dry AMD is unclear and no medical treatment is currently available for dry AMD. Therefore, the development of therapeutics that can treat both wet and dry macular degeneration needed.

SUMMARY

MyD88 and TLR3 play important roles in the onset of both dry AMD and wet AMD. Unlike VEGF antibodies, which are ineffective at treating dry macular degeneration, a therapeutic agent targeting MyD88 or TLR3 can be used to treat both wet and dry macular degeneration.

In certain aspects, provided herein are RNA complexes that inhibit Myeloid differentiation primary response gene 88 (MyD88) and/or Toll-like receptor 3 (TLR3) and are useful in the treatment of age-related macular degeneration (AMD) (e.g., wet and/or dry AMD). In certain aspects, provided herein are pharmaceutical compositions comprising such RNA complexes and methods of using such RNA complexes and pharmaceutical compositions.

In certain aspects, provided herein is an RNA complex comprising an antisense strand having sequence complementarity to a MyD88 mRNA sequence (e.g., a human MyD88 mRNA sequence) and a sense strand having sequence complementarity to the antisense strand. In some embodiments, the RNA complex is capable of inhibiting MyD88 expression by a cell. In certain embodiments, the RNA complex is capable of inhibiting MyD88 production by a cell. In some embodiments, the RNA complex is an asymmetric short interfering RNA (an asiRNA). In some embodiments, the RNA complex is a long asymmetric short interfering RNA (a lasiRNA).

In some embodiments, the antisense strand is at least 19 nucleotides (nt) in length. In some such embodiments, the antisense strand is 19 to 21 nt in length (i.e., 19, 20 or 21 nt in length). In other such embodiments, the antisense strand is at least 24 nt in length (e.g., 24 to 121 nt in length), e.g., 31 nt in length. In certain embodiments, at least 13, 14, 15, 16, 17, 18, 19, 20 or 21 nt of the antisense strand are complementary to the MyD88 mRNA sequence. In some embodiments, the sense strand is 15 to 17 nt in length (i.e., 15 nt in length, 16 nt in length or 17 nt in length). In certain embodiments, at least 15 nt, at least 16 nt or at least 17 nt of the sense strand are complementary to the sequence of the antisense strand. Representative RNA complexes include the RNA complexes listed in Table 1, Table 2, Table 3, Table 4, Table 5 or Table 6.

In certain aspects, provided herein is an RNA complex comprising an antisense strand having sequence complementarity to a TLR3 mRNA sequence (e.g., a human TLR3 mRNA sequence) and a sense strand having sequence complementarity to the antisense strand. In some embodiments, the RNA complex is capable of inhibiting TLR3 expression by a cell. In certain embodiments, the RNA complex is capable of inhibiting TLR3 production by a cell. In some embodiments, the RNA complex is an asymmetric short interfering RNA (an asiRNA). In some embodiments, the RNA complex is a long asymmetric short interfering RNA (a lasiRNA).

In some embodiments, the antisense strand is at least 19 nucleotides (nt) in length. In some such embodiments, the antisense strand is 19 to 21 nt in length (i.e., 19, 20 or 21 nt in length). In other such embodiments, the antisense strand is at least 24 nt in length (e.g., 24 to 121 nt in length). In certain embodiments, at least 13, 14, 15, 16, 17, 18, 19, 20 or 21 nt of the antisense strand are complementary to the TLR3 mRNA sequence. In some embodiments, the sense strand is 15 to 17 nt in length (i.e., 15 nt in length, 16 nt in length or 17 nt in length). In certain embodiments, at least 15 nt, at least 16 nt or at least 17 nt of the sense strand are complementary to the sequence of the antisense strand. Representative RNA complexes include the RNA complexes listed in Table 7, Table 8 or Table 10.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond and/or a cholesterol moiety. In some such embodiments, the 2'-O-methyl nucleoside is positioned at the 3' terminus of the sense strand. In some such embodiments, the 3' terminal region of the sense strand comprises a plurality of 2'-O-methylated nucleosides (e.g., 2, 3, 4, 5 or 6 2'-O-methylated nucleosides within 6 nucleosides of the 3' terminus). In other embodiments, the 2'-O-methyl nucleoside is positioned at the 3' terminus of the antisense strand. In some such embodiments, 3' terminal region of the antisense strand comprises a plurality of 2'-O-methylated nucleosides (e.g., 2, 3, 4, 5 or 6 2'-O-methylated nucleosides within 6 nucleosides of the 3' terminus). In some embodiments, both the 3' terminal region of the sense strand and the 3' terminal region of the antisense strand comprise a plurality of 2'-O-methylated nucleosides. Representative RNA complexes include the modified RNA complexes listed in Table 3, Table 4, Table 5, Table 6, Table 8 or Table 10. In certain embodiments, the RNA complex is not cytotoxic.

In some embodiments, the RNA complex provided herein comprises a phosphorothioate bond. In some embodiments, at least 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some such embodiments, all of the bonds between the ribonucleotides in the sense strand of the RNA complex are phosphorothioate bonds. Similarly, in some embodiments, at least 25%, 30%, 35%, 40%, 45%, 50%, 55%, 60%, 65%, 70%, 75%, 80%, 85%, 90% or 95% of the bonds between the ribonucleotides in the antisense strand of the RNA complex are phosphorothioate bonds. In some such embodiments, all of the bonds between the ribonucleotides in the antisense strand of the RNA complex are phosphorothioate bonds.

In some embodiments, the RNA complex provided herein comprises a cholesterol moiety. In some embodiments, the cholesterol moiety is attached to the 3' terminus of the sense strand.

In certain aspects, provided herein is a pharmaceutical composition comprising an RNA complex provided herein and a pharmaceutically acceptable carrier. In certain embodiments, the pharmaceutical composition is formulated for administration to the eye (e.g., as an eye drop). In some embodiments, the pharmaceutical composition is formulated for intravitreal delivery.

In certain aspects, provided herein is a method of inhibiting MyD88 and/or TLR3 expression by a cell comprising contacting the cell with an RNA complex and/or a pharmaceutical composition provided herein. In some embodiments, the cell is present in the eye of a human subject (e.g., a human subject with wet or dry AMD). In certain aspects, provided herein is a method of treating a human subject for AMD (e.g., wet AMD and/or dry AMD) comprising administering to the subject, e.g., to the eye, an RNA complex and/or pharmaceutical composition provided herein. In some embodiments, the RNA complex and/or a pharmaceutical composition is administered to the eye by intravitreal injection.

DETAILED DESCRIPTION

General

Figure 1:
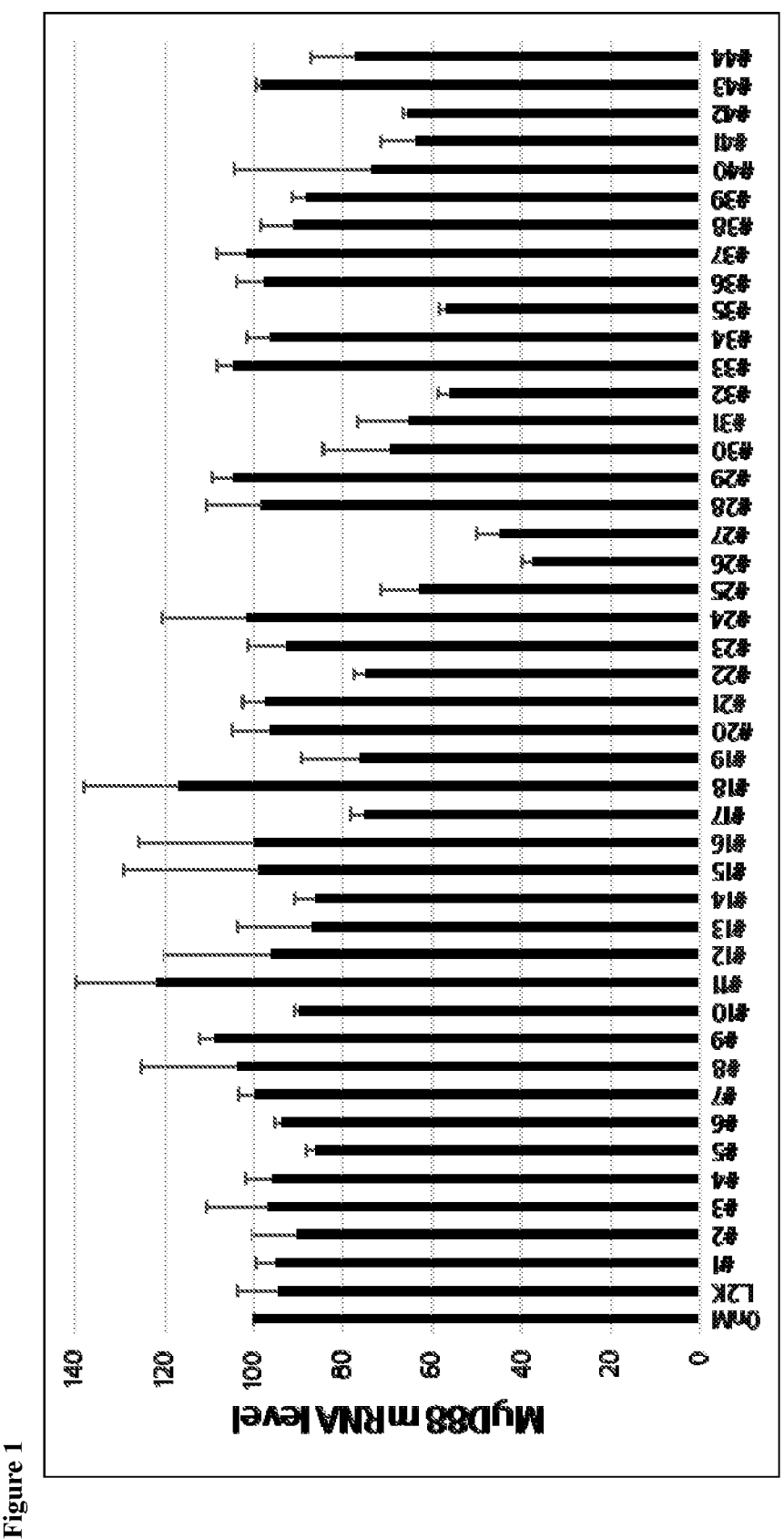
FIG. 1 shows the gene silencing efficiency of exemplary asiRNAs that target MyD88. The asiRNAs were transfected into HeLa cells at a concentration of 0.3 nM, and, after 24 hours, the degree of MyD88 mRNA expression was determined using real-time PCR. The mean and standard deviation of three repeat experiments are depicted.

In certain aspects, provided herein are asymmetric RNA complexes (e.g., asiRNAs or lasiRNAs) that inhibit MyD88 and/or TLR3 expression and are therefore useful for the treatment of AMD (e.g., wet AMD and/or dry AMD). In some embodiments, the RNA complexes are chemically modified to be capable of penetrating a cell without need for a transfection vehicle. In some embodiments, the RNA complex is an RNA complex listed in Table 1, Table 2, Table 3, Table 4, Table 5, Table 6, Table 8 or Table 10. In certain aspects, provided herein are pharmaceutical compositions comprising such RNA complexes and methods of using such RNA complexes and pharmaceutical compositions.

MyD88 is a protein that plays an important role in the onset of both dry AMD and wet AMD as one of the proteins that activate the immune response. Unlike previous AMD therapies that target VEGF, which are ineffective at treating dry macular degeneration, therapies targeting MyD88 can be used to treat both wet and dry AMD. An exemplary human MyD88 cDNA sequence is provided below.

```
Human MyD88 cDNA sequence.
                                                           (SEQ ID NO: 1)
       1   agattcctac ttcttacgcc ccccacatca cccgcctcga gacctcaagg gtagaggtgg 61   gcacccccgc ctccgcactt ttgctcgggg ctccagattg tagggcaggg cggcgcttct 121   cggaaagcga aagccggcgg ggcggggcgg gtgccgcagg agaaagagga agcgctggca 181   gacaatgcga cccgaccgcg ctgaggctcc aggaccgccc gccatggctg caggaggtcc 241   cggcgcgggg tctgcggccc cggtctcctc cacatcctcc cttccctgg  ctgctctcaa 301   catgcgagtg cggcgccgcc tgtctctgtt cttgaacgtg cggacacagg tggcggccga 361   ctggaccgcg ctggcggagg agatggactt tgagtacttg gagatccggc aactggagac 421   acaagcggac cccactggca ggctgctgga cgcctggcag ggacgccctg gcgcctctgt 481   aggccgactg ctcgagctgc ttaccaagct gggccgcgac gacgtgctgc tggagctggg 541   acccagcatt gaggaggatt gccaaaagta tatcttgaag cagcagcagg aggaggctga 601   gaagccttta caggtggccg ctgtagacag cagtgtccca cggacagcag agctggcggg 661   catcaccaca cttgatgacc ccctggggca tatgcctgag cgtttcgatg ccttcatctg 721   ctattgcccc agcgacatcc agtttgtgca ggagatgatc cggcaactgg aacagacaaa 781   ctatcgactg aagttgtgtg tgtctgaccg cgatgtcctg cctggcacct gtgtctggtc 841   tattgctagt gagctcatcg aaaagaggtg ccgccggatg gtggtggttg tctctgatga 901   ttacctgcag agcaaggaat gtgacttcca gaccaaattt gcactcagcc tctctccagg 961   tgcccatcag aagcgactga tccccatcaa gtacaaggca atgaagaaag agttccccag 1021   catcctgagg ttcatcactg tctgcgacta caccaacccc tgcaccaaat cttggttctg 1081   gactcgcctt gccaaggcct tgtccctgcc ctgaagactg ttctgaggcc ctgggtgtgt 1141   gtgtatctgt ctgcctgtcc atgtacttct gccctgcctc ctcctttcgt tgtaggagga 1201   atctgtgctc tacttacctc tcaattcctg gagatgccaa cttcacagac acgtctgcag
```

```
1261  cagctggaca tcacatttca tgtcctgcat ggaaccagtg gctgtgagtg gcatgtccac
1321  ttgctggatt atcagccagg acactataga acaggaccag ctgagactaa aaggaccag
1381  cagagccagc tcagctctga gccattcaca catcttcacc ctcagtttcc tcacttgagg
1441  agtgggatgg ggagaacaga gagtagctgt gtttgaatcc ctgtaggaaa tggtgaagca
1501  tagctctggg tctcctgggg gagaccaggc ttggctgcgg gagagctggc tgttgctgga
1561  ctacatgctg gccactgctg tgaccacgac actgctgggg cagcttcttc cacagtgatg
1621  cctactgatg cttcagtgcc tctgcacacc gcccattcca cttcctcctt ccccacaggg
1681  caggtgggga agcagtttgg cccagcccaa ggagacccca cctttgagcct tatttcctaa
1741  tgggtccacc tctcatctgc atctttcaca cctcccagct tctgcccaac cttcagcagt
1801  gacaagtccc caagagactc gcctgagcag cttgggctgc ttttcatttc cacctgtcag
1861  gatgcctgtg gtcatgctct cagctccacc tggcatgaga agggatcctg gcctctggca
1921  tattcatcaa gtatgagttc tggggatgag tcactgtaat gatgtgagca gggagccttc
1981  ctccctgggc cacctgcaga gagctttccc accaactttg taccttgatt gccttacaaa
2041  gttatttgtt tacaaacagc gaccatataa aagcctcctg ccccaaagct tgtgggcaca
2101  tgggcacata cagactcaca tacagacaca cacatatatg tacagacatg tactctcaca
2161  cacacaggca ccagcataca cacgttttc taggtacagc tcccaggaac agctaggtgg
2221  gaaagtccca tcactgaggg agcctaacca tgtccctgaa caaaaattgg gcactcatct
2281  attccttttc tcttgtgtcc ctactcattg aaaccaaact ctggaaagga cccaatgtac
2341  cagtatttat acctctaatg aagcacagag agaggaagag agctgcttaa actcacacaa
2401  caatgaactg cagacacagc tgttctctcc ctctctcctt cccagagcaa tttatacttt
2461  accctcaggc tgtcctctgg ggagaaggtg ccatggtctt aggtgtctgt gccccaggac
2521  agaccctagg accctaaatc caatagaaaa tgcatatctt tgctccactt tcagccaggc
2581  tggagcaagg tacctttttct taggatcttg ggagggaatg gatgcccctc tctgcatgat
2641  cttgttgagg catttagctg ccatgcacct gtccccttt aatactgggc attttaaagc
2701  catctcaaga ggcatcttct acatgttttg tacgcattaa aataatttca aagatatctg
2761  agaaaagccg atatttgcca ttcttcctat atcctggaat atatcttgca tcctgagttt
2821  ataataataa ataatattct accttggaaa aaaaaaaaa aa
```

Toll-like receptor 3 (TLR3) plays a pivotal role in innate immune system as a type 1 transmembrane signaling molecule. TLR3 ligands include double-stranded RNA formed by the proliferation of RNA virus and polyinosinic-polycytidylic (polyI:C), a dsRNA analogue. In individuals suffering from dry AMD, alu-RNAs, a type of dsRNA, accumulate in retinal epithelial cells. Compared to a healthy individuals, people suffering from wet AMD had high expression of levels of TLR3 in peripheral blood mononuclear cells, indicating that TLR3 is closely associated in the pathogenesis of both dry and wet AMD. An exemplary human MyD88 cDNA sequence is provided below.

Human TLR3 cDNA sequence.
(SEQ ID NO: 2)
```
  1  cactttcgag agtgccgtct atttgccaca cacttccctg atgaaatgtc tggatttgga
 61  ctaaagaaaa aaggaaaggc tagcagtcat ccaacagaat catgagacag actttgcctt
121  gtatctactt ttgggggggc cttttgccct ttgggatgct gtgtgcatcc tccaccacca
181  agtgcactgt tagccatgaa gttgctgact gcagccacct gaagttgact caggtacccg
241  atgatctacc cacaaacata acagtgttga accttaccca taatcaactc agaagattac
301  cagccgccaa cttcacaagg tatagccagc taactagctt ggatgtagga tttaacacca
361  tctcaaaact ggagccagaa ttgtgccaga aacttcccat gttaaaagtt ttgaacctcc
```

```
 421   agcacaatga gctatctcaa ctttctgata aaacctttgc cttctgcacg aatttgactg
 481   aactccatct catgtccaac tcaatccaga aaattaaaaa taatccctt gtcaagcaga
 541   agaatttaat cacattagat ctgtctcata atggcttgtc atctacaaaa ttaggaactc
 601   aggttcagct ggaaaatctc caagagcttc tattatcaaa caataaaatt caagcgctaa
 661   aaagtgaaga actggatatc tttgccaatt catctttaaa aaaattagag ttgtcatcga
 721   atcaaattaa agagttttct ccagggtgtt ttcacgcaat tggaagatta tttggcctct
 781   ttctgaacaa tgtccagctg gtcccagcc ttacagagaa gctatgtttg gaattagcaa
 841   acacaagcat tcggaatctg tctctgagta acagccagct gtccaccacc agcaatacaa
 901   ctttcttggg actaaagtgg acaaatctca ctatgctcga tctttcctac aacaacttaa
 961   atgtggttgg taacgattcc tttgcttggc ttccacaact agaatatttc ttcctagagt
1021   ataataatat acagcatttg ttttctcact ctttgcacgg cttttcaat gtgaggtacc
1081   tgaatttgaa acggtctttt actaaacaaa gtatttccct tgcctcactc cccaagattg
1141   atgattttc ttttcagtgg ctaaaatgtt tggagcacct taacatggaa gataatgata
1201   ttccaggcat aaaaagcaat atgttcacag gattgataaa cctgaaatac ttaagtctat
1261   ccaactcctt tacaagttg cgaactttga caaatgaaac atttgtatca cttgctcatt
1321   ctcccttaca catactcaac ctaaccaaga ataaaatctc aaaaatagag agtgatgctt
1381   tctcttggtt gggccaccta gaagtacttg acctgggcct taatgaaatt gggcaagaac
1441   tcacaggcca ggaatggaga ggtctagaaa atattttcga aatctatctt tcctacaaca
1501   agtacctgca gctgactagg aactcctttg ccttggtccc aagccttcaa cgactgatgc
1561   tccgaagggt ggcccttaaa aatgtggata gctctccttc accattccag cctcttcgta
1621   acttgaccat tctggatcta agcaacaaca acatagccaa cataaatgat gacatgttgg
1681   agggtcttga gaaactagaa attctcgatt tgcagcataa caacttagca cggctctgga
1741   aacacgcaaa ccctggtggt cccatttatt tcctaaaggg tctgtctcac ctccacatcc
1801   ttaacttgga gtccaacggc tttgacgaga tcccagttga ggtcttcaag gatttatttg
1861   aactaaagat catcgattta ggattgaata atttaaacac acttccagca tctgtctttta
1921   ataatcaggt gtctctaaag tcattgaacc ttcagaagaa tctcataaca tccgttgaga
1981   agaaggtttt cgggccagct ttcaggaacc tgactgagtt agatatgcgc tttaatccct
2041   ttgattgcac gtgtgaaagt attgcctggt tgttaattg gattaacgag acccatacca
2101   acatccctga gctgtcaagc cactaccttt gcaacactcc acctcactat catgggttcc
2161   cagtgagact ttttgataca tcatcttgca aagacagtgc ccccttgaa ctcttttca
2221   tgatcaatac cagtatcctg ttgatttta tcttattgt acttctcatc cactttgagg
2281   gctggaggat atcttttat tggaatgttt cagtacatcg agttcttggt ttcaaagaaa
2341   tagacagaca gacagaacag tttgaatatg cagcatatat aattcatgcc tataaagata
2401   aggattgggt ctgggaacat ttctcttcaa tggaaaagga agaccaatcc ctcaaatttt
2461   gtctggaaga aagggacttt gaggcgggtg ttttttgaact agaagcaatt gttaacagca
2521   tcaaaagaag cagaaaaatt atttttgtta taacaccaca tctattaaaa gacccattat
2581   gcaaaagatt caaggtacat catgcagttc aacaagctat tgaacaaaat ctggattcca
2641   ttatattggt tttccttgag gagattccag attataaact gaaccatgca ctctgtttgc
2701   gaagaggaat gtttaaatct cactgcatct tgaactggcc agttcagaaa gaacggatag
2761   gtgcctttcg tcataaattg caagtagcac ttggatccaa aaactctgta cattaaattt
2821   atttaaatat tcaattagca aaggagaaac tttctcaatt taaaaagttc tatggcaaat
```

```
2881   ttaagttttc cataaaggtg ttataatttg tttattcata tttgtaaatg attatattct 2941   atcacaatta catctcttct aggaaaatgt gtctccttat ttcaggccta tttttgacaa 3001   ttgacttaat tttacccaaa ataaaacata taagcacgta aaaaaaaaaa aaaaaa
```

In some embodiments, the RNA complexes described herein are asiRNAs or lasiRNAs. As used herein, the term asiRNA refers to double-stranded asymmetrical short interfering RNA molecules that have a 19-21 nt antisense strand and a 13-17 nt sense strand. Additional information on asiRNAs can be found in U.S. Pat. Pub. No. 2012/0238017 and in Chang et al., *Mol. Ther.* 17:725-732 (2009), each of which is hereby incorporated by reference in its entirety. As used herein, the term lasiRNA refers to double-stranded long asymmetrical interfering RNA molecules that have a 13-21 nt sense strand and an antisense strand of greater than 24 nt. Additional information on lasiRNAs can be found in U.S. Pat. Pub. No. 2013/0273657, which is hereby incorporated by reference in its entirety.

In some embodiments, the RNA complexes described herein are delivered to cells using a delivery vehicle, such as liposomes, cationic polymers, cell penetrating peptides (CPPs), protein transduction domains (PTDs), antibodies and/or aptamers. In some embodiments, the RNA complex described herein is chemically modified so as to not require the use of such delivery vehicles to mediate MyD88 and/or TLR3 inhibition in a cell. Such RNA complexes are referred to herein as cell-penetrating asiRNAs (cp-asiRNAs) or cell-penetrating lasiRNAs (cp-lasiRNAs).

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

As used herein, the terms "interfering nucleic acid," "inhibiting nucleic acid" are used interchangeably. Interfering nucleic acids generally include a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. Interfering RNA molecules include, but are not limited to, antisense molecules, siRNA molecules, asiRNA molecules, lasiRNA molecules, single-stranded siRNA molecules, miRNA molecules and shRNA molecules. Such an interfering nucleic acids can be designed to block or inhibit translation of mRNA or to inhibit natural pre-mRNA splice processing, or induce degradation of targeted mRNAs, and may be said to be "directed to" or "targeted against" a target sequence with which it hybridizes. Interfering nucleic acids may include, for example, peptide nucleic acids (PNAs), locked nucleic acids (LNAs), 2'-O-Methyl oligonucleotides and RNA interference agents (siRNA agents). RNAi molecules generally act by forming a heteroduplex with the target molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid of the target in the manner described above.

The terms "polynucleotide", and "nucleic acid" are used interchangeably. They refer to a polymeric form of nucleotides, whether deoxyribonucleotides, ribonucleotides, or analogs thereof, in any combination and of any length. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The phrase "pharmaceutically-acceptable carrier" as used herein means a pharmaceutically-acceptable material, composition or vehicle, such as a liquid or solid filler, diluent, excipient, or solvent encapsulating material.

An oligonucleotide "specifically hybridizes" to a target polynucleotide if the oligomer hybridizes to the target under physiological conditions, with a Tm substantially greater than 45° C., or at least 50° C., or at least 60° C.-80° C. or higher. Such hybridization corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

RNA Complexes

In certain aspects, provided herein are RNA complexes that target MyD88 or TLR3 mRNA and inhibit MyD88 or TLR3 expression by a cell. The nucleic acid sequence of human MyD88 and TLR3 mRNA is provided in the sequence listing at the end of the disclosure.

In certain aspects, provided herein is an RNA complex comprising an antisense strand having sequence complementarity to a MyD88 or TLR3 mRNA sequence (e.g., a human MyD88 or TLR3 mRNA sequence) and a sense strand having sequence complementarity to the antisense strand. In some embodiments, the RNA complex is capable of inhibiting MyD88 or TLR3 expression by a cell. In some embodiments, the RNA complex is an asymmetric short interfering RNA (an asiRNA). In some embodiments, the RNA complex is a long asymmetric short interfering RNA (a lasiRNA). In some embodiments, the RNA complex is an RNA complex listed in Table 1, Table 2, Table 3, Table 4, Table 5, Table 6, Table 8 or Table 10. The RNA complexes described herein can contain RNA bases, non-RNA bases or a mixture of RNA bases and non-RNA bases. For example, certain RNA complexes provided herein can be primarily composed of RNA bases but also contain DNA bases or non-naturally occurring nucleotides.

In some embodiments, the antisense strand is at least 19 nucleotides (nt) in length. In some embodiments, the antisense strand is 19 to 21 nt in length (i.e., 19, 20 or 21 nt in length). In some embodiments, at least 13, 14, 15, 16, 17, 18, 19, 20 or 21 nt of the antisense strand are complementary to the MyD88 or TLR3 mRNA sequence. Perfect complementarity is not necessary. In some embodiments, the antisense strand is perfectly complementary to the MyD88 or TLR3 mRNA sequence.

In some embodiments, the antisense strand is at least 24 nt in length (e.g., at least 25 nt in length, at least 26 nt in length, at least 27 nt in length, at least 28 nt in length, at least 29 nt in length, at least 30 nt in length or at least 31 nt in length). In some embodiments, the antisense strand is no greater than 124 nt in length (e.g., no greater than 100 nt in length, no greater than 90 nt in length, no greater than 80 nt in length, no greater than 70 nt in length, no greater than 60 nt in length, no greater than 50 nt in length or no greater than 40 nt in length. In some embodiments, the antisense strand is 31 nt in length. In some embodiments, at least 16, 17, 18, 19, 20, 21, 22, 23, 24, 25, 26, 27, 29, 29, 30 or 31 nt of the antisense strand are complementary to the MyD88 or TLR3 mRNA sequence. Perfect complementarity is not necessary. In some embodiments, the antisense strand is perfectly complementary to the MyD88 or TLR3 mRNA sequence.

In some embodiments, the sense strand is 15 to 17 nt in length (i.e., 15 nt in length, 16 nt in length or 17 nt in length). In some embodiments, at least 15 nt, at least 16 nt or at least 17 nt of the sense strand are complementary to the sequence of the antisense strand. In some embodiments the sense strand is perfectly complementary to the sequence of the antisense strand.

In some embodiments, the antisense strand and the sense strand form a complex in which the 5' end of the antisense strand and the 3' end of the sense strand form a blunt end. In some embodiments, the antisense strand and the sense strand form a complex in which the 5' end of the antisense strand overhangs the 3' end of the sense strand (e.g., by 1, 2, 3, 4 or 5 nt). In some embodiments, the antisense strand and the sense strand form a complex in which the 5' end of the sense strand overhangs the 3' end of the antisense strand (e.g., by 1, 2, 3, 4 or 5 nt).

In some embodiments, the antisense strand and/or the sense strand of the RNA complex has a sense strand sequence and/or an antisense strand sequence selected from the sequences listed in Table 1, Table 2, Table 3, Table 4, Table 5, Table 6, Table 8 or Table 10.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a cholesterol moiety. In some embodiments, the RNA complex is a modified RNA complex listed in Table 2 or Table 4. In certain embodiments, the RNA complex is not cytotoxic.

The RNA complexes described herein can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, each of which is hereby incorporated by reference in its entirety.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition. The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969, 766, 7,211,668, 7,022,851, 7,125,994, 7,145,006 and 7,179, 896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C3-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., *Chemical Communications* (1998) 455; *Tetrahedron* (1998) 54:3607, and *Accounts of Chem. Research* (1999) 32:301); Obika, et al., *Tetrahedron Letters* (1997) 38:8735; (1998) 39:5401, and *Bioorganic Medicinal Chemistry* (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA-containing compound where each LNA subunit is separated by a DNA subunit. Certain compounds are composed of alternating LNA and DNA subunits where the intersubunit linker is phosphorothioate.

In certain embodiments, the RNA complex is linked to a cholesterol moiety. In some embodiments, the cholesterol moiety is attached to the 3' terminus of the sense strand. In some embodiments, the cholesterol moiety is attached to the 3' terminus of the antisense strand. In some embodiments, the cholesterol moiety is attached to the 5' terminus of the sense strand. In some embodiments, the cholesterol moiety is attached to the 5' terminus of the antisense strand.

In some embodiments, the RNA complex comprises a 2'-O-methylated nucleoside. 2'-O-methylated nucleosides carry a methyl group at the 2'-OH residue of the ribose molecule. 2'-O-Me-RNAs show the same (or similar) behavior as RNA, but are protected against nuclease degradation. 2'-O-Me-RNAs can also be combined with phosphothioate oligonucleotides (PTOs) for further stabilization. 2'-O-Me-RNAs (phosphodiester or phosphothioate) can be synthesized according to routine techniques in the art (see, e.g., Yoo et al., *Nucleic Acids Res.* 32:2008-16, 2004, which is hereby incorporated by reference).

In some embodiments, the 2'-O-methyl nucleoside is positioned at the 3' terminus of the sense strand. In some embodiments, 3' terminal region of the sense strand comprises a plurality of 2'-O-methylated nucleosides (e.g., 2, 3, 4, 5 or 6 2'-O-methylated nucleosides within 6 nucleosides of the 3' terminus). In some embodiments, the 2'-O-methyl nucleoside is positioned at the 3' terminus of the antisense strand. In some embodiments, 3' terminal region of the antisense strand comprises a plurality of 2'-O-methylated nucleosides (e.g., 2, 3, 4, 5 or 6 2'-O-methylated nucleosides within 6 nucleosides of the 3' terminus). In some embodiments, both the 3' terminal region of the sense strand and the 3' terminal region of the antisense strand comprise a plurality of 2'-O-methylated nucleosides. In some embodiments, the sense strand comprises 2'-O-methylated nucleosides that alternate with unmodified nucleosides. In some embodiments, the sense strand comprises a contiguous sequence of 2, 3, 4, 5, 6, 7 or 8 2'-O-methylated nucleosides that alternate with unmodified nucleosides. In some embodiments, the anti-sense strand comprises 2'-O-methylated nucleosides that alternate with unmodified nucleosides. In some embodiments, the anti-sense strand comprises a contiguous sequence of 2, 3, 4, 5, 6, 7 or 8 2'-O-methylated nucleosides that alternate with unmodified nucleosides.

In some embodiments, the RNA complex comprises a phosphorothioate bond. "Phosphorothioates" (or S-oligos) are a variant of normal DNA in which one of the nonbridging oxygens is replaced by a sulfur. The sulfurization of the internucleotide bond reduces the action of endo- and exo-nucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-benzodithiol-3-one 1,1-dioxide (BDTD) (see, e.g., Iyer et al., *J. Org. Chem.* 55, 4693-4699, 1990). The latter methods avoid the problem of elemental sulfur's insolubility in most organic solvents and the toxicity of carbon disulfide. The TETD and BDTD methods also yield higher purity phosphorothioates.

In some embodiments, at least 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some embodiments, all of the bonds between the ribonucleotides in the sense strand of the RNA complex are phosphorothioate bonds.

In some embodiments, at least 25%, 30%, 35%, 40%, 45%, 50%, 55%, 60%, 65%, 70%, 75%, 80%, 85%, 90% or 95% of the bonds between the ribonucleotides in the antisense strand of the RNA complex are phosphorothioate bonds. In some embodiments, all of the bonds between the ribonucleotides in the antisense strand of the RNA complex are phosphorothioate bonds.

The RNA complexes described herein may be contacted with a cell or administered to an organism (e.g., a human). Alternatively, constructs and/or vectors encoding the RNA complexes may be contacted with or introduced into a cell or organism. In certain embodiments, a viral, retroviral or lentiviral vector is used.

The RNA complexes described herein can be prepared by any appropriate method known in the art. For example, in some embodiments, the RNA complexes described herein are prepared by chemical synthesis or in vitro transcription.

In certain aspects, provided herein is a pharmaceutical composition comprising an RNA complex provided herein and a pharmaceutically acceptable carrier. In certain embodiments, the pharmaceutical composition is formulated for delivery to the eye (e.g., as an eye drop). In some embodiments, the pharmaceutical composition is formulated for intravitreal delivery.

In some embodiments, the pharmaceutical composition further comprises a second agent for treatment of AMD (e.g., an anti-VEGF therapeutic, such as bevacizumab, ranibizumab, pegaptanib and/or aflibercept). In certain embodiments, the pharmaceutical composition does not comprise a transfection vehicle. In some embodiments, the pharmaceutical composition comprises a delivery vehicle (e.g., liposomes, cationic polymers, cell penetrating peptides (CPPs), protein transduction domains (PTDs), antibodies and/or aptamers). In some embodiments, the composition includes a combination of multiple (e.g., two or more) of the RNA complexes described herein.

Methods of preparing these formulations or compositions include the step of bringing into association an RNA complex described herein with the carrier and, optionally, one or more accessory ingredients. In general, the formulations are prepared by uniformly and intimately bringing into association an agent described herein with liquid carriers.

Therapeutic Methods

In certain aspects, provided herein is a method of inhibiting MyD88 and/or TLR3 expression by a cell comprising contacting the cell with an RNA complex provided herein. In some embodiments, the RNA complex is a modified RNA complex and the cell is contacted with the RNA complex in the absence of a transfection vehicle. In some embodiments, the cell is contacted with the RNA complex in the presence of a delivery vehicle (e.g., a liposome, cationic polymer, cell penetrating peptide (CPPs), protein transduction domain (PTDs), antibody and/or aptamer). In some embodiments, the cell is present in the eye of a human subject. In some embodiments, the subject has AMD (e.g., wet AMD or dry AMD).

In certain aspects, provided herein is a method of treating a human subject for AMD (e.g., wet AMD or dry AMD) comprising administering to the subject an RNA complex or pharmaceutical composition provided herein. In certain embodiments, the RNA complex or pharmaceutical composition is administered to the eye of the subject. In some embodiments, the RNA complex or pharmaceutical composition self-administered by the subject.

In the present methods, an RNA complex described herein can be administered to the subject, for example, as nucleic acid without delivery vehicle (e.g., for cp-asiRNAs and cp-lasiRNAs), in combination with a delivery reagent, and/or as a nucleic acid comprising sequences that express the RNA complex described herein. In some embodiments, any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. *Nucleic Acids Res.*, 32(13):e109 (2004); Hanai et al. *Ann NY Acad Sci.*, 1082:9-17 (2006); and Kawata et al. *Mol Cancer Ther.*, 7(9):2904-12 (2008); each of which is incorporated herein in their entirety. Exemplary interfering nucleic acid delivery systems are provided in U.S. Pat. Nos. 8,283,461, 8,313,772, 8,501,930, 8,426,554, 8,268,798 and 8,324,366, each of which is hereby incorporated by reference in its entirety.

In some embodiments of the methods described herein, liposomes are used to deliver an RNA complex described herein to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

The pharmaceutical compositions disclosed herein may be delivered by any suitable route of administration, including topically, intravitreally, orally and parenterally. In certain embodiments the pharmaceutical compositions are delivered generally (e.g., via oral or parenteral administration). In certain other embodiments the pharmaceutical compositions are delivered locally through direct administration to the eye.

Actual dosage levels of the RNA complexes in the pharmaceutical compositions may be varied so as to obtain an amount of RNA complex that is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved.

In general, a suitable daily dose of an RNA complex described herein will be that amount of the RNA complex which is the lowest dose effective to produce a therapeutic effect. Such an effective dose will generally depend upon the factors described above.

EXEMPLIFICATION

Example 1: Screening for MyD88-Specific Asymmetric Small Interfering RNAs

To identify asymmetric small interfering RNAs (asiRNAs) that inhibit MyD88 with high efficiency, 44 asiRNAs were synthesized and screened. The nucleic acid sequences of the screened asiRNAs are provided in Table 1.

TABLE 1

Nucleic acid sequences for exemplary MyD88-targeting asiRNA.

| asiRNA SEQUENCE | SEQ ID NO: |
|---|---|
| MyD88#1(S) 5' GGCGGCCGACUGGACC 3' | 3 |
| MyD88#1(AS) 5' GGUCCAGUCGGCCGCCACC 3' | 4 |
| MyD88#2(S) 5' UGGCGGCCGACUGGAC 3' | 5 |
| MyD88#2(AS) 5' GUCCAGUCGGCCGCCACCU 3' | 6 |
| MyD88#3(S) 5' GUGGCGGCCGACUGGA 3' | 7 |
| MyD88#3(AS) 5' UCCAGUCGGCCGCCACCUG 3' | 8 |
| MyD88#4(S) 5' CUGGCGGAGGAGAUGG 3' | 9 |
| MyD88#4(AS) 5' CCAUCUCCUCCGCCAGCGC 3' | 10 |
| MyD88#5(S) 5' GCUGGCGGAGGAGAUG 3' | 11 |
| MyD88#5(AS) 5' CAUCUCCUCCGCCAGCGCG 3' | 12 |
| MyD88#6(S) 5' AGUACUUGGAGAUCCG 3' | 13 |
| MyD88#6(AS) 5' CGGAUCUCCAAGUACUCAA 3' | 14 |
| MyD88#7(S) 5' GAGUACUUGGAGAUCC 3' | 15 |
| MyD88#7(AS) 5' GGAUCUCCAAGUACUCAAA 3' | 16 |
| MyD88#8(S) 5' GCCUUUACAGGUGGCC 3' | 17 |
| MyD88#8(AS) 5' GGCCACCUGUAAAGGCUUC 3' | 18 |
| MyD88#9(S) 5' AGCCUUUACAGGUGGC 3' | 19 |
| MyD88#9(AS) 5' GCCACCUGUAAAGGCUUCU 3' | 20 |
| MyD88#10(S) 5' AAGCCUUUACAGGUGG 3' | 21 |
| MyD88#10(AS) 5' CCACCUGUAAAGGCUUCUC 3' | 22 |
| MyD88#11(S) 5' GAAGCCUUUACAGGUG 3' | 23 |
| MyD88#11(AS) 5' CACCUGUAAAGGCUUCUCA 3' | 24 |
| MyD88#12(S) 5' AGAAGCCUUUACAGGU 3' | 25 |

TABLE 1-continued

Nucleic acid sequences for exemplary MyD88-targeting asiRNA.

| asiRNA SEQUENCE | SEQ ID NO: |
|---|---|
| MyD88#12(AS) 5' ACCUGUAAAGGCUUCUCAG 3' | 26 |
| MyD88#13(S) 5' AGAUGAUCCGGCAACU 3' | 27 |
| MyD88#13(AS) 5' AGUUGCCGGAUCAUCUCCU 3' | 28 |
| MyD88#14(S) 5' GAGAUGAUCCGGCAAC 3' | 29 |
| MyD88#14(AS) 5' GUUGCCGGAUCAUCUCCUG 3' | 30 |
| MyD88#15(S) 5' GGAGAUGAUCCGGCAA 3' | 31 |
| MyD88#15(AS) 5' UUGCCGGAUCAUCUCCUGC 3' | 32 |
| MyD88#16(S) 5' AGGAGAUGAUCCGGCA 3' | 33 |
| MyD88#16(AS) 5' UGCCGGAUCAUCUCCUGCA 3' | 34 |
| MyD88#17(S) 5' CAGGAGAUGAUCCGGC 3' | 35 |
| MyD88#17(AS): 5' GCCGGAUCAUCUCCUGCAC 3' | 36 |
| MyD88#18(S): 5' GCAGGAGAUGAUCCGG 3' | 37 |
| MyD88#18(AS): 5' CCGGAUCAUCUCCUGCACA 3' | 38 |
| MyD88#19(S): 5' UGCAGGAGAUGAUCCG 3' | 39 |
| MyD88#19(AS): 5' CGGAUCAUCUCCUGCACAA 3' | 40 |
| MyD88#20(S): 5' GUGCAGGAGAUGAUCC 3' | 41 |
| MyD88#20(AS): 5' GGAUCAUCUCCUGCACAAA 3' | 42 |
| MyD88#21(S): 5' UGUGCAGGAGAUGAUC 3' | 43 |
| MyD88#21(AS): 5' GAUCAUCUCCUGCACAAAC 3' | 44 |
| MyD88#22(S): 5' UUGUGCAGGAGAUGAU 3' | 45 |
| MyD88#22(AS): 5' AUCAUCUCCUGCACAAACU 3' | 46 |
| MyD88#23(S): 5' UUUGUGCAGGAGAUGA 3' | 47 |
| MyD88#23(AS): 5' UCAUCUCCUGCACAAACUG 3' | 48 |
| MyD88#24(S): 5' GUUUGUGCAGGAGAUG 3' | 49 |
| MyD88#24(AS): 5' CAUCUCCUGCACAAACUGG 3' | 50 |
| MyD88#25(S): 5' AGUUUGUGCAGGAGAU 3' | 51 |
| MyD88#25(AS): 5' AUCUCCUGCACAAACUGGA 3' | 52 |
| MyD88#26(S): 5' GUGACUUCCAGACCAA 3' | 53 |
| MyD88#26(AS): 5' UUGGUCUGGAAGUCACAUU 3' | 54 |
| MyD88#27(S): 5' UGUGACUUCCAGACCA 3' | 55 |
| MyD88#27(AS): 5' UGGUCUGGAAGUCACAUUC 3' | 56 |
| MyD88#28(S): 5' AUGUGACUUCCAGACC 3' | 57 |
| MyD88#28(AS): 5' GGUCUGGAAGUCACAUUCC 3' | 58 |
| MyD88#29(S): 5' AAUGUGACUUCCAGAC 3' | 59 |
| MyD88#29(AS): 5' GUCUGGAAGUCACAUUCCU 3' | 60 |
| MyD88#30(S): 5' GAAUGUGACUUCCAGA 3' | 61 |
| MyD88#30(AS): 5' UCUGGAAGUCACAUUCCUU 3' | 62 |

TABLE 1-continued

Nucleic acid sequences for exemplary MyD88-targeting asiRNA.

| asiRNA SEQUENCE | SEQ ID NO: |
|---|---|
| MyD88#31(S): 5' GGAAUGUGACUUCCAG 3' | 63 |
| MyD88#31(AS): 5' CUGGAAGUCACAUUCCUUG 3' | 64 |
| MyD88#32(S): 5' AGGAAUGUGACUUCCA 3' | 65 |
| MyD88#32(AS): 5' UGGAAGUCACAUUCCUUGC 3' | 66 |
| MyD88#33(S): 5' AAGGAAUGUGACUUCC 3' | 67 |
| MyD88#33(AS): 5' GGAAGUCACAUUCCUUGCU 3' | 68 |
| MyD88#34(S): 5' CAAGGAAUGUGACUUC 3' | 69 |
| MyD88#34(AS): 5' GAAGUCACAUUCCUUGCUC 3' | 70 |
| MyD88#35(S): 5' GCAAGGAAUGUGACUU 3' | 71 |
| MyD88#35(AS): 5' AAGUCACAUUCCUUGCUCU 3' | 72 |
| MyD88#36(S): 5' AGCAAGGAAUGUGACU 3' | 73 |
| MyD88#36(AS): 5' AGUCACAUUCCUUGCUCUG 3' | 74 |
| MyD88#37(S): 5' GAGCAAGGAAUGUGAC 3' | 75 |
| MyD88#37(AS): 5' GUCACAUUCCUUGCUCUGC 3' | 76 |
| MyD88#38(S): 5' AGAGCAAGGAAUGUGA 3' | 77 |
| MyD88#38(AS): 5' UCACAUUCCUUGCUCUGCA 3' | 78 |
| MyD88#39(S): 5' CAGAGCAAGGAAUGUG 3' | 79 |
| MyD88#39(AS): 5' CACAUUCCUUGCUCUGCAG 3' | 80 |
| MyD88#40(S): 5' GUCCCUGCCCUGAAGA 3' | 81 |
| MyD88#40(AS): 5' UCUUCAGGGCAGGGACAAG 3' | 82 |
| MyD88#41(S): 5' UGUCCCUGCCCUGAAG 3' | 83 |
| MyD88#41(AS): 5' CUUCAGGGCAGGGACAAGG 3' | 84 |
| MyD88#42(S): 5' UUGUCCCUGCCCUGAA 3' | 85 |
| MyD88#42(AS): 5' UUCAGGGCAGGGACAAGGC 3' | 86 |
| MyD88#43(S): 5' GCACCUGUGUCUGGUC 3' | 87 |
| MyD88#43(AS): 5' GACCAGACACAGGUGCCAG 3' | 88 |
| MyD88#44(S): 5' GGCACCUGUGUCUGGU 3' | 89 |
| MyD88#44(AS): 5' ACCAGACACAGGUGCCAGG 3' | 90 |

The asiRNAs listed in Table 1 were incubated at 95° C. for 2 minutes and at 37° C. for 1 hour in 1×siRNA duplex buffer (STpharm). Proper strand annealing was confirmed via gel electrophoresis. For the screen, HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. One day prior to transfection, 2.0×10⁴ HeLa cells were seeded in 24-well plates. The HeLa cells were transfected with 0.3 nM of the asiRNAs using Lipofectamine 2000 (Invitrogen) according to the manufacturer's instructions.

The MyD88 mRNA levels in the transfected cells were measured 24 hours after transfection using real-time PCR. Specifically, total RNA were extracted using RNAiso Plus (TaKaRa), and then 500 ng of the extracted RNA was used for cDNA synthesis using the High-capacity cDNA reverse transcription kit (Applied Biosystems), according to the manufacturer's instructions. The synthesized cDNA was diluted and then quantitative real-time PCR was performed using the StepOne real-time PCR system (Applied Biosystems) according to manufacturer's instructions. Amplification of the MyD88 gene was detected using a power SYBR Premix Ex Taq (TaKaRa). GAPDH was amplified as an internal control. The following primer sequences were used:

```
Human GAPDH-forward
                                      (SEQ ID NO: 91)
5'-GAG TCA ACG GAT TTG GTC GT-3'

Human GAPDH-reverse
                                      (SEQ ID NO: 92)
5'-GAC AAG CTT CCC GTT CTC AG-3'

Human MyD88-forward
                                      (SEQ ID NO: 93)
5'-AAG TTA TTT GTT TAC AAA CAG CGA CCA-3'

Human MyD88-reverse
                                      (SEQ ID NO: 94)
5'-GGA AGA ATG GCA AAT ATC GGC T-3'
```

The level of MyD88 inhibition by each of the 44 asiRNAs is provided in FIG. 1. Three of the asiRNA sequences, asiMyD88(26), asiMyD88(27) and asiMyD88(32), were selected for use in follow-up studies.

Example 2: Inhibition of MyD88 mRNA Expression Level Using MyD88-Targeting asiRNAs Three of the asiRNA sequences, asiMyD88(26), asiMyD88(27) and asiMyD88(32), were tested for their ability to inhibit MyD88 expression at different concentrations. The asiRNAs were incubated at 95° C. for 2 minutes and at 37° C. for 1 hour in 1×siRNA duplex buffer (STpharm). Proper strand annealing was confirmed via gel electrophoresis. For the screen, HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. One day prior to transfection, 2.0×10⁴ HeLa cells were seeded in 24-well plates. The HeLa cells were transfected with asiRNAs using Lipofectamine 2000 (Invitrogen) according to the manufacturer's instructions.

Figure 2:
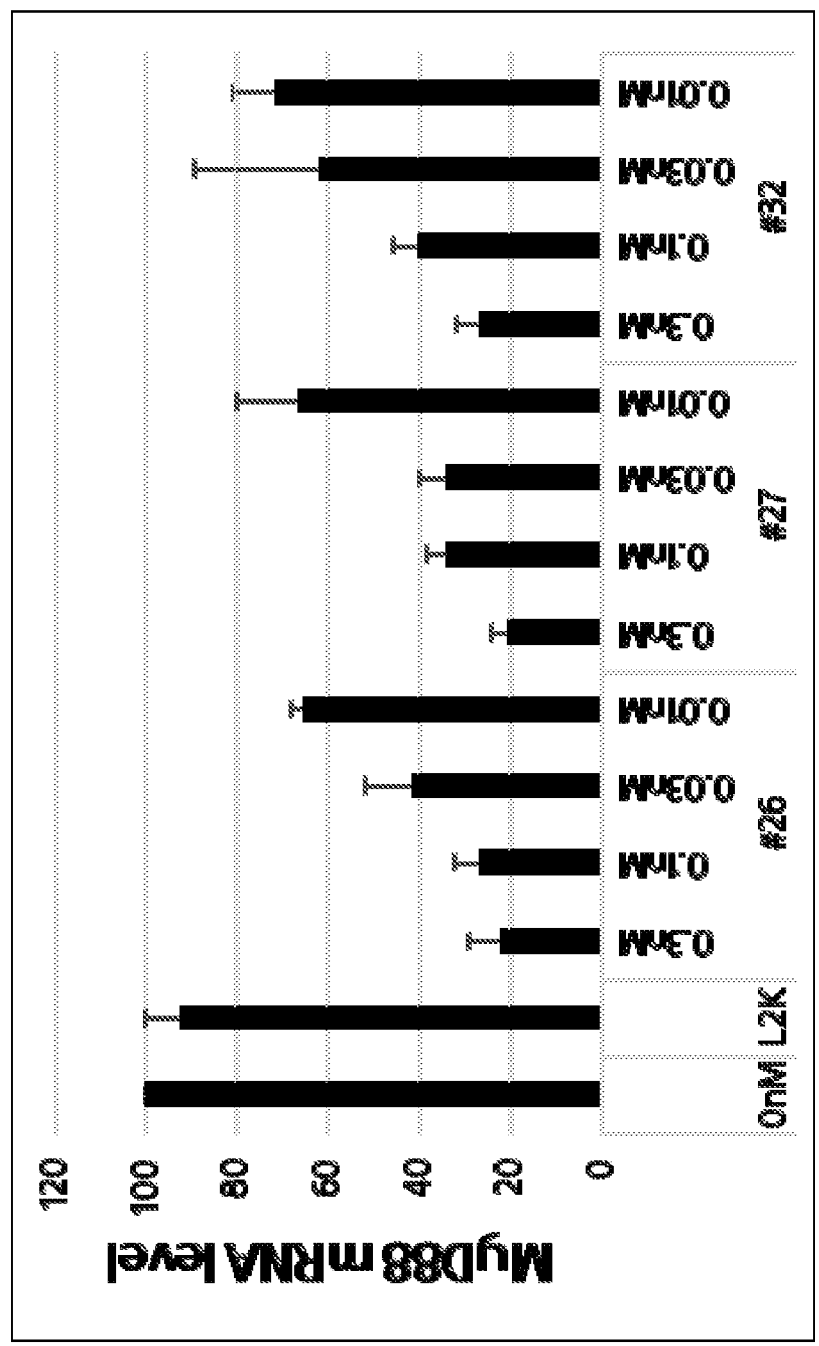
FIG. 2 shows the gene silencing efficiency of exemplary asiRNAs that target MyD88. The asiRNAs were transfected into HeLa cells at a concentration of 0.3 nM, 0.1 nM, 0.03 nM and 0.01 nM, and, after 24 hours, the degree of MyD88 mRNA expression was determined using real-time PCR. The mean and standard deviation of three repeat experiments are depicted.

The level of MyD88 inhibition by the different concentrations of the 3 asiRNAs is provided in FIG. 2. As seen in FIG. 2, low concentration of asiMyD88(26) and asiMyD88(27) exhibited the highest levels of MyD88 inhibition. asiMyD88(26) and asiMyD88(27) were selected for use in follow-up studies.

Example 3: Modification of asiRNAs

A variety of potential asiMyD88 structures having different antisense strand lengths were synthesized and tested for their ability to inhibit MyD88 expression. (Table 2)

TABLE 2

Additional asiRNA sequences.

MyD88#26(S):
5' GUGACUUCCAGACCAA 3' (SEQ ID NO: 53)

MyD88#26(19AS):
5' UUGGUCUGGAAGUCACAUU 3' (SEQ ID NO: 54)

TABLE 2-continued

Additional asiRNA sequences.

MyD88#26(21AS):
5' UUGGUCUGGAAGUCACAUUCC 3' (SEQ ID NO: 95)

MyD88#26(31AS):
5' UUGGUCUGGAAGUCACAUUCCUUGCUCUGCA 3'
(SEQ ID NO: 96)

MyD88#27(S):
5' UGUGACUUCCAGACCA 3' (SEQ ID NO: 97)

MyD88#27(19AS):
5' UGGUCUGGAAGUCACAUUC 3' (SEQ ID NO: 56)

MyD88#27(21AS):
5' UGGUCUGGAAGUCACAUUCCU 3' (SEQ ID NO: 98)

MyD88#27(31AS):
5' UGGUCUGGAAGUCACAUUCCUUGCUCUGCAG 3'
(SEQ ID NO: 99)

The asiRNAs listed in Table 2 were incubated at 95° C. for 2 minutes and at 37° C. for 1 hour in 1×siRNA duplex buffer (STpharm). Proper strand annealing was confirmed via gel electrophoresis. For the screen, HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, 2.0×10⁴ HeLa cells were seeded in 24-well plates. The HeLa cells were transfected with 0.3 nM of the asiRNAs using Lipofectamine 2000 (Invitrogen) according to the manufacturer's instructions.

The MyD88 mRNA levels in the transfected cells were measured 24 hours after transfection using real-time RT-PCR. Specifically, total RNA were extracted using RNAiso Plus(TaKaRa), and then 500 ng of the extracted RNA was used for cDNA synthesis using the High-capacity cDNA reverse transcription kit (Applied Biosystems), according to the manufacturer's instructions. The synthesized cDNA was diluted and then quantitative real-time PCR was performed using the StepOne real-time PCR system (Applied Biosystems) according to manufacturer's instructions. Amplification of the MyD88 gene was detected using a power SYBR Premix Ex Taq (TaKaRa). GAPDH was amplified as an internal control.

Figure 3:
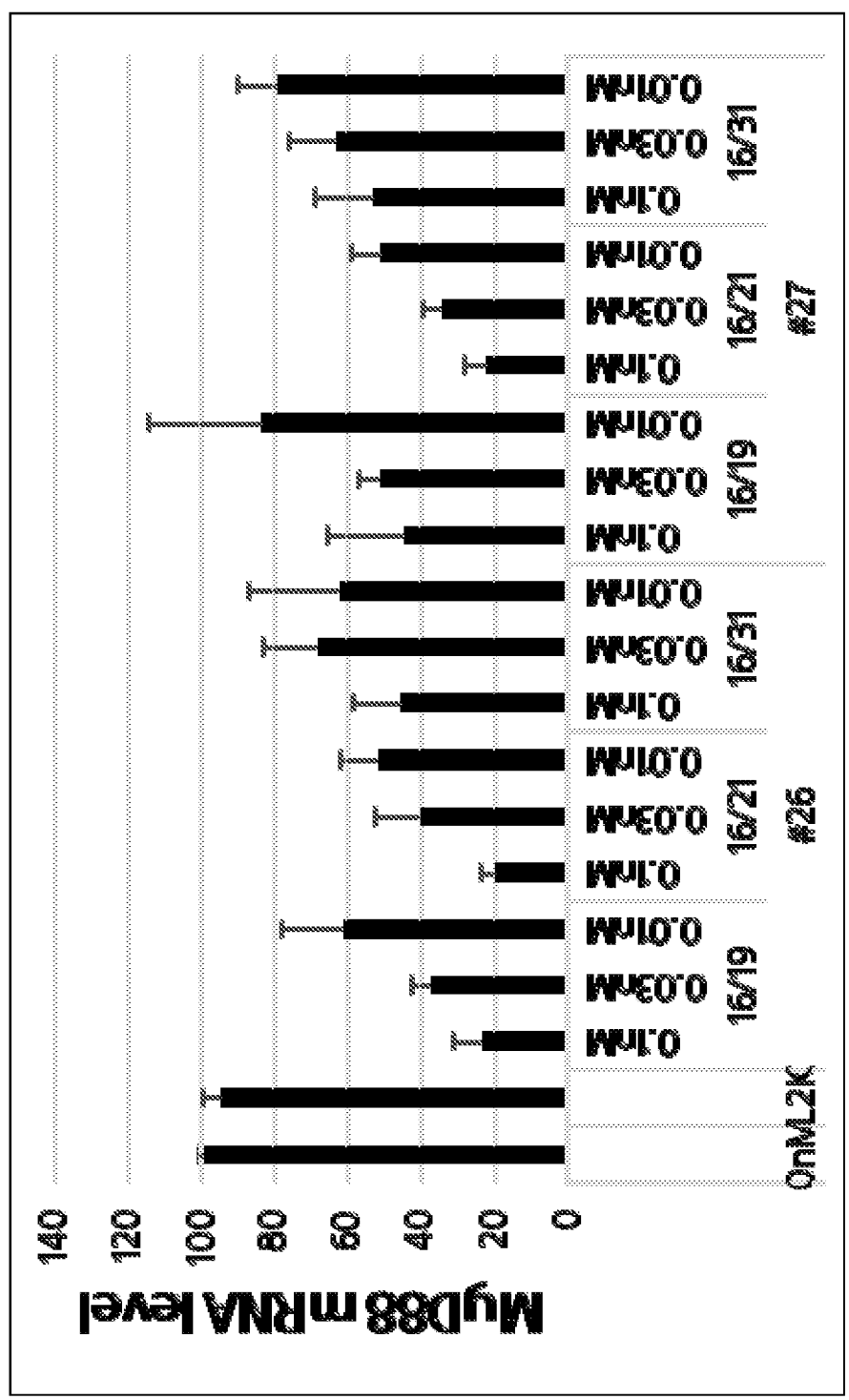
FIG. 3 shows the gene silencing effect of exemplary asiRNAs having different antisense strand lengths (19, 21 or 31 nucleotides) that target MyD88. The asiRNAs were transfected into HeLa cells at a concentration of 0.1 nM, 0.03 nM or 0.01 nM, and, after 24 hours, the degree of MyD88 mRNA expression was determined using real-time PCR. The mean and standard deviation of three repeat experiments are depicted.

The level of MyD88 inhibition by each of the 6 asiRNAs is provided in FIG. 3. 21 nucleotide antisense of asiMyD88 (26) and asiMyD88(27) exhibited the highest levels of MyD88 inhibition. 21 nucleotide antisense were selected for use in follow-up studies.

Example 4: Inhibition of MyD88 Protein Using MyD88-Specific asiRNAs

The efficacy of asiMyD88 for the inhibition of MyD88 protein was tested.

The asiRNAs were incubated at 95° C. for 2 minutes and at 37° C. for 1 hour in 1×siRNA duplex buffer (STpharm). Proper strand annealing was confirmed via gel electrophoresis.

A549 cells (ATCC) and HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, 5.0×10⁴ A549 cells or HeLa cells were seeded in 12-well plates. A549 cells and HeLa cells were transfected with 10 nM and 3 nM of the asiRNAs using Lipofectamine™ RNAiMAX (Invitrogen) according to the manufacturer's instructions. After 24 hours, OPTI-MEM media was replaced with a serum-containing media.

After 48 hours of asiRNA transfection, the level of MyD88 protein expression was determined via western blot. Briefly, the transfected A549 cells and HeLa cells were lysed with RIPA buffer (GE). 15 µg of the total protein extract of A549 cells or 30 µg of the total protein extract of HeLa cells were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and β-actin bands were then imaged using a Chemidoc instrument (Bio-rad).

Figure 4:
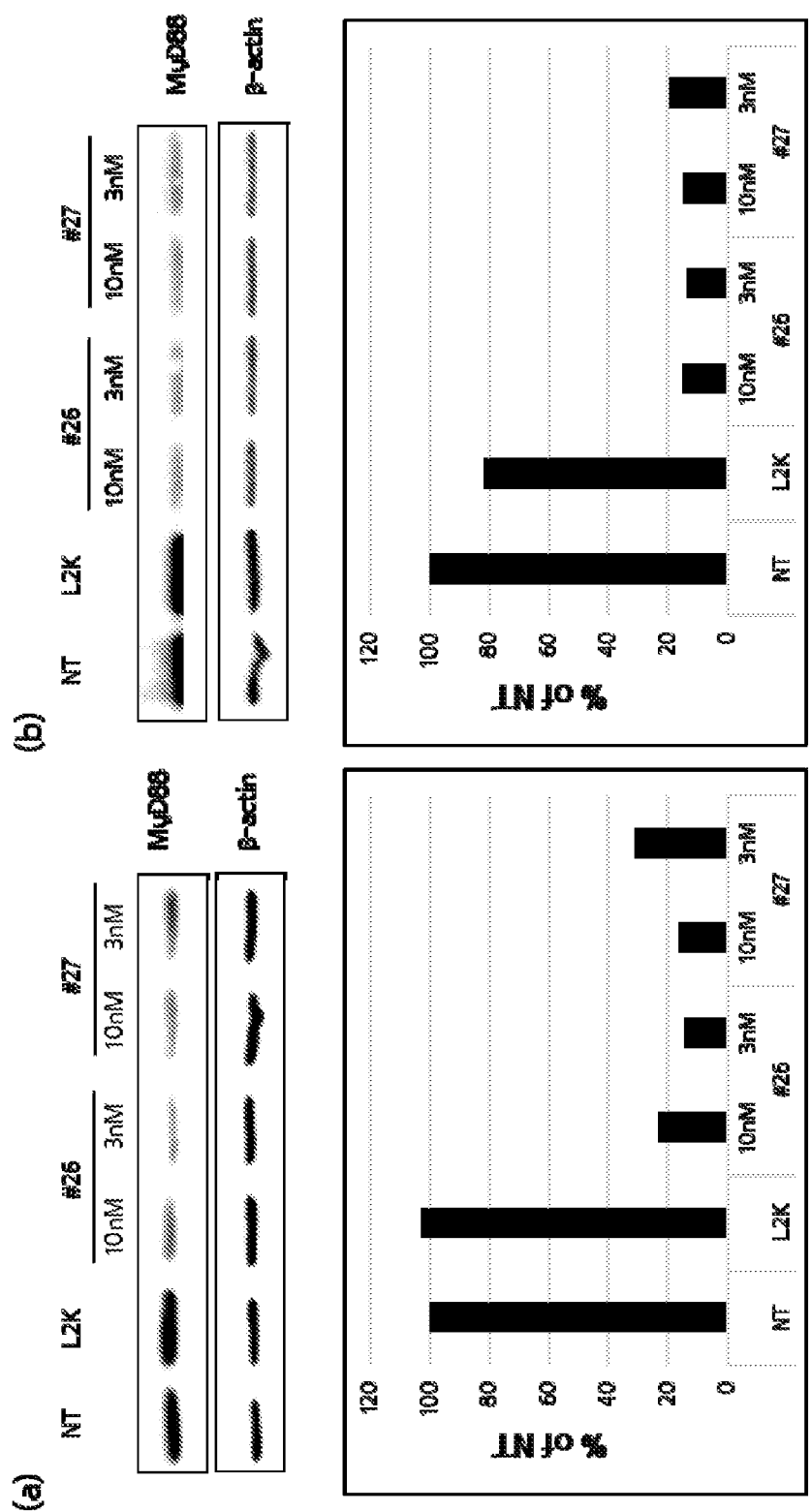
FIG. 4 shows the inhibition of MyD88 protein expression by exemplary asiRNAs that target MyD88. The asiRNAs were transfected into A549 or HeLa cells at a concentration of 3 nM or 10 nM, and, after 48 hours, protein was extracted and a western blot performed. Panel (a) depicts the MyD88 protein expression level in A549 cells 48 hours after transfection. Panel (b) depicts the MyD88 protein expression level in in HeLa cells 48 hours after transfection. (NT=no treatment, L2K=transfection control).

The results of the western blot assay are depicted in FIG. 4. In all asiMyD88 transfection cell lines of A549 cells and HeLa cells, 80% or more of MyD88 protein inhibition were confirmed. (FIG. 4).

Example 5: Chemical Modification of MyD88 asiRNAs

Chemical modifications were applied to the asiRNAs. As described below, certain of the modifications improved endocytosis and stability of the asiRNAs. Four asiRNAs (Table 3) were tested for MyD88 mRNA inhibition in HeLa cells

TABLE 3

Modified asiRNA sequences.

MyD88#26(16S-1):
5' mGUmGAmCUmUCmCAmGAmCCmAA 3' (SEQ ID NO: 100)

MyD88#26(19AS-1):
5' UUGGUCUGGAAGUCmAmCmAmUmU 3' (SEQ ID NO: 101)

MyD88#26(21AS-1):
5' UUGGUCUGGAAGUCmAmCmAmUmUmCmC 3'
(SEQ ID NO: 102)

MyD88#27(16S-1):
5' mUGmUGmACmUUmCCmAGmACmCA 3' (SEQ ID NO: 103)

MyD88#27(19AS-1):
5' UGGUCUGGAAGUCAmCmAmUmUmC 3' (SEQ ID NO: 104)

MyD88#27(21AS-1):
5' UGGUCUGGAAGUCAmCmAmUmUmCmCmU 3'
(SEQ ID NO: 105)

m = 2'-O-Methyl RNA

HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, 2.0×10⁴ HeLa cells were seeded in 24-well plates. The HeLa cells were transfected using Lipofectamine 2000 (Invitrogen) according to the manufacturer's instructions. Twenty-four hours later, MyD88 mRNA levels were in the HeLa cells were determined.

Figure 5:
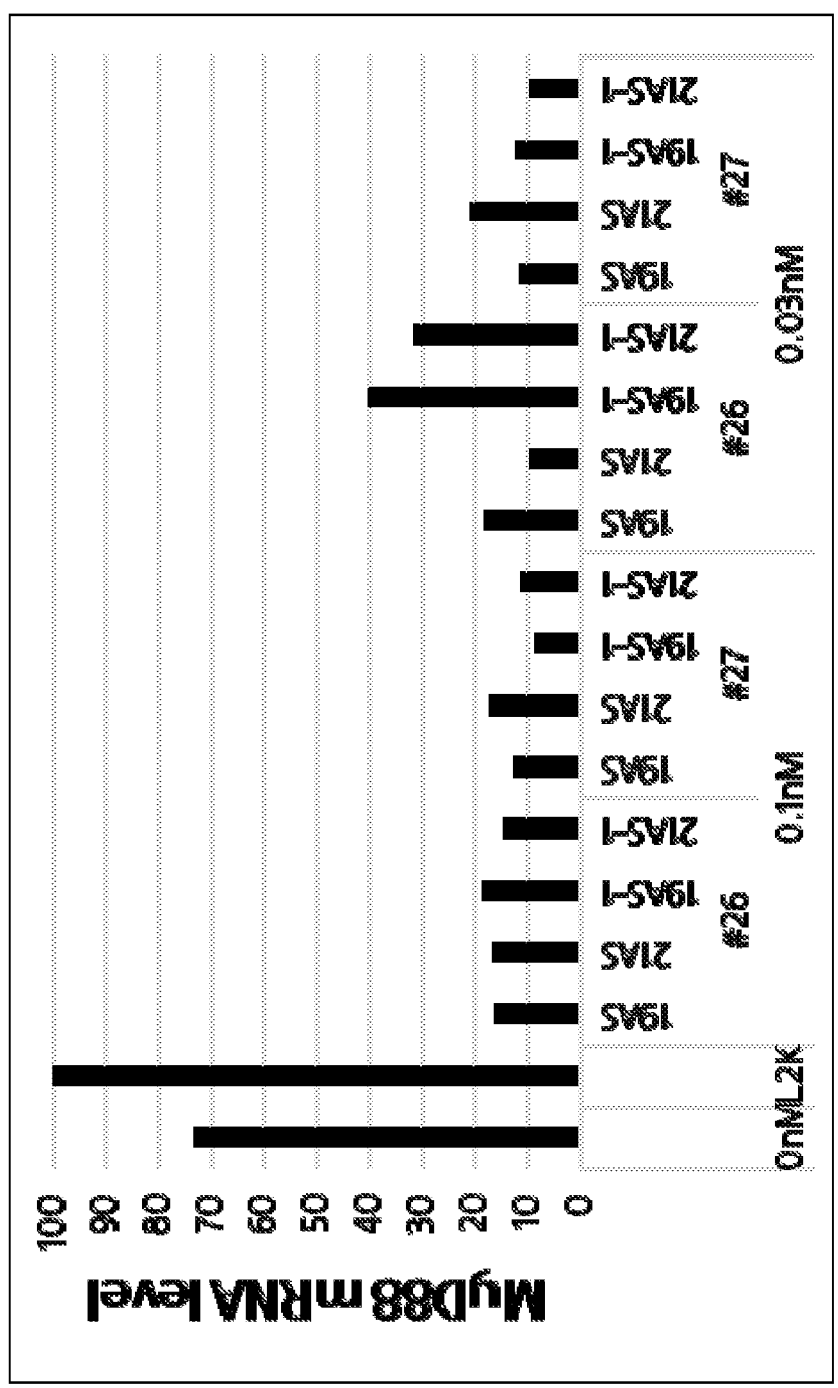
FIG. 5 shows the gene silencing efficiency of exemplary asiRNAs containing 2'-0-Methylation modifications. The asiRNAs were transfected into HeLa cells at a concentration of 0.1 nM or 0.03 nM, and, after 24 hours, the degree of MyD88 mRNA expression was determined using real-time PCR.

The level of MyD88 inhibition by each of the asiRNAs in provided in FIG. 5. Modified MyD88(27) exhibited the highest levels of MyD88 inhibition.

Example 6: Chemical Modification of asiRNAs for Self-Delivery

Chemical modifications were applied to the asiRNAs and the cellular delivery of the modified asiRNAs was tested in the absence of other delivery vehicle. As described below, certain of the modifications improved endocytosis and stability of the asiRNAs. Such cell penetrating asiRNAs (cp-asiRNAs) are able to be delivered into the cell in the absence of a delivery vehicle.

Twenty potential cp-asiRNAs (Table 4) were screened for MyD88 mRNA inhibition in HeLa cells. Each potential cp-asiRNA was incubated with HeLa cells at 1 µM without a delivery vehicle and MyD88 mRNA levels were measured by Real-Time PCR.

TABLE 4

Modified asiRNA sequences tested for self-delivery and MyD88 inhibition.

| | |
|---|---|
| cp-asiMyD88#26-1(S): 5' GUGACUUCCAGACC*A*A*cholesterol 3' | (SEQ ID NO: 106) |
| cp-asiMyD88#26-1(AS): 5' UUGGUCUGGAAGUCACA*U*U*C*C 3' | (SEQ ID NO: 107) |
| cp-asiMyD88#26-2(S): 5' GUGACUUCCAGACC*A*A*cholesterol 3' | (SEQ ID NO: 108) |
| cp-asiMyD88#26-2(AS): 5' UUGGUCUGGAAGUCACA*U*mU*mC*mC 3' | (SEQ ID NO: 109) |
| cp-asiMyD88#26-3(S): 5' GUGACUUCCAGACC*A*A*cholesterol 3' | (SEQ ID NO: 110) |
| cp-asiMyD88#26-3(AS): 5' UUGGUCUGGAAGUCACmA*mU*mU*mC*mC 3' | (SEQ ID NO: 111) |
| cp-asiMyD88#26-4(S): 5' GUGACUUCCAGACC*A*A*cholesterol 3' | (SEQ ID NO: 112) |
| cp-asiMyD88#26-4(AS): 5' UUGGUCUGGAAGUCmAmCmA*mU*U*C*C 3' | (SEQ ID NO: 113) |
| cp-asiMyD88#26-5(S): 5' GUGACUUCCAGACC*A*A*cholesterol 3' | (SEQ ID NO: 114) |
| cp-asiMyD88#26-5(AS): 5' UUGGUCUGGAAGUCmAmCA*U*U*C*C 3' | (SEQ ID NO: 115) |
| cp-asiMyD88#26-6(S): 5' mGUmGAmCUmUCmCAmGAmCC*mA*A*cholesterol 3' | (SEQ ID NO: 116) |
| cp-asiMyD88#26-6(AS): 5' UUGGUCUGGAAGUCACA*U*U*C*C 3' | (SEQ ID NO: 117) |
| cp-asiMyD88#26-7(S): 5' mGUmGAmCUmUCmCAmGAmCC*mA*A*cholesterol 3' | (SEQ ID NO: 118) |
| cp-asiMyD88#26-7(AS): 5' UUGGUCUGGAAGUCACA*U*mU*mC*mC 3' | (SEQ ID NO: 119) |
| cp-asiMyD88#26-8(S): 5' mGUmGAmCUmUCmCAmGAmCC*mA*A*cholesterol 3' | (SEQ ID NO: 120) |
| cp-asiMyD88#26-8(AS): 5' UUGGUCUGGAAGUCACmA*mU*mU*mC*mC 3' | (SEQ ID NO: 121) |
| cp-asiMyD88#26-9(S): 5' mGUmGAmCUmUCmCAmGAmCC*mA*A*cholesterol 3' | (SEQ ID NO: 122) |
| cp-asiMyD88#26-9(AS): 5' UUGGUCUGGAAGUCmAmCmA*mU*U*C*C 3' | (SEQ ID NO: 123) |
| cp-asiMyD88#26-10(S): 5' mGUmGAmCUmUCmCAmGAmCC*mA*A*cholesterol 3' | (SEQ ID NO: 124) |
| cp-asiMyD88#26-10(AS): 5' UUGGUCUGGAAGUCmAmCA*U*U*C*C 3' | (SEQ ID NO: 125) |
| cp-asiMyD88#27-1(S): 5' UGUGACUUCCAGAC*C*A*cholesterol 3' | (SEQ ID NO: 126) |
| cp-asiMyD88#27-1(AS): 5' UGGUCUGGAAGUCACAU*U*C*C*U 3' | (SEQ ID NO: 127) |
| cp-asiMyD88#27-2(S): 5' UGUGACUUCCAGAC*C*A*cholesterol 3' | (SEQ ID NO: 128) |
| cp-asiMyD88#27-2(AS): 5' UGGUCUGGAAGUCACAU*U*mC*mC*mU 3' | (SEQ ID NO: 129) |
| cp-asiMyD88#27-3(S): 5' UGUGACUUCCAGAC*C*A*cholesterol 3' | (SEQ ID NO: 130) |
| cp-asiMyD88#27-3(AS): 5' UGGUCUGGAAGUCACAmU*mU*mC*mC*mU 3' | (SEQ ID NO: 131) |
| cp-asiMyD88#27-4(S): 5' UGUGACUUCCAGAC*C*A*cholesterol 3' | (SEQ ID NO: 132) |
| cp-asiMyD88#27-4(AS): 5' UGGUCUGGAAGUCAmCmAmU*mU*C*C*U 3' | (SEQ ID NO: 133) |
| cp-asiMyD88#27-5(S): 5' UGUGACUUCCAGAC*C*A*cholesterol 3' | (SEQ ID NO: 134) |
| cp-asiMyD88#27-5(AS): 5' UGGUCUGGAAGUCAmCmAU*U*C*C*U 3' | (SEQ ID NO: 135) |
| cp-asiMyD88#27-6(S): 5' mUGmUGmACmUUmCCmAGmAC*mC*A*cholesterol 3' | (SEQ ID NO: 136) |

TABLE 4-continued

Modified asiRNA sequences tested for
self-delivery and MyD88 inhibition.

| | | |
|---|---|---|
| cp-asiMyD88#27-6(AS): | 5' UGGUCUGGAAGUCACAU*U*C*C*U 3' | (SEQ ID NO: 137) |
| cp-asiMyD88#27-7(S): | 5' mUGmUGmACmUUmCCmAGmAC*mC*A*cholesterol 3' | (SEQ ID NO: 138) |
| cp-asiMyD88#27-7(AS): | 5' UGGUCUGGAAGUCACAU*U*mC*mC*mU 3' | (SEQ ID NO: 139) |
| cp-asiMyD88#27-8(S): | 5' mUGmUGmACmUUmCCmAGmAC*mC*A*cholesterol 3' | (SEQ ID NO: 140) |
| cp-asiMyD88#27-8(AS): | 5' UGGUCUGGAAGUCACAmU*mU*mC*mC*mU 3' | (SEQ ID NO: 141) |
| cp-asiMyD88#27-9(S): | 5' mUGmUGmACmUUmCCmAGmAC*mC*A*cholesterol 3' | (SEQ ID NO: 142) |
| cp-asiMyD88#27-9(AS): | 5' UGGUCUGGAAGUCAmCmAmU*mU*C*C*U 3' | (SEQ ID NO: 143) |
| cp-asiMyD88#27-10(S): | 5' mUGmUGmACmUUmCCmAGmAC*mC*A* cholesterol 3' | (SEQ ID NO: 144) |
| cp-asiMyD88#27-10(AS): | 5' UGGUCUGGAAGUCAmCmAU*U*C*C*U 3' | (SEQ ID NO: 145) | m = 2'-O-Methyl RNA,
* = phosphorothioate bond.

HeLa cells (ATCC) that had been cultured in Dulbecco's modified Eagle's medium (Gibco) containing 10% fetal bovine serum (Gibco) and 100 μg/ml penicillin/streptomycin in a 100 mm cell culture dish.

The potential cp-asiRNAs listed in Table 4 were incubated at 95° C. for 2 minutes and at 37° C. for 1 hour in OPTI-MEM buffer (Gibco). Proper strand annealing was confirmed via gel electrophoresis.

One day prior to transfection, 2.0×10⁴ HeLa cells were seeded in 24-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media.

After 48 hours of asiRNA treatment, the level of MyD88 mRNA expression was determined.

Figure 6:
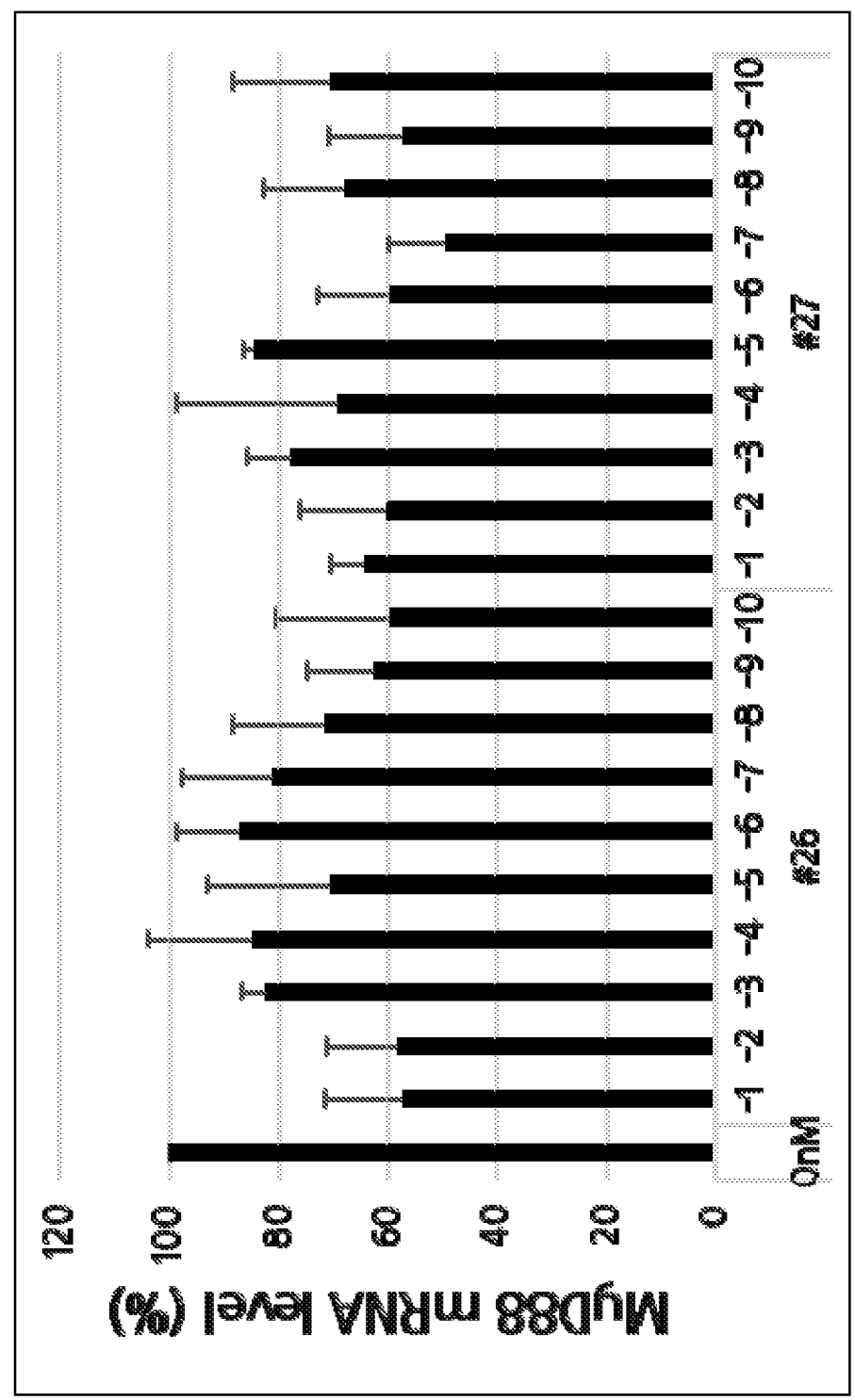
FIG. 6 shows the gene silencing efficiency of exemplary MyD88-targeting cell penetrating asiRNAs (cp-asiRNAs, or cp-asiMyD88s) to which various chemical modifications have been applied. The cp-asiRNAs were incubated without transfection vehicle in the presence of HeLa cells at a concentration of 1 µM and, after 48 hours, the degree of MyD88 mRNA expression was determined using real-time PCR. The mean and standard deviation of three repeat experiments are depicted.

The level of MyD88 inhibition by each of the 20 potential cp-asiRNAs is provided FIG. 6. Of the potential cp-asiRNAs tested, cp-asiRNA(26)-1 and cp-asiRNA(27)-7 exhibited the highest levels of MyD88 inhibition.

Example 7: Inhibition of MyD88 Protein Using MyD88-Specific Cp-asiRNAs

The efficacy of cp-asiRNAs for the inhibition of MyD88 protein was tested. Each potential cp-asiRNA was incubated with HeLa cells at 1 μM without a delivery vehicle and MyD88 protein levels were measured by western blot.

HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. The cp-asiRNAs were incubated at 95° C. for 2 minutes and at 37° C. for 1 hour in OPTI-MEM buffer (Gibco). Proper strand annealing was confirmed via gel electrophoresis. One day prior to transfection, 5.0×10⁴ HeLa cells were seeded in 12-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media.

After 48 hours of asiRNA treatment, the level of MyD88 protein expression was determined via western blot. Briefly, the treated HeLa cells were lysed with RIPA buffer (GE). 30 μg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-γ-tubulin (Bethyl). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and γ-tubulin bands were then imaged using a Chemidoc instrument (Bio-rad).

Figure 7:
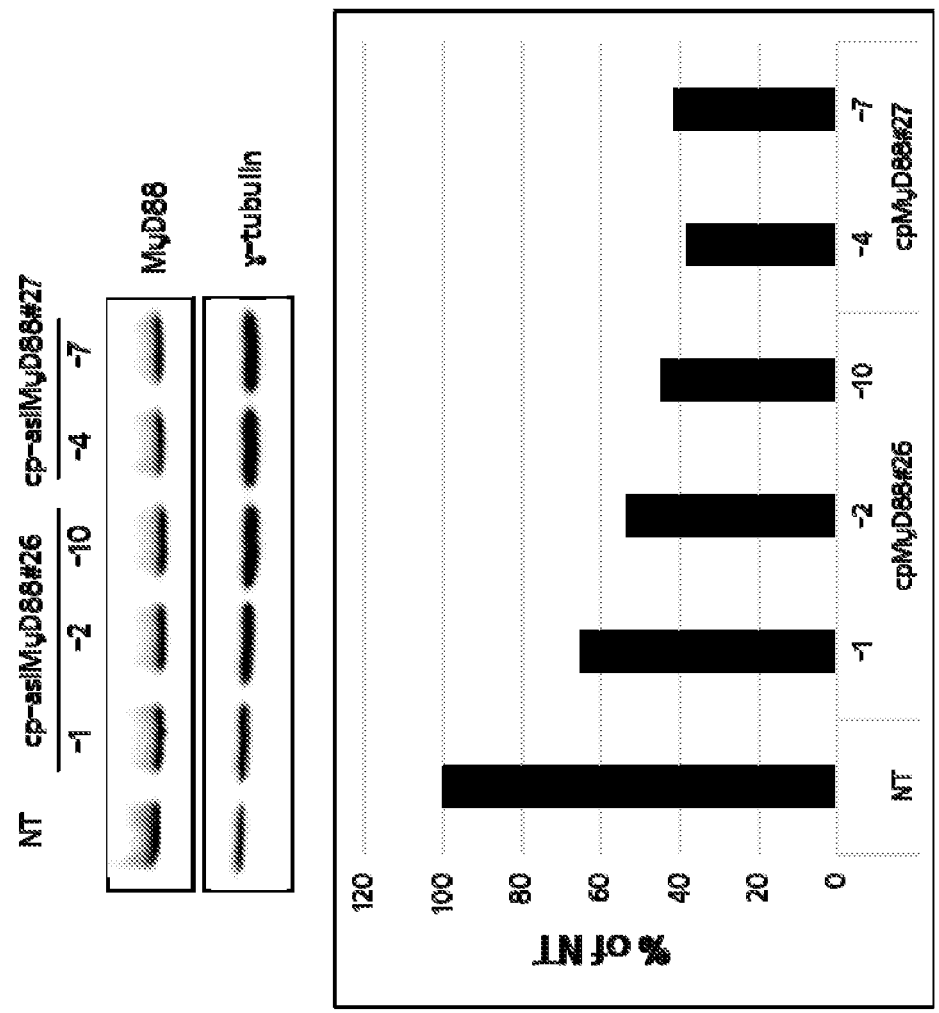
FIG. 7 shows the inhibition of MyD88 protein expression by exemplary cp-asiRNAs. The cp-asiRNAs were contacted to HeLa cells without transfection vehicle and, after 48 hours, protein was extracted and a western blot performed. (NT=no treatment).

The results of the western blot assay are depicted in FIG. 7. All cp-asiMyD88(27)-4 and cp-asiMyD88(27)-7 incubated cell lines exhibited 60% or more of MyD88 protein inhibition (FIG. 7).

Example 8: Inhibition of MyD88 Protein Using MyD88-Specific Cp-asiRNAs

A variety of potential cp-asiMyD88 structures having different number of phosphorothioate bond in antisense strand were synthesized and tested for their ability to inhibit MyD88 expression (Table 5).

TABLE 5

Additional cp-asiRNA sequences.

| | | |
|---|---|---|
| cp-asiMyD88#26-11(S): | 5' GUGACUUCCAGACC*A*A*cholesterol 3' | (SEQ ID NO: 146) |
| cp-asiMyD88#26-11(AS): | 5' UUGGUCUGGAAGUCA*C*A*U*U*C*C 3' | (SEQ ID NO: 147) |

TABLE 5-continued

Additional cp-asiRNA sequences.

```
cp-asiMyD88#26-12(S):   5' GUGACUUCCAGACC*A*A*cholesterol 3'      (SEQ ID NO: 148)

cp-asiMyD88#26-12(AS):  5' UUGGUCUGGAAGUCA*C*mA*mU*mU*mC*mC 3'    (SEQ ID NO: 149)

cp-asiMyD88#26-13(S):   5' GUGACUUCCAGACC*A*A*cholesterol 3'      (SEQ ID NO: 150)

cp-asiMyD88#26-13(AS):  5' UUGGUCUGGAAGUCmA*mC*mA*mU*U*C*C 3'     (SEQ ID NO: 151)

cp-asiMyD88#26-14(S):   5' GUGACUUCCAGACC*A*A*cholesterol 3'      (SEQ ID NO: 152)

cp-asiMyD88#26-14(AS):  5' UUGGUCUGGAAGUCmA*mC*A*U*U*C*C 3'       (SEQ ID NO: 153)

cp-asiMyD88#26-15(S):   5' mGUmGAmCUmUCmCAmGAmCC*mA*A*
                           cholesterol 3'                         (SEQ ID NO: 154)

cp-asiMyD88#26-15(AS):  5' UUGGUCUGGAAGUCA*C*A*U*U*C*C 3'         (SEQ ID NO: 155)

cp-asiMyD88#26-16(S):   5' mGUmGAmCUmUCmCAmGAmCC*mA*A*
                           cholesterol 3'                         (SEQ ID NO: 156)

cp-asiMyD88#26-16(AS):  5' UUGGUCUGGAAGUCA*C*mA*mU*mU*mC*mC 3'    (SEQ ID NO: 157)

cp-asiMyD88#26-17(S):   5' mGUmGAmCUmUCmCAmGAmCC*mA*A*
                           cholesterol 3'                         (SEQ ID NO: 158)

cp-asiMyD88#26-17(AS):  5' UUGGUCUGGAAGUCmA*mC*mA*mU*U*C*C 3'     (SEQ ID NO: 159)

cp-asiMyD88#26-18(S):   5' mGUmGAmCUmUCmCAmGAmCC*mA*A*
                           cholesterol 3'                         (SEQ ID NO: 160)

cp-asiMyD88#26-18(AS):  5' UUGGUCUGGAAGUCmA*mC*A*U*U*C*C 3'       (SEQ ID NO: 161)

cp-asiMyD88#27-11(S):   5' UGUGACUUCCAGAC*C*A*cholesterol 3'      (SEQ ID NO: 162)

cp-asiMyD88#27-11(AS):  5' UGGUCUGGAAGUCAC*A*U*U*C*C*U 3'         (SEQ ID NO: 163)

cp-asiMyD88#27-12(S):   5' UGUGACUUCCAGAC*C*A*cholesterol 3'      (SEQ ID NO: 164)

cp-asiMyD88#27-12(AS):  5' UGGUCUGGAAGUCAmC*mA*mU*mU*C*C*U 3'     (SEQ ID NO: 165)

cp-asiMyD88#27-13(S):   5' mUGmUGmACmUUmCCmAGmAC*mC*A*
                           cholesterol 3'                         (SEQ ID NO: 166)

cp-asiMyD88#27-13(AS):  5' UGGUCUGGAAGUCAC*A*U*U*mC*mC*mU 3'      (SEQ ID NO: 167)

cp-asiMyD88#27-14(S):   5' mUGmUGmACmUUmCCmAGmAC*mC*A*
                           cholesterol 3'                         (SEQ ID NO: 168)

cp-asiMyD88#27-14(AS):  5' UGGUCUGGAAGUCAmC*mA*mU*mU*C*C*U 3'     (SEQ ID NO: 169)
``` m = 2'-O-Methyl RNA,
* = phosphorothioate bond.

The ability of 1 µM of each of the potential cp-asiRNAs listed in Table 5 to inhibit MyD88 mRNA in HeLa cells was tested. HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. The potential cp-asiRNAs listed in Table 5 were incubated at 95° C. for 2 minutes and at 37° C. for 1 hour in OPTI-MEM buffer (Gibco). Proper strand annealing was confirmed via gel electrophoresis. One day prior to transfection, 2.0×10⁴ HeLa cells were seeded in 24-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media. After 48 hours of asiRNA treatment, the level of MyD88 mRNA expression was determined.

Figure 8:
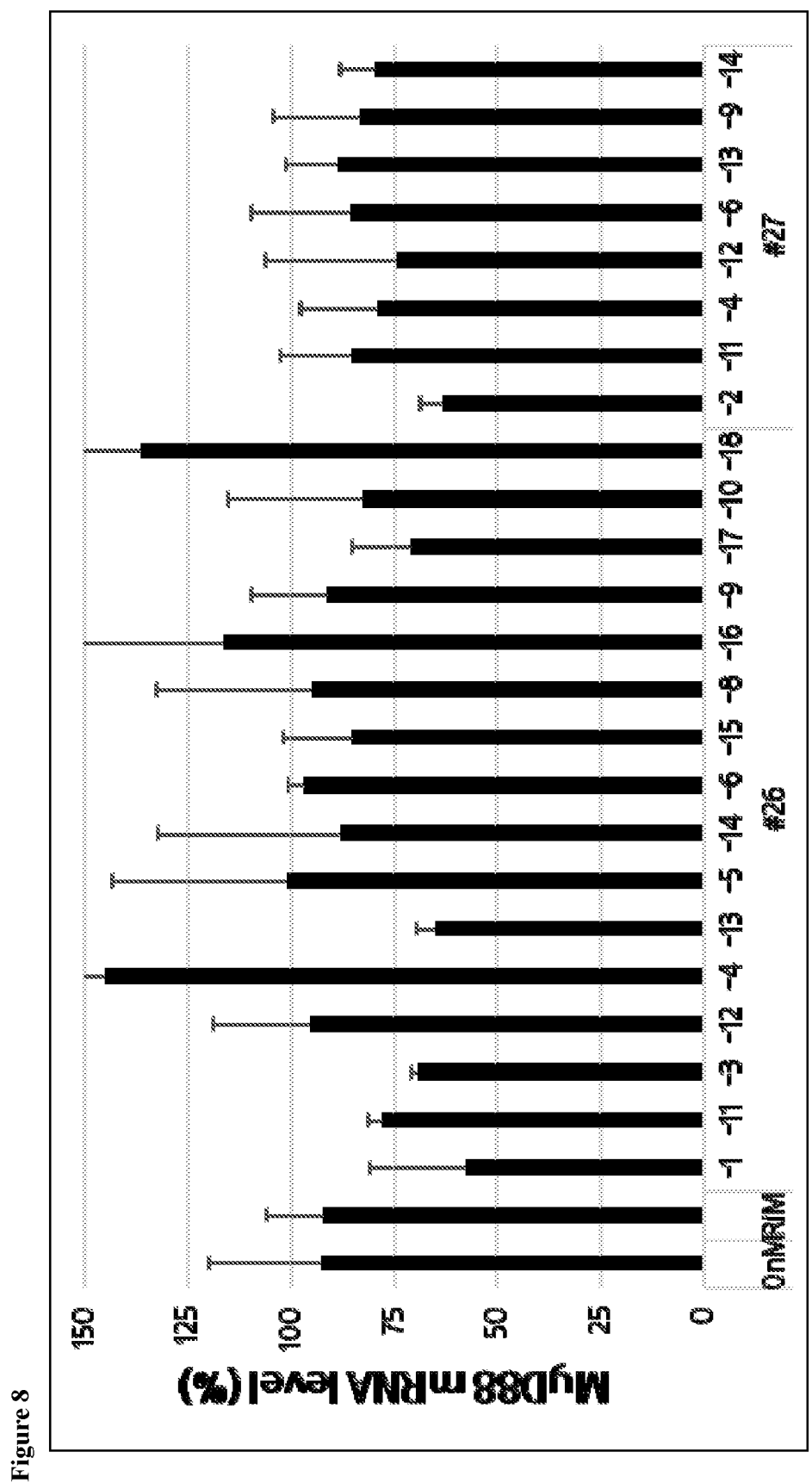
FIG. 8 shows the gene silencing efficiency of exemplary cp-asiRNAs to which various chemical modifications have been applied. The cp-asiRNAs were incubated without transfection vehicle in the presence of HeLa cells at a concentration of 1 µM and, after 48 hours, the degree of MyD88 mRNA expression was determined using real-time PCR. The mean and standard deviation of three repeat experiments are depicted.

As seen in FIG. 8, MyD88 mRNA potential cp-asiRNA (26) containing 3 phosphorothioate bond on sense strand and 4 phosphorothioate bond on antisense strand, cp-asiRNA (27) containing 3 phosphorothioate bond on sense strand and three 2'-O-Methylation and 4 phosphorothioate bond on antisense strand exhibited the highest levels of MyD88 inhibition.

Example 9: Inhibition of MyD88 Protein Using Additional MyD88-Specific Cp-asiRNAs The efficacy of cp-asiRNAs for the inhibition of MyD88 protein were tested. Each potential cp-asiRNA was incubated with HeLa cells at 3 uM without a delivery vehicle and MyD88 protein levels were measured by western blot. HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. The cp-asiRNAs were incubated at 95° C. for 2 minutes and at 37° C. for 1 hour in OPTI-MEM buffer (Gibco). Proper strand annealing was confirmed via gel electrophoresis. One day prior to transfection, 5.0×10⁴ HeLa cells were seeded in 12-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media.

After 48 hours of asiRNA treatment, the level of MyD88 protein expression was determined via western blot. Briefly, the treated HeLa cells were lysed with RIPA buffer (GE). 30 µg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-γ-tubulin (Bethyl). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and γ-tubulin bands were then imaged using a Chemidoc instrument (Bio-rad).

Figure 9:
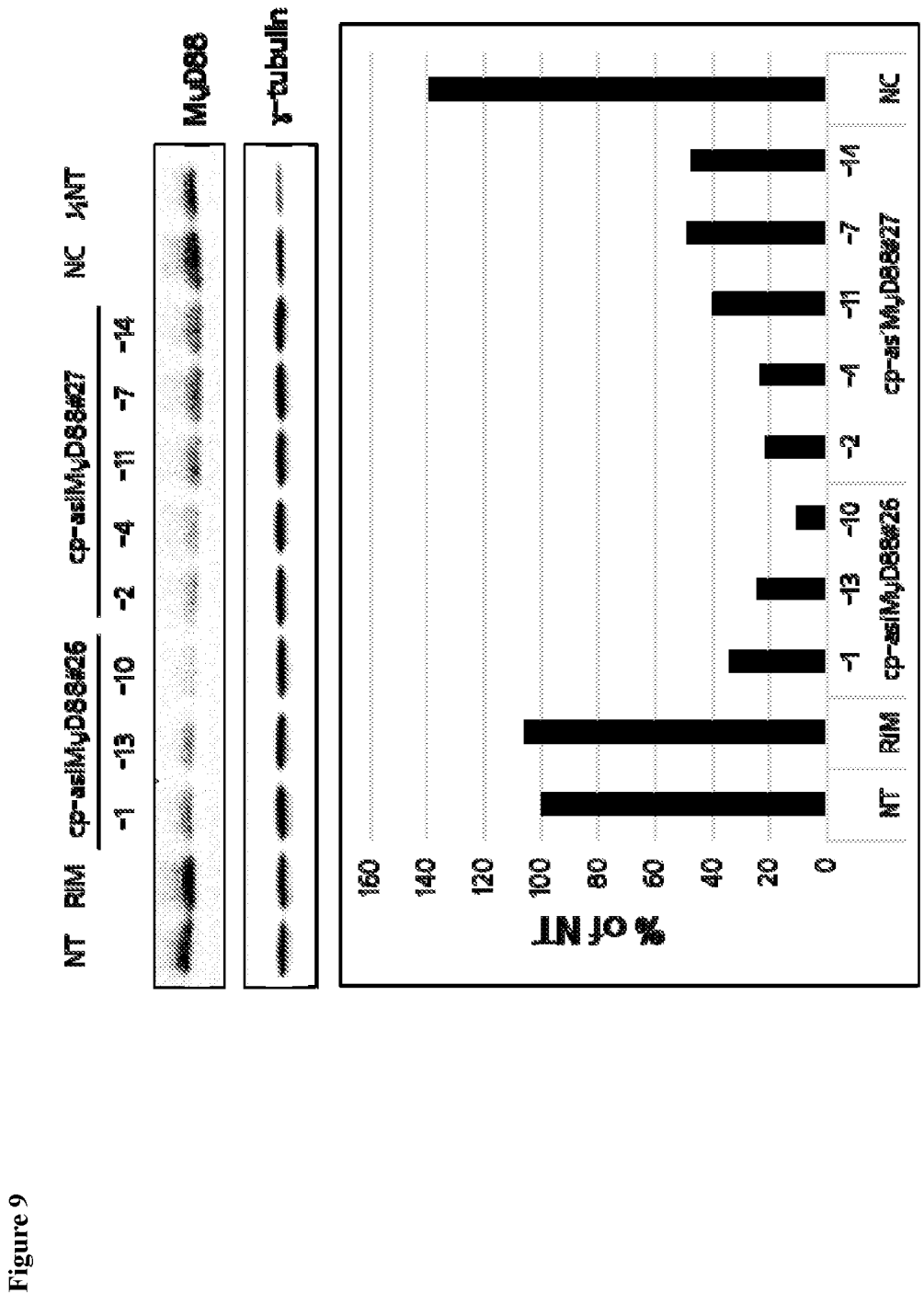
FIG. 9 shows the inhibition of MyD88 protein expression by exemplary cp-asiRNAs. The cp-asiRNAs were contacted to HeLa cells without transfection vehicle and, after 48 hours, protein was extracted and a western blot performed. (NT=no treatment, RiM=transfection reagent only, NC=negative control).

The results of the western blot assay are depicted in FIG. 9. All cp-asiMyD88 incubated cell lines exhibited 50% or more of MyD88 protein inhibition. In addition, the cp-asi-MyD88(26)-10 and cp-asiMyD88(27)-2 were shown to have a higher efficiency in the MyD88 inhibition ability than other cp-asiMD88s (FIG. 9).

Example 10: Additional MyD88 cp-asiRNA Structures

A variety of potential cp-asiMyD88 structures having different strand lengths and numbers of 2'-O-methylation modifications and phosphorothioate bonds were synthesized and tested for their ability to inhibit MyD88 expression (Table 6).

The ability of 1 µM or 3 µM of each of the potential cp-asiRNAs listed in Table 6 to inhibit MyD88 mRNA in HeLa cells was tested. HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. The potential cp-asiRNAs listed in Table 6 were incubated at 95° C. for 2 minutes and at 37° C. for 1 hour in OPTI-MEM buffer (Gibco). Proper strand annealing was confirmed via gel electrophoresis. One day prior to transfection, 2.0×10⁴ HeLa cells were seeded in 24-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media. After 48 hours of asiRNA treatment, the level of MyD88 mRNA expression was determined.

Figure 10:
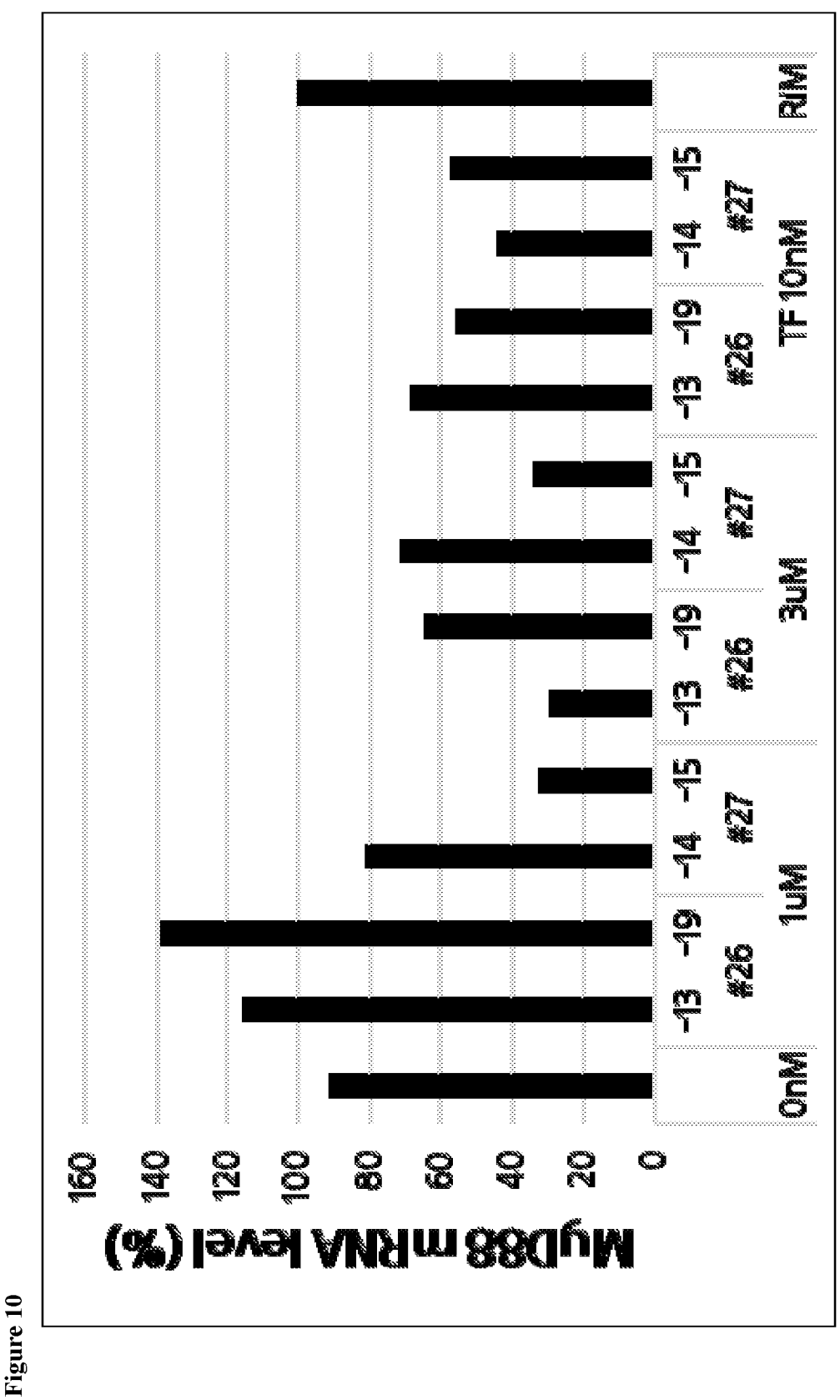
FIG. 10 shows the gene silencing efficiency of cp-asiRNAs having different antisense strand lengths (21 or 19 nucleotides) and containing 2'-O-Methylation modifications. Each cp-asiRNAs was incubated without transfection vehicle in the presence of HeLa cells at a concentration of 1 µM and, after 48 hours, the degree of MyD88 mRNA expression was determined using real-time PCR.

As seen in FIG. 10, MyD88 mRNA potential cp-asiRNA (26) containing four 2'-O-Methylation and six phosphorothioate bond on 21 nucleotide antisense strand, cp-asiRNA (27) containing four 2'-O-Methylation and six phosphorothioate bond on 19 nucleotide antisense strand exhibited the highest levels of MyD88 inhibition.

Example 11: Inhibition of MyD88 Protein Using Additional MyD88-Specific Cp-asiRNAs The efficacy of cp-asiRNAs for the inhibition of MyD88 protein were tested. Each potential cp-asiRNA was incubated with HeLa cells at 1 µM and 3 µM without a delivery vehicle and MyD88 protein levels were measured by western blot. HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. The cp-asiRNAs were incubated at 95° C. for 2 minutes and at 37° C. for 1 hour in OPTI-MEM buffer (Gibco). Proper strand annealing was confirmed via gel electrophoresis.

TABLE 6

Additional cp-asiRNA sequences

```
cp-asiMyD88#26-13(S):
5' GUGACUUCCAGACC*A*A*cholesterol 3' (SEQ ID NO: 170)

cp-asiMyD88#26-13(AS):
5' UUGGUCUGGAAGUCmA*mC*mA*mU*U*C*C 3' (SEQ ID NO: 171)

cp-asiMyD88#26-19(S):
5' GUGACUUCCAGACC*A*A*cholesterol 3' (SEQ ID NO: 172)

cp-asiMyD88#26-19(AS):
5' UUGGUCUGGAAGU*C*mA*mC*mA*mU*U 3' (SEQ ID NO: 173)

cp-asiMyD88#27-14(S):
5' mUGmUGmACmUUmCCmAGmAC*mC*A*cholesterol 3' (SEQ ID NO: 174)

cp-asiMyD88#27-14(AS):
5' UGGUCUGGAAGUCAmC*mA*mU*mU*C*C*U 3' (SEQ ID NO: 175)

cp-asiMyD88#27-15(S):
5' mUGmUGmACmUUmCCmAGmAC*mC*A*cholesterol 3' (SEQ ID NO: 176)

cp-asiMyD88#27-15(AS):
5' UGGUCUGGAAGUC*A*mC*mA*mU*mU*C 3' (SEQ ID NO: 177)
```

(m = 2'-O-Methyl RNA,
* = phosphorothioate bond).

One day prior to transfection, 5.0×10⁴ HeLa cells were seeded in 12-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media. After 48 hours of asiRNA treatment, the level of MyD88 protein expression was determined via western blot. Briefly, the treated HeLa cells were lysed with RIPA buffer (GE). 30 μg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-γ-tubulin (Bethyl). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and γ-tubulin bands were then imaged using a Chemidoc instrument (Bio-rad).

Figure 11:
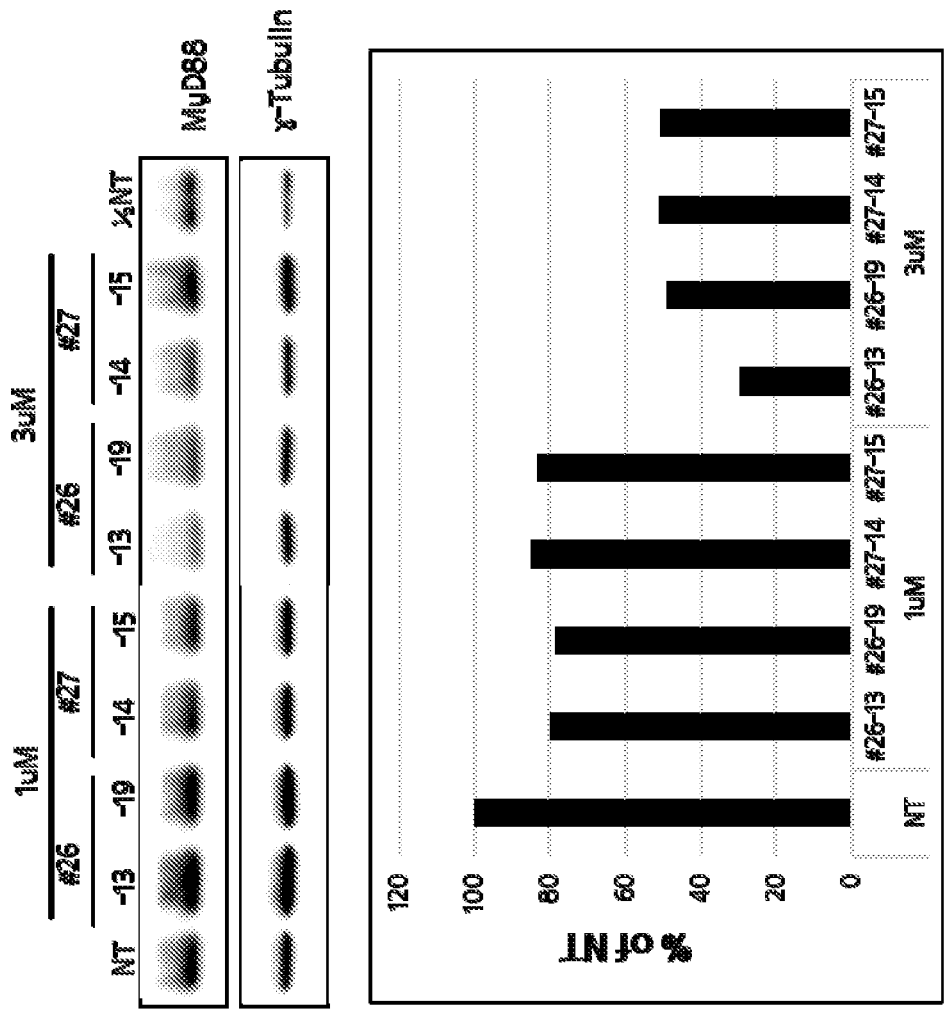
FIG. 11 shows the inhibition of MyD88 protein expression by exemplary cp-asiRNAs. The cp-asiRNAs were incubated without transfection vehicle in the presence of HeLa cells at a concentration of 1 uM or 3 uM and, after 48 hours, protein was extracted and a western blot performed. (NT=no treatment).

The results of the western blot assay are depicted in FIG. 11. All 3 μM cp-asiMyD88 incubated cell lines exhibited 50% or more of MyD88 protein inhibition. In addition, the cp-asiMyD88(26)-13 were shown to have a higher efficiency in the MyD88 inhibition ability than other cp-asiMD88s (FIG. 11).

Example 12: Screening for Toll-Like Receptor 3 Specific Asymmetric Small Interfering RNAs To identify asymmetric small interfering RNAs (asiRNAs) that inhibit Toll-like receptor 3 with high efficiency, 100 asiRNAs were synthesized and screened. The nucleic acid sequences of the screened asiRNAs are provided in Table 7.

TABLE 7

Nucleic acid sequences for exemplary Toll-like receptor 3 targeting asiRNA.
TLR3 asiRNA Sequence

| Name | Sequence (5'-3') | SEQ ID NO | Name | Sequence (5'-3') | SEQ ID NO |
|---|---|---|---|---|---|
| TLR3asiRNA S(1) | AUCUUUCCUACAACAA | 178 | TLR3asiRNA AS(1) | UUGUUGUAGGAAAGAUCGAGC | 179 |
| TLR3asiRNA S(2) | UCUUUCCUACAACAAC | 180 | TLR3asiRNA AS(2) | GUUGUUGUAGGAAAGAUCGAG | 181 |
| TLR3asiRNA S(3) | GGCCCUUAAAAAUGUG | 182 | TLR3asiRNA AS(3) | CACAUUUUUAAGGGCCACCCU | 183 |
| TLR3asiRNA S(4) | GCCCUUAAAAAUGUGG | 184 | TLR3asiRNA AS(4) | CCACAUUUUUAAGGGCCACCC | 185 |
| TLR3asiRNA S(5) | CCCUUAAAAAUGUGGA | 186 | TLR3asiRNA AS(5) | UCCACAUUUUUAAGGGCCACC | 187 |
| TLR3asiRNA S(6) | CCUUAAAAAUGUGGAU | 188 | TLR3asiRNA AS(6) | AUCCACAUUUUUAAGGGCCAC | 189 |
| TLR3asiRNA S(7) | CUUAAAAAUGUGGAUA | 190 | TLR3asiRNA AS(7) | UAUCCACAUUUUUAAGGGCCA | 191 |
| TLR3asiRNA S(8) | UCGUAACUUGACCAUU | 192 | TLR3asiRNA AS(8) | AAUGGUCAAGUUACGAAGAGG | 193 |
| TLR3asiRNA S(9) | CGUAACUUGACCAUUC | 194 | TLR3asiRNA AS(9) | GAAUGGUCAAGUUACGAAGAG | 195 |
| TLR3asiRNA S(10) | GUAACUUGACCAUUCU | 196 | TLR3asiRNA AS(10) | AGAAUGGUCAAGUUACGAAGA | 197 |
| TLR3asiRNA S(11) | UAACUUGACCAUUCUG | 198 | TLR3asiRNA AS(11) | CAGAAUGGUCAAGUUACGAAG | 199 |
| TLR3asiRNA S(12) | AACUUGACCAUUCUGG | 200 | TLR3asiRNA AS(12) | CCAGAAUGGUCAAGUUACGAA | 201 |
| TLR3asiRNA S(13) | ACUUGACCAUUCUGGA | 202 | TLR3asiRNA AS(13) | UCCAGAAUGGUCAAGUUACGA | 203 |
| TLR3asiRNA S(14) | AACAACAACAUAGCCA | 204 | TLR3asiRNA AS(14) | UGGCUAUGUUGUUGUUGCUUA | 205 |
| TLR3asiRNA S(15) | ACAACAACAUAGCCAA | 206 | TLR3asiRNA AS(15) | UUGGCUAUGUUGUUGUUGCUU | 207 |
| TLR3asiRNA S(16) | CAACAACAUAGCCAAC | 208 | TLR3asiRNA AS(16) | GUUGGCUAUGUUGUUGUUGCU | 209 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
|---|---|---|---|---|---|
| TLR3asiRNA S(17) | AACAACAUAGCCAACA | 210 | TLR3asiRNA AS(17) | UGUUGGCUAUGUUGUUGUUGC | 211 |
| TLR3asiRNA S(18) | ACAACAUAGCCAACAU | 212 | TLR3asiRNA AS(18) | AUGUUGGCUAUGUUGUUGUUG | 213 |
| TLR3asiRNA S(19) | CAACAUAGCCAACAUA | 214 | TLR3asiRNA AS(19) | UAUGUUGGCUAUGUUGUUGUU | 215 |
| TLR3asiRNA S(20) | AACAUAGCCAACAUAA | 216 | TLR3asiRNA AS(20) | UUAUGUUGGCUAUGUUGUUGU | 217 |
| TLR3asiRNA S(21) | ACAUAGCCAACAUAAA | 218 | TLR3asiRNA AS(21) | UUUAUGUUGGCUAUGUUGUUG | 219 |
| TLR3asiRNA S(22) | AUAGCCAACAUAAAUG | 220 | TLR3asiRNA AS(22) | CAUUUAUGUUGGCUAUGUUGU | 221 |
| TLR3asiRNA S(23) | UAGCCAACAUAAAUGA | 222 | TLR3asiRNA AS(23) | UCAUUUAUGUUGGCUAUGUUG | 223 |
| TLR3asiRNA S(24) | AAUCUCUCAAAUUUUG | 224 | TLR3asiRNA AS(24) | CAAAAUUUGAGAGAUUGGUCU | 225 |
| TLR3asiRNA S(25) | UGCACUCUGUUUGCGA | 226 | TLR3asiRNA AS(25) | UCGCAAACAGAGUGCAUGGUU | 227 |
| TLR3asiRNA S(26) | GCACUCUGUUUGCGAA | 228 | TLR3asiRNA AS(26) | UUCGCAAACAGAGUGCAUGGU | 229 |
| TLR3asiRNA S(27) | CACUCUGUUUGCGAAG | 230 | TLR3asiRNA AS(27) | CUUCGCAAACAGAGUGCAUGG | 231 |
| TLR3asiRNA S(28) | ACUCUGUUUGCGAAGA | 232 | TLR3asiRNA AS(28) | UCUUCGCAAACAGAGUGCAUG | 233 |
| TLR3asiRNA S(29) | CUCUGUUUGCGAAGAG | 234 | TLR3asiRNA AS(29) | CUCUUCGCAAACAGAGUGCAU | 235 |
| TLR3asiRNA S(30) | UCUGUUUGCGAAGAGG | 236 | TLR3asiRNA AS(30) | CCUCUUCGCAAACAGAGUGCA | 237 |
| TLR3asiRNA S(31) | CUGUUUGCGAAGAGGA | 238 | TLR3asiRNA AS(31) | UCCUCUUCGCAAACAGAGUGC | 239 |
| TLR3asiRNA S(32) | UGUUUGCGAAGAGGAA | 240 | TLR3asiRNA AS(32) | UUCCUCUUCGCAAACAGAGUG | 241 |
| TLR3asiRNA S(33) | GUUUGCGAAGAGGAAU | 242 | TLR3asiRNA AS(33) | AUUCCUCUUCGCAAACAGAGU | 243 |
| TLR3asiRNA S(34) | UUUGCGAAGAGGAAUG | 244 | TLR3asiRNA AS(34) | CAUUCCUCUUCGCAAACAGAG | 245 |
| TLR3asiRNA S(35) | UUGCGAAGAGGAAUGU | 246 | TLR3asiRNA AS(35) | ACAUUCCUCUUCGCAAACAGA | 247 |
| TLR3asiRNA S(36) | UGCGAAGAGGAAUGUU | 248 | TLR3asiRNA AS(36) | AACAUUCCUCUUCGCAAACAG | 249 |
| TLR3asiRNA S(37) | GCGAAGAGGAAUGUUU | 250 | TLR3asiRNA AS(37) | AAACAUUCCUCUUCGCAAACA | 251 |
| TLR3asiRNA S(38) | CGAAGAGGAAUGUUUA | 252 | TLR3asiRNA AS(38) | UAAACAUUCCUCUUCGCAAAC | 253 |
| TLR3asiRNA S(39) | GAAGAGGAAUGUUUAA | 254 | TLR3asiRNA AS(39) | UUAAACAUUCCUCUUCGCAAA | 255 |
| TLR3asiRNA S(40) | AAGAGGAAUGUUUAAA | 256 | TLR3asiRNA AS(40) | UUUAAACAUUCCUCUUCGCAA | 257 |
| TLR3asiRNA S(41) | AGAGGAAUGUUUAAAU | 258 | TLR3asiRNA AS(41) | AUUUAAACAUUCCUCUUCGCA | 259 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
| --- | --- | --- | --- | --- | --- |
| TLR3asiRNA S(42) | GAGGAAUGUUUAAAUC | 260 | TLR3asiRNA AS(42) | GAUUUAAACAUUCCUCUUCGC | 261 |
| TLR3asiRNA S(43) | AGGAAUGUUUAAAUCU | 262 | TLR3asiRNA AS(43) | AGAUUUAAACAUUCCUCUUCG | 263 |
| TLR3asiRNA S(44) | GGAAUGUUUAAAUCUC | 264 | TLR3asiRNA AS(44) | GAGAUUUAAACAUUCCUCUUC | 265 |
| TLR3asiRNA S(45) | CUUGAACUGGCCAGUU | 266 | TLR3asiRNA AS(45) | AACUGGCCAGUUCAAGAUGCA | 267 |
| TLR3asiRNA S(46) | UUGAACUGGCCAGUUC | 268 | TLR3asiRNA AS(46) | GAACUGGCCAGUUCAAGAUGC | 269 |
| TLR3asiRNA S(47) | UGAACUGGCCAGUUCA | 270 | TLR3asiRNA AS(47) | UGAACUGGCCAGUUCAAGAUG | 271 |
| TLR3asiRNA S(48) | GAACUGGCCAGUUCAG | 272 | TLR3asiRNA AS(48) | CUGAACUGGCCAGUUCAAGAU | 273 |
| TLR3asiRNA S(49) | AACUGGCCAGUUCAGA | 274 | TLR3asiRNA AS(49) | UCUGAACUGGCCAGUUCAAGA | 275 |
| TLR3asiRNA S(50) | ACUGGCCAGUUCAGAA | 276 | TLR3asiRNA AS(50) | UUCUGAACUGGCCAGUUCAAG | 277 |
| TLR3asiRNA S(51) | CUGGCCAGUUCAGAAA | 278 | TLR3asiRNA AS(51) | UUUCUGAACUGGCCAGUUCAA | 279 |
| TLR3asiRNA S(52) | UGGCCAGUUCAGAAAG | 280 | TLR3asiRNA AS(52) | CUUUCUGAACUGGCCAGUUCA | 281 |
| TLR3asiRNA S(53) | GGCCAGUUCAGAAAGA | 282 | TLR3asiRNA AS(53) | UCUUUCUGAACUGGCCAGUUC | 283 |
| TLR3asiRNA S(54) | GCCAGUUCAGAAAGAA | 284 | TLR3asiRNA AS(54) | UUCUUUCUGAACUGGCCAGUU | 285 |
| TLR3asiRNA S(55) | CCAGUUCAGAAAGAAC | 286 | TLR3asiRNA AS(55) | GUUCUUUCUGAACUGGCCAGU | 287 |
| TLR3asiRNA S(56) | CAGUUCAGAAAGAACG | 288 | TLR3asiRNA AS(56) | CGUUCUUUCUGAACUGGCCAG | 289 |
| TLR3asiRNA S(57) | AGUUCAGAAAGAACGG | 290 | TLR3asiRNA AS(57) | CCGUUCUUUCUGAACUGGCCA | 291 |
| TLR3asiRNA S(58) | GUUCAGAAAGAACGGA | 292 | TLR3asiRNA AS(58) | UCCGUUCUUUCUGAACUGGCC | 293 |
| TLR3asiRNA S(59) | UUCAGAAAGAACGGAU | 294 | TLR3asiRNA AS(59) | AUCCGUUCUUUCUGAACUGGC | 295 |
| TLR3asiRNA S(60) | UCAGAAAGAACGGAUA | 296 | TLR3asiRNA AS(60) | UAUCCGUUCUUUCUGAACUGG | 297 |
| TLR3asiRNA S(61) | AAUUGCAAGUAGCACU | 298 | TLR3asiRNA AS(61) | AGUGCUACUUGCAAUUUAUGA | 299 |
| TLR3asiRNA S(62) | AUUGCAAGUAGCACUU | 300 | TLR3asiRNA AS(62) | AAGUGCUACUUGCAAUUUAUG | 301 |
| TLR3asiRNA S(63) | UUGCAAGUAGCACUUG | 302 | TLR3asiRNA AS(63) | CAAGUGCUACUUGCAAUUUAU | 303 |
| TLR3asiRNA S(64) | UGCAAGUAGCACUUGG | 304 | TLR3asiRNA AS(64) | CCAAGUGCUACUUGCAAUUUA | 305 |
| TLR3asiRNA S(65) | GCAAGUAGCACUUGGA | 306 | TLR3asiRNA AS(65) | UCCAAGUGCUACUUGCAAUUU | 307 |
| TLR3asiRNA S(66) | CAAGUAGCACUUGGAU | 308 | TLR3asiRNA AS(66) | AUCCAAGUGCUACUUGCAAUU | 309 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
| --- | --- | --- | --- | --- | --- |
| TLR3asiRNA S(67) | AAGUAGCACUUGGAUC | 310 | TLR3asiRNA AS(67) | GAUCCAAGUGCUACUUGCAAU | 311 |
| TLR3asiRNA S(68) | UGCCCCCUUUGAACUC | 312 | TLR3asiRNA AS(68) | GAGUUCAAAGGGGCACUGUC | 313 |
| TLR3asiRNA S(69) | UCUGGGAACAUUUCUC | 314 | TLR3asiRNA AS(69) | GAGAAAUGUUCCCAGACCCAA | 315 |
| TLR3asiRNA S(70) | CAGCAUCAAAGAAGC | 316 | TLR3asiRNA AS(70) | GCUUCUUUUGAUGCUGUUAAC | 317 |
| TLR3asiRNA S(71) | CACGUGUGAAAGUAUU | 318 | TLR3asiRNA AS(71) | AAUACUUUCACACGUGCAAUC | 319 |
| TLR3asiRNA S(72) | GUCUCACCUCCACAUC | 320 | TLR3asiRNA AS(72) | GAUGUGGAGGUGAGACAGACC | 321 |
| TLR3asiRNA S(73) | UGUCUCACCUCCACAU | 322 | TLR3asiRNA AS(73) | AUGUGGAGGUGAGACAGACCC | 323 |
| TLR3asiRNA S(74) | AGAUUCAAGGUACAUC | 324 | TLR3asiRNA AS(74) | GAUGUACCUUGAAUCUUUUGC | 325 |
| TLR3asiRNA S(75) | GGAAACACGCAAACCC | 326 | TLR3asiRNA AS(75) | GGGUUUGCGUGUUUCCAGAGC | 327 |
| TLR3asiRNA S(76) | UGGAAACACGCAAACC | 328 | TLR3asiRNA AS(76) | GGUUUGCGUGUUUCCAGAGCC | 329 |
| TLR3asiRNA S(77) | UUGAGAAACUAGAAAU | 330 | TLR3asiRNA AS(77) | AUUUCUAGUUUCUCAAGACCC | 331 |
| TLR3asiRNA S(78) | CUUGAGAAACUAGAAA | 332 | TLR3asiRNA AS(78) | UUUCUAGUUUCUCAAGACCCU | 333 |
| TLR3asiRNA S(79) | AACAUCCGUUGAGAAG | 334 | TLR3asiRNA AS(79) | CUUCUCAACGGAUGUUAUGAG | 335 |
| TLR3asiRNA S(80) | GUGCCCCUUUGAACU | 336 | TLR3asiRNA AS(80) | AGUUCAAAGGGGCACUGUCU | 337 |
| TLR3asiRNA S(81) | AGUGCCCCUUUGAAC | 338 | TLR3asiRNA AS(81) | GUUCAAAGGGGCACUGUCUU | 339 |
| TLR3asiRNA S(82) | CAGUGCCCCUUUGAA | 340 | TLR3asiRNA AS(82) | UUCAAAGGGGCACUGUCUUU | 341 |
| TLR3asiRNA S(83) | GGAGGAUAUCUUUUUA | 342 | TLR3asiRNA AS(83) | UAAAAGAUAUCCUCCAGCCC | 343 |
| TLR3asiRNA S(84) | UGGAGGAUAUCUUUUU | 344 | TLR3asiRNA AS(84) | AAAAAGAUAUCCUCCAGCCCU | 345 |
| TLR3asiRNA S(85) | ACUGAACCAUGCACUC | 346 | TLR3asiRNA AS(85) | GAGUGCAUGGUUCAGUUUAUA | 347 |
| TLR3asiRNA S(86) | UGAACCAUGCACUCUG | 348 | TLR3asiRNA AS(86) | CAGAGUGCAUGGUUCAGUUUA | 349 |
| TLR3asiRNA S(87) | GAACCAUGCACUCUGU | 350 | TLR3asiRNA AS(87) | ACAGAGUGCAUGGUUCAGUUU | 351 |
| TLR3asiRNA S(88) | AACCAUGCACUCUGUU | 352 | TLR3asiRNA AS(88) | AACAGAGUGCAUGGUUCAGUU | 353 |
| TLR3asiRNA S(89) | ACCAUGCACUCUGUUU | 354 | TLR3asiRNA AS(89) | AAACAGAGUGCAUGGUUCAGU | 355 |
| TLR3asiRNA S(90) | CCAUGCACUCUGUUUG | 356 | TLR3asiRNA AS(90) | CAAACAGAGUGCAUGGUUCAG | 357 |
| TLR3asiRNA S(91) | CAUGCACUCUGUUUGC | 358 | TLR3asiRNA AS(91) | GCAAACAGAGUGCAUGGUUCA | 359 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
|---|---|---|---|---|---|
| TLR3asiRNA S(92) | CUGCAUCUUGAACUGG | 360 | TLR3asiRNA AS(92) | CCAGUUCAAGAUGCAGUGAGA | 361 |
| TLR3asiRNA S(93) | ACUGCAUCUUGAACUG | 362 | TLR3asiRNA AS(93) | CAGUUCAAGAUGCAGUGAGAU | 363 |
| TLR3asiRNA S(94) | CACUGCAUCUUGAACU | 364 | TLR3asiRNA AS(94) | AGUUCAAGAUGCAGUGAGAUU | 365 |
| TLR3asiRNA S(95) | UCACUGCAUCUUGAAC | 366 | TLR3asiRNA AS(95) | GUUCAAGAUGCAGUGAGAUUU | 367 |
| TLR3asiRNA S(96) | UAAAUUGCAAGUAGCA | 368 | TLR3asiRNA AS(96) | UGCUACUUGCAAUUUAUGACG | 369 |
| TLR3asiRNA S(97) | AUAAAUUGCAAGUAGC | 370 | TLR3asiRNA AS(97) | GCUACUUGCAAUUUAUGACGA | 371 |
| TLR3asiRNA S(98) | CGUCAUAAAUUGCAAG | 372 | TLR3asiRNA AS(98) | CUUGCAAUUUAUGACGAAAGG | 373 |
| TLR3asiRNA S(99) | UCGUCAUAAAUUGCAA | 374 | TLR3asiRNA AS(99) | UUGCAAUUUAUGACGAAAGGC | 375 |
| TLR3asiRNA S(100) | UUCGUCAUAAAUUGCA | 376 | TLR3asiRNA AS(100) | UGCAAUUUAUGACGAAAGGCA | 377 |

The asiRNAs listed in Table 7 were incubated at 95° C. for 2 minutes and at 37° C. for 1 hour in annealing buffer (Bioneer Inc. Korea). Proper strand annealing was confirmed via gel electrophoresis using UV transilluminator. For the screen, 5×10³ HaCaT cells (ATCC) that had been cultured in Dulbecco's modified Eagle's medium (DMEM, Gibco) containing 10% fetal bovine serum (FBS, Gibco) and 100 units/ml Penicillin and 100 μg/ml Streptomycin in a 100 mm cell culture dish were seeded in 96 well plates. The HaCaT cells were transfected with 0.1 nM of the asiRNAs using RNAiMAX (Invitrogen Inc.) according to the manufacturer's instructions. The TLR3 mRNA levels in the transfected cells were measured 24 hours after transfection using qRT-PCR. Specifically, total RNA were extracted using TOYOBO lysis reagent and then ⅕ volume of the reaction mixture was used for cDNA synthesis using the TOYOBO RT reagent (TOYOBO SuperPrep). The synthesized cDNA was diluted and then quantitative RT-PCR was performed using THUNDERBIRD® Probe qPCR Mix (TOYOBO). Amplification of the target gene was detected using TLR3 TaqMan® Probe (Hs01551078_m1) and 18S TaqMan® Probe (Hs03928985_g1).

Figure 12:
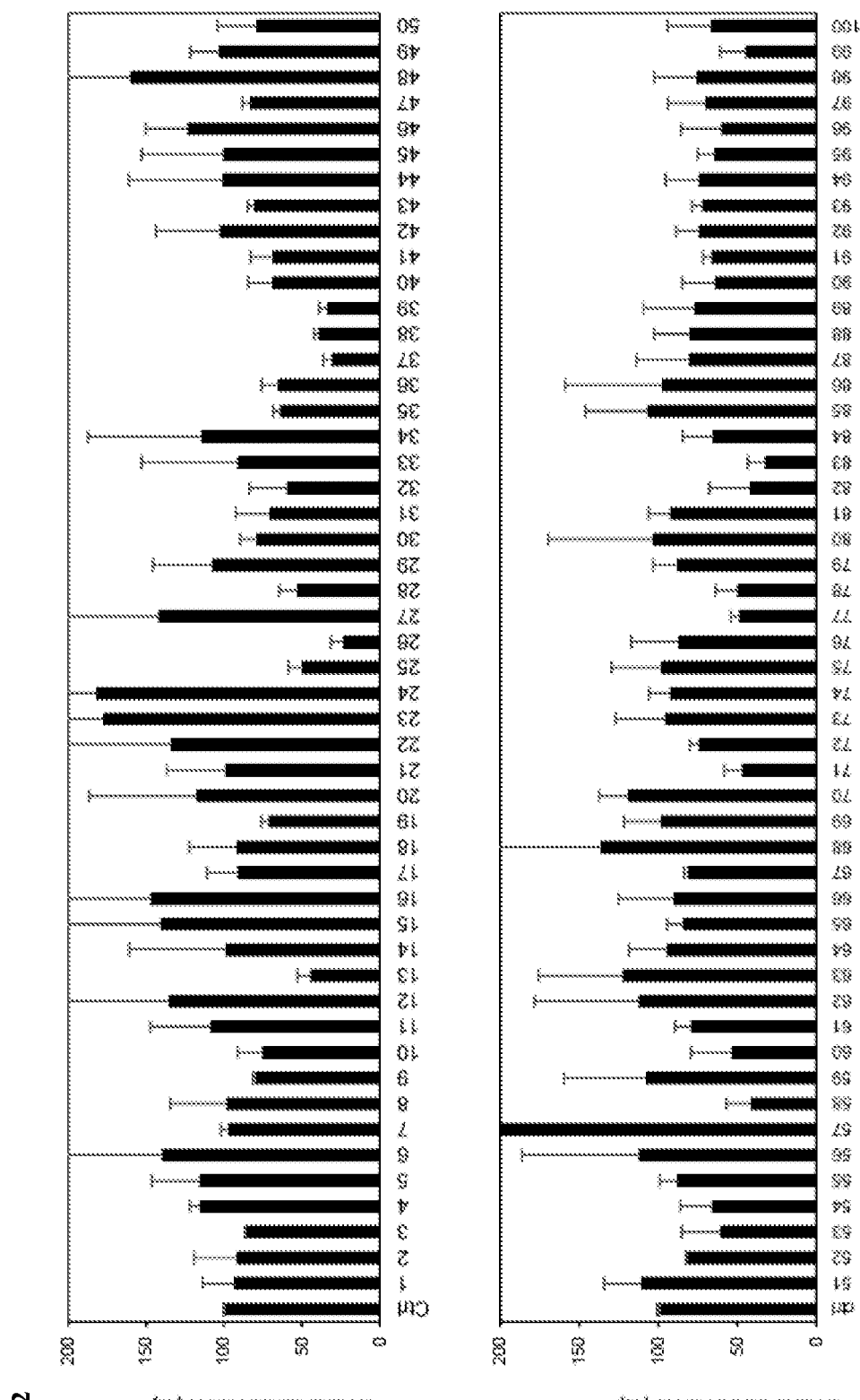
FIG. 12 shows the gene silencing efficiency of exemplary asiRNAs that target Toll-like receptor 3 (TLR3). The asiRNAs were transfected into HaCaT cells at a concentration of 0.1 nM, and, after 24 hours, the degree of TLR3 mRNA expression was determined using qRT-PCR. The mean and standard deviation of two repeat experiments are depicted.

The expression level of TLR3 inhibition by each of the 100 asiRNAs is provided in FIG. 12. 17 of the asiRNA sequences, asiRNA (13), asiRNA (25), asiRNA (26), asiRNA (28), asiRNA (32), asiRNA (33), asiRNA (37), asiRNA (38), asiRNA (39), asiRNA (53), asiRNA (58), asiRNA (60), asiRNA (71), asiRNA (77), asiRNA (78), asiRNA (82) and asiRNA (83), were selected for use in follow-up studies.

Example 13: Chemical Modification of asiRNAs for Self-Delivery

Figure 13:
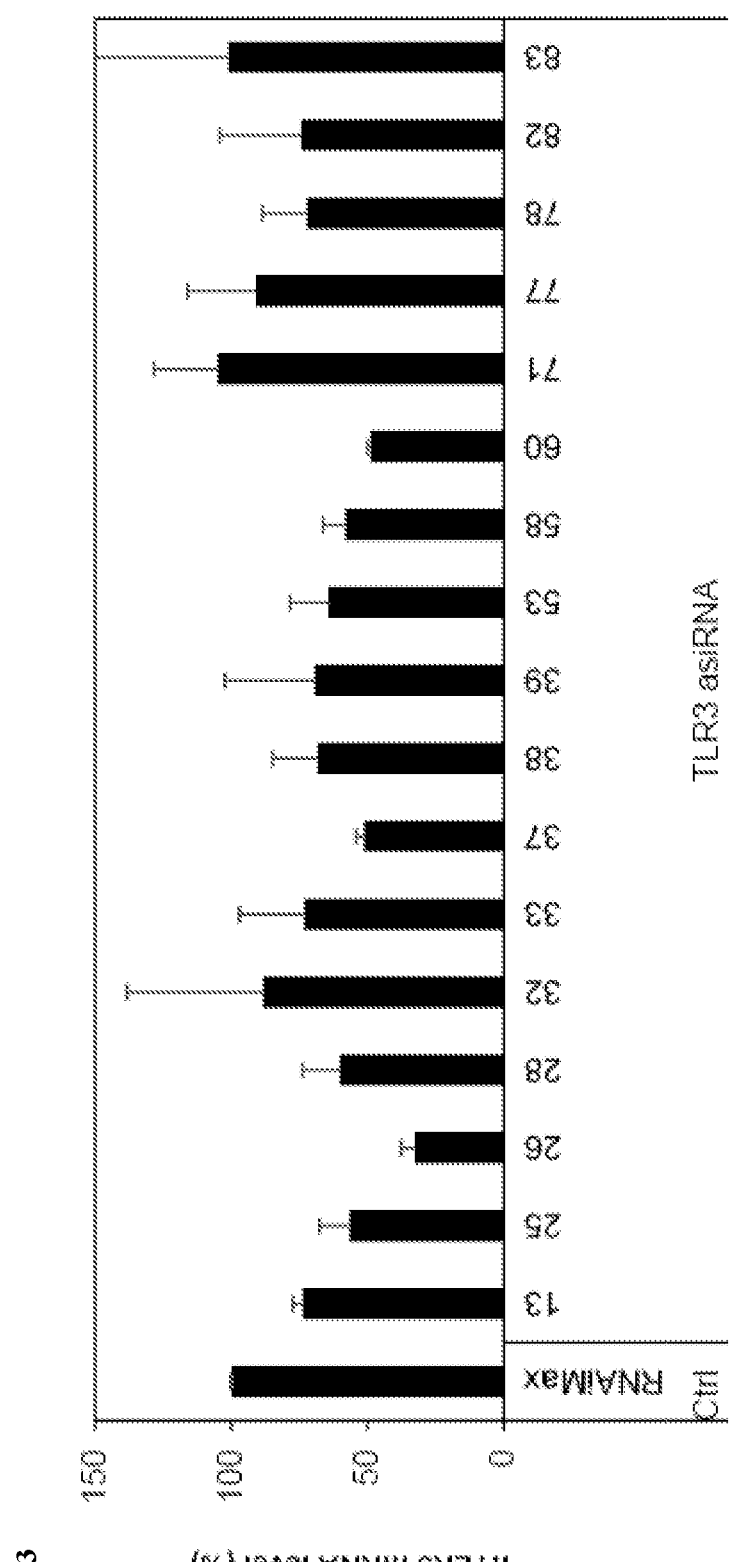
FIG. 13 shows the gene silencing efficiency of exemplary asiRNAs that target TLR3. The asiRNAs were transfected into HaCaT cells at a concentration of 0.1 nM and, after 24 hours, the degree of TLR3 mRNA expression was determined using qRT-PCR. The mean and standard deviation of two repeat experiments are depicted.
Figure 14:
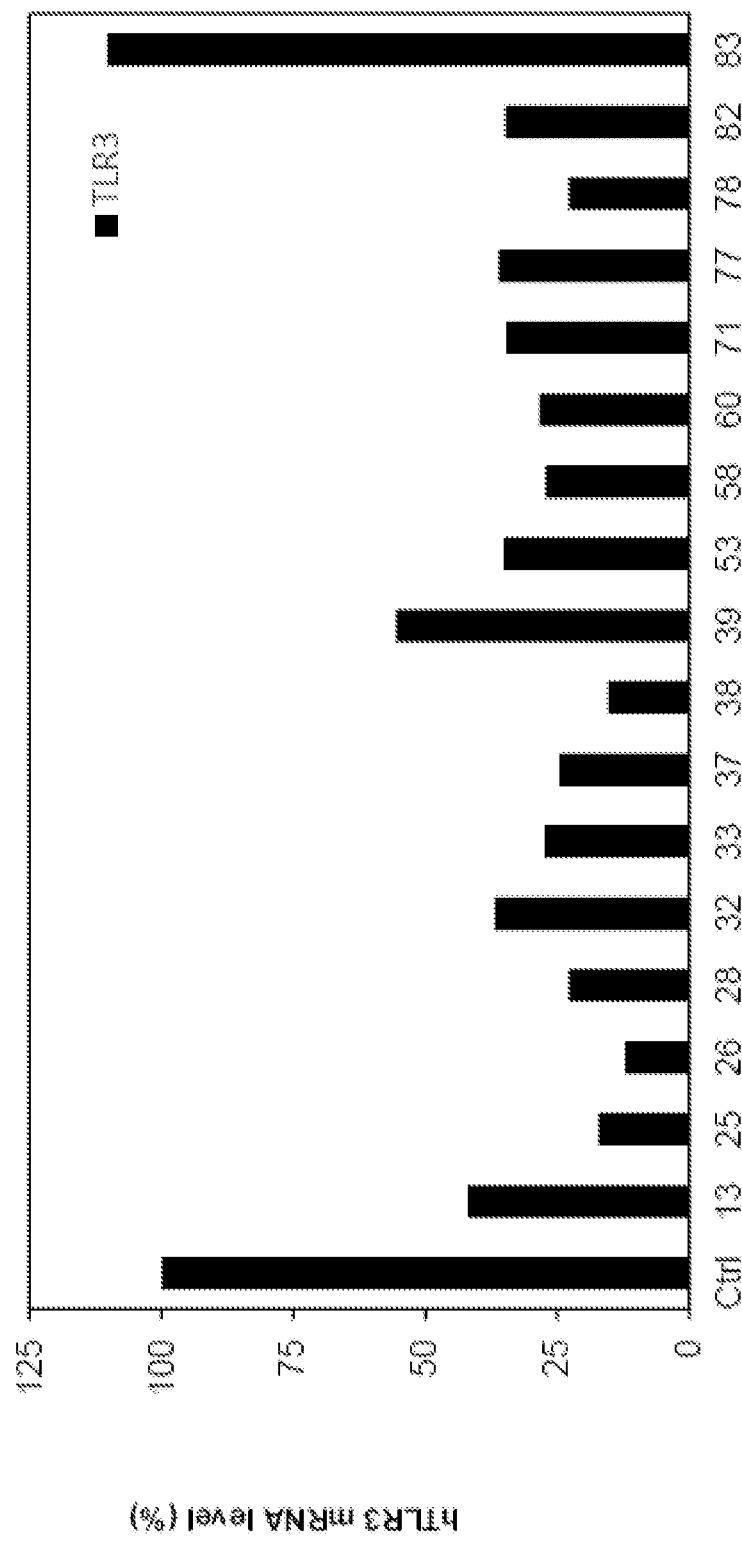
FIG. 14 shows the gene silencing efficiency of exemplary asiRNAs that target TLR3. The asiRNAs were transfected into HaCaT cells at a concentration of 0.3 nM and, after 24 hours, the degree of TLR3 mRNA expression was measured using qRT-PCR.
Figure 15:
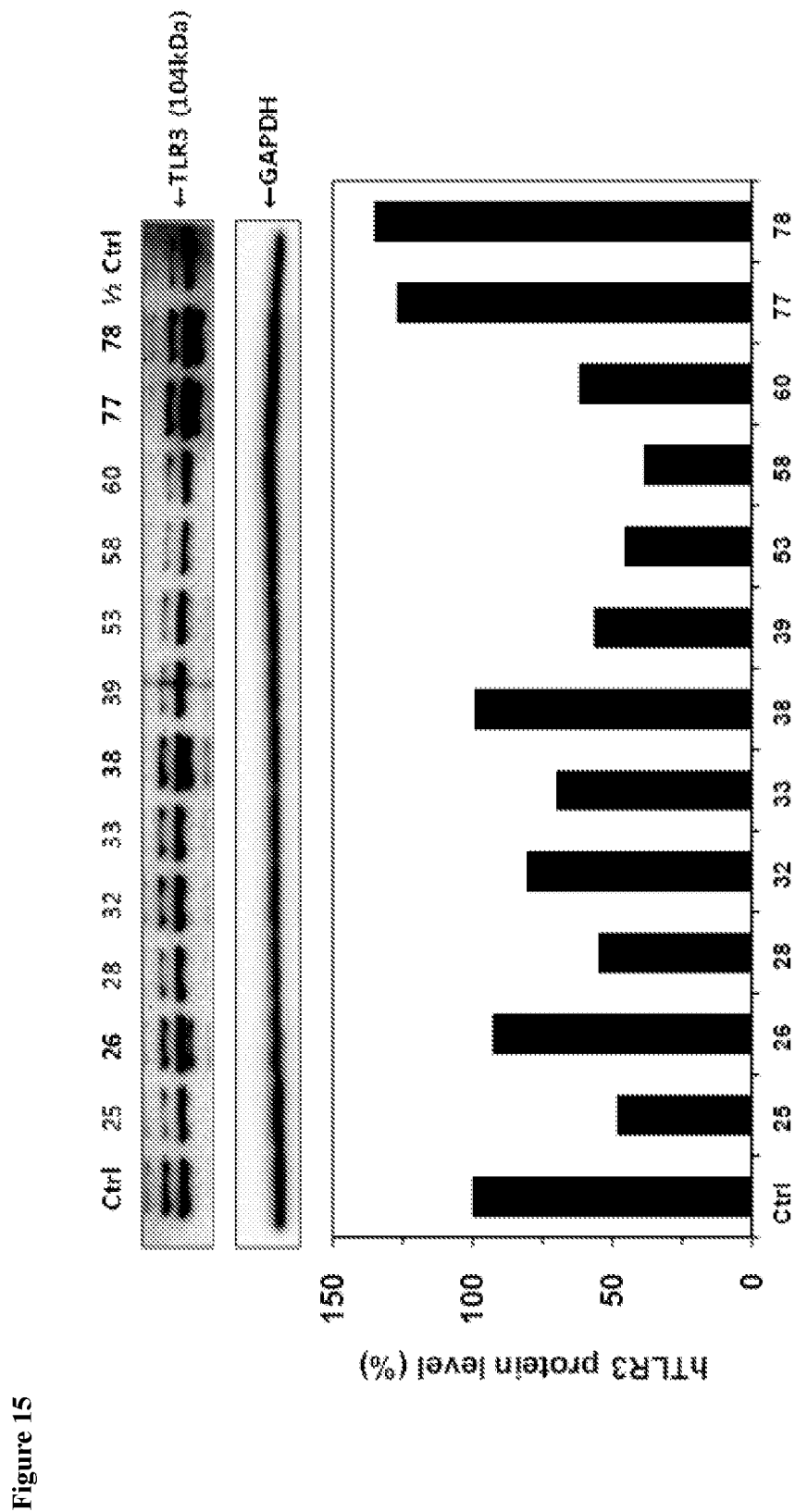
FIG. 15 shows the inhibition of TLR3 protein expression by exemplary asiRNAs. The asiRNAs were transfected into HaCaT cells at a concentration of 10 nM and, after 48 hours, the degree of TLR3 protein expression was determined using western blot.
Figure 16:
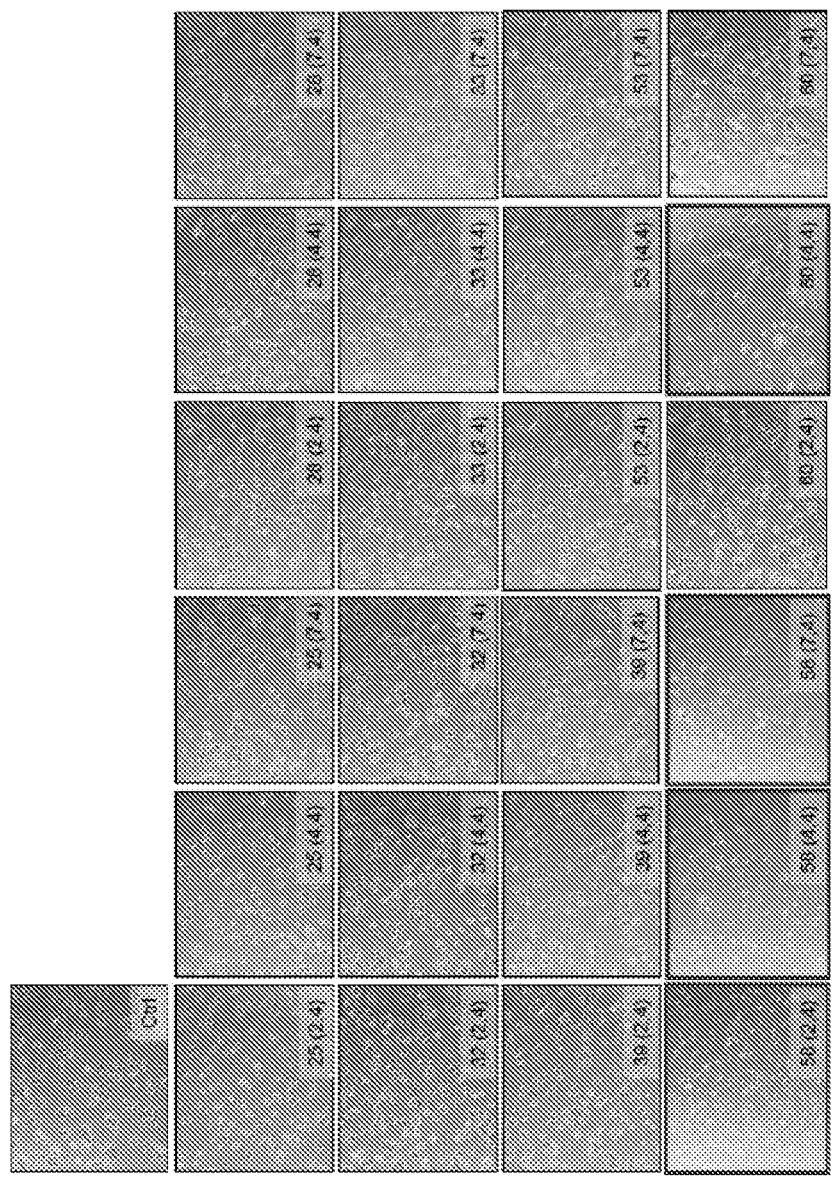
FIG. 16 shows images of HaCaT cells treated by exemplary cp-asiRNAs for 24 hours. The cp-asiRNAs were incubation of 1 uM and, after 24 hours, the morphology of the HaCaT cells was imaged by ECLIPSE 100 (Nikon).

Chemical modifications were applied to the asiRNAs selected in Example 12 and the cellular delivery of the modified asiRNAs was tested in the absence of other delivery vehicle. As described below, certain of the modifications improved endocytosis and stability of asiRNAs. Such cell penetrating asiRNAs (cp-asiRNAs) are able to be delivered into the cell in the absence of a delivery vehicle. The expression of TLR3 mRNA by the cells is provided in FIGS. 13 and 14 and the TLR3 protein levels are provided in FIG. 15, as determined using methods described above. The morphology of the cells is depicted in FIG. 16.

Potential cp-asiRNA (Table 8) were screened for Toll-like receptor 3 (TLR3) mRNA inhibition in HaCaT cells. Each potential cp-asiRNA was incubated with HaCaT cells, human skin keratinocyte cell line, at 1 μM and 3 μM without a delivery vehicle and TLR3 expression levels were measured by qRT-PCR and western blot study.

TABLE 8

Modified asiRNA sequences tested for self-delivery and TLR3 inhibition.

| Name | Sense(5' to 3') | SEQ ID NO: |
|---|---|---|
| TLR3cp-asiRNA S 25 | mUGmCAmCUmCUmGUmUUmGC*mG*A*cholesterol | 378 |
| TLR3cp-asiRNA AS 25(2,4) | UCGCAAACAGAGUGmCmAU*G*G*U*U | 379 |
| TLR3cp-asiRNA AS 25(4,4) | UCGCAAACAGAGUGmCmAmU*mG*G*U*U | 380 |

TABLE 8-continued

Modified asiRNA sequences tested for self-delivery and TLR3 inhibition.

| Name | Sense(5' to 3') | SEQ ID NO: |
|---|---|---|
| TLR3cp-asiRNA AS 25(7,4) | UCGCAAACAGAGUGmCmAmU*mG*mG*mU*mU | 381 |
| TLR3cp-asiRNA S 28 | mACmUCmUGmUUmUGmCGmAA*mG*A*cholesterol | 382 |
| TLR3cp-asiRNA AS 28(2,4) | UCUUCGCAAACAGAmGmUG*C*A*U*G | 383 |
| TLR3cp-asiRNA AS 28(4,4) | UCUUCGCAAACAGAmGmUmG*mC*A*U*G | 384 |
| TLR3cp-asiRNA AS 28(7,4) | UCUUCGCAAACAGAmGmUmG*mC*mA*mU*mG | 385 |
| TLR3cp-asiRNA S 32 | mUGmUUmUGmCGmAAmGAmGG*mA*A*cholesterol | 386 |
| TLR3cp-asiRNA AS 32(2,4) | UUCCUCUUCGCAAAmCmAG*A*G*U*G | 387 |
| TLR3cp-asiRNA AS 32(4,4) | UUCCUCUUCGCAAAmCmAmG*mA*G*U*G | 388 |
| TLR3cp-asiRNA AS 32(7,4) | UUCCUCUUCGCAAAmCmAmG*mA*mG*mU*mG | 389 |
| TLR3cp-asiRNA S 33 | mGUmUUmGCmGAmAGmAGmGA*mA*U*cholesterol | 390 |
| TLR3cp-asiRNA AS 33(2,4) | AUUCCUCUUCGCAAmAmCA*G*A*G*U | 391 |
| TLR3cp-asiRNA AS 33(4,4) | AUUCCUCUUCGCAAmAmCmA*mG*A*G*U | 392 |
| TLR3cp-asiRNA AS 33(7,4) | AUUCCUCUUCGCAAmAmCmA*mG*mA*mG*mU | 393 |
| TLR3cp-asiRNA S 39 | mGAmAGmAGmGAmAUmGUmUU*mA*A*cholesterol | 394 |
| TLR3cp-asiRNA AS 39(2,4) | UUAAACAUUCCUCUmUmCG*C*A*A*A | 395 |
| TLR3cp-asiRNA AS 39(4,4) | UUAAACAUUCCUCUmUmCmG*mC*A*A*A | 396 |
| TLR3cp-asiRNA AS 39(7,4) | UUAAACAUUCCUCUmUmCmG*mC*mA*mA*mA | 397 |
| TLR3cp-asiRNA S 53 | mGGmCCmAGmUUmCAmGAmAA*mG*A*cholesterol | 398 |
| TLR3cp-asiRNA AS 53(2,4) | UCUUUCUGAACUGGmCmCA*G*U*U*C | 399 |
| TLR3cp-asiRNA AS 53(4,4) | UCUUUCUGAACUGGmCmCmA*mG*U*U*C | 400 |
| TLR3cp-asiRNA AS 53(7,4) | UCUUUCUGAACUGGmCmCmA*mG*mU*mU*mC | 401 |
| TLR3cp-asiRNA S 58 | mGUmUCmAGmAAmAGmAAmCG*mG*A*cholesterol | 402 |
| TLR3cp-asiRNA AS 58(2,4) | UCCGUUCUUUCUGAmAmCU*G*G*C*C | 403 |
| TLR3cp-asiRNA AS 58(4,4) | UCCGUUCUUUCUGAmAmCmU*mG*G*C*C | 404 |
| TLR3cp-asiRNA AS 58(7,4) | UCCGUUCUUUCUGAmAmCmU*mG*mG*mC*mC | 405 |
| TLR3cp-asiRNA S 60 | mUCmAGmAAmAGmAAmCGmGA*mU*A*cholesterol | 406 |
| TLR3cp-asiRNA AS 60(2,4) | UAUCCGUUCUUUCUmGmAA*C*U*G*G | 407 |
| TLR3cp-asiRNA AS 60(4,4) | UAUCCGUUCUUUCUmGmAmA*mC*U*G*G | 408 |
| TLR3cp-asiRNA AS 60(7,4) | UAUCCGUUCUUUCUmGmAmA*mC*mU*mG*mG | 409 |

(m = 2'-O-Methyl RNA.
* = phosphorothioate bond).

HaCaT cells (ATCC) were cultured in Dulbecco's modified Eagle's medium (DMEM, Gibco) containing 10% fetal bovine serum (FBS, Gibco) and 100 units/ml Penicillin 100 µg/ml Streptomycin in a 100 mm cell culture dish. The potential cp-asiRNAs listed in Table 8 were incubated at 95° C. for 2 minutes and at 37° C. for 1 hour in Opti-MEM (Gibco). Proper strand annealing of the potential cp-asiRNAs was confirmed by gel electrophoresis.

On that day cp-asiRNAs treatment, 5×10$^4$ cells were seeded into 24 well plates and then cultured in the presence of the potential cp-asiRNAs in Opti-MEM for 24 hours, at which point the cp-asiRNA-containing Opti-MEM media was replaced with a serum-containing media. Twenty-four hours later, TLR3 mRNA levels in HaCaT cells were determined using qRT-PCR. Specifically, total RNA were extracted using RNAiPlus® (TaKaRa) and then 500 ng of the reaction mixture was used for cDNA synthesis using the High-capacity cDNA reverse transcription kit (Applied Biosystems). The synthesized cDNA was diluted and then quantitative RT-PCR was performed using power SYBR green PCR master Mix (Applied Biosystems). The following primer sequences were used:

TABLE 9

Primer sequences.

| Name | | Sequence (5'-3') | SEQ ID NO: | size |
|---|---|---|---|---|
| Human GAPDH | Forward | GAG TCA ACG GAT TTG GTC GT | 91 | 186 |
| | Reverse | GAC AAG CTT CCC GTT CTC AG | 92 | |
| Human TLR3 (Toll-like receptor 3) | Forward | TGC CCC CTT TGA ACT CTT TT | 410 | 298 |
| | Reverse | AAA AAC ACC CGC CTC AAA GT | 411 | |

After 48 hours of cp-asiRNAs incubation, the level of TLR3 protein expression was determined via western blot. Briefly, the treated HaCaT cells were lysed with Mammalian protein Extraction Buffer (GE Healthcare). 10 μg of the total protein extract were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-TLR3 antibody (Abcam) and anti-γ-tubulin antibody (Bethyl). The membrane was then washed with TBST for 10 minutes three times and was incubated for 1 hour at the room temperature in 5% skim milk with HRP-conjugated secondary antibody (Santa Cruz). The membrane was washed with TBST for 10 minutes and treated with ECL substrate (Thermo scientific). The Target protein bands were then imaged using a Chemidoc instrument (Bio-rad).

Figure 17:
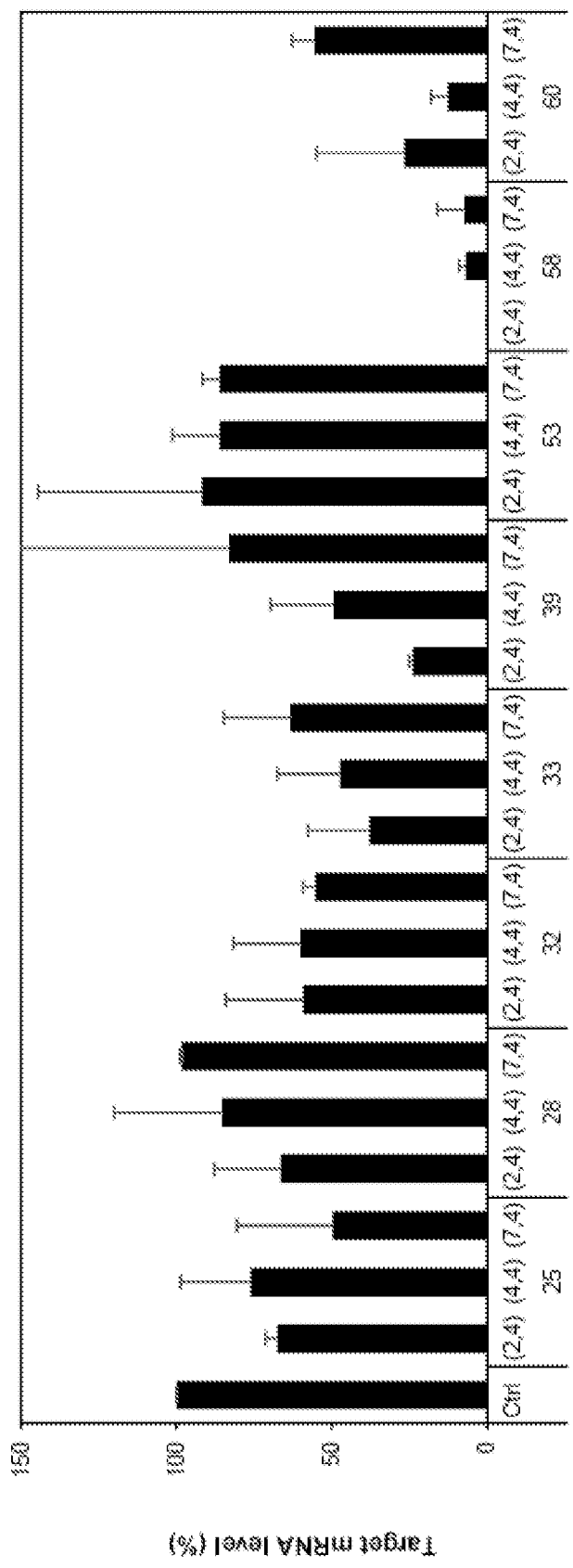
FIG. 17 shows the gene silencing efficiency of exemplary TLR3-targeting cell penetrating asiRNAs (cp-asiRNA, or cp-asiTLR3s) to which various chemical modifications have been applied. The cp-asiRNAs at a concentration of 1 μM were incubated with HaCaT cells and, after 48 hours, the degree of TLR3 mRNA expression was measured using qRT-PCR. The mean and standard deviation of two repeat experiments are depicted.
Figure 18:
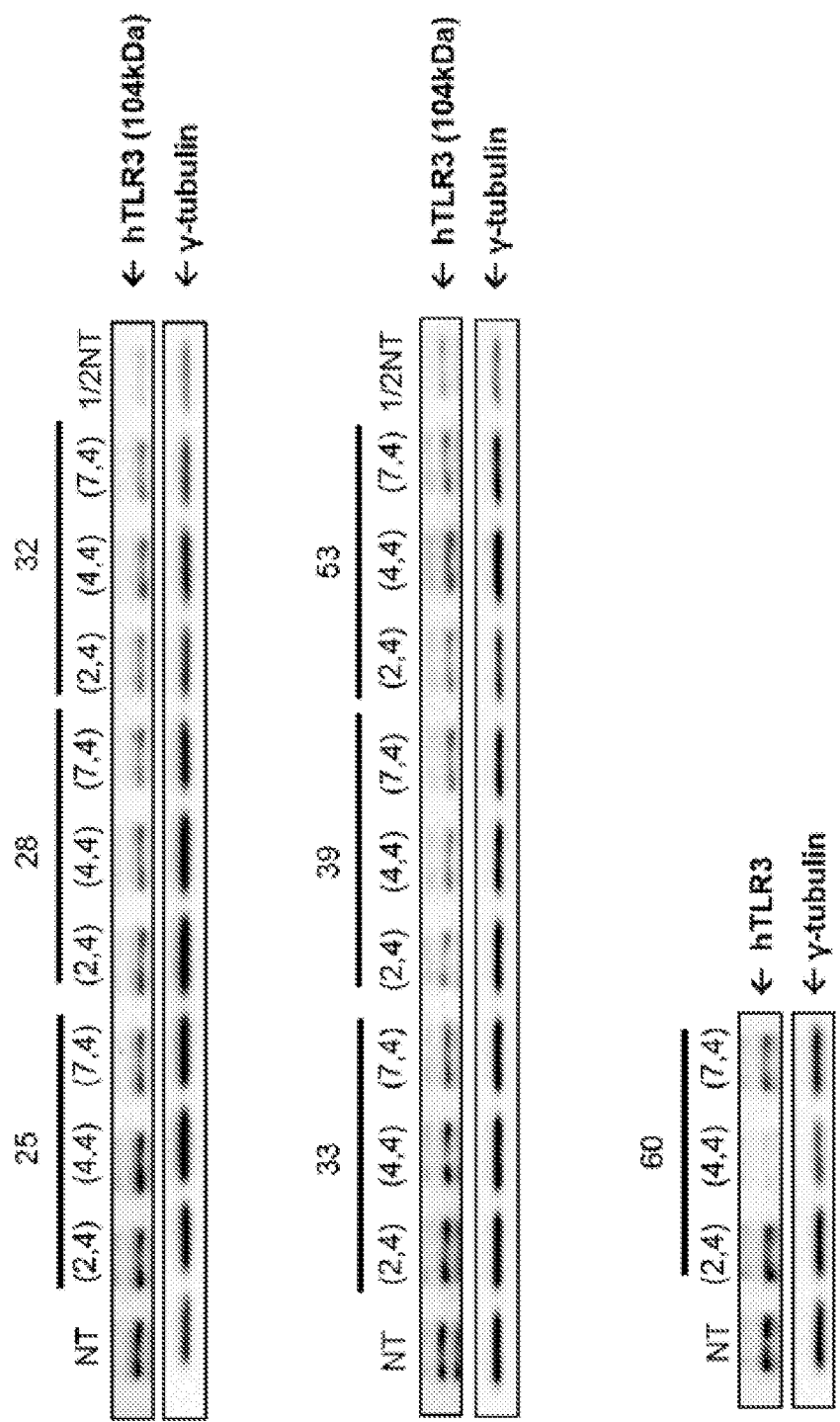
FIG. 18 shows the inhibition of TLR3 protein expression by exemplary cp-asiRNAs. The indicated cp-asiRNAs were contacted to HaCaT cells without transfection vehicle and, after 48 hours, protein was extracted and a western blot performed. (NT=no treatment).

The levels of TLR3 inhibition by each of the 24 potential cp-asiRNAs is provided in FIGS. 17 and 18 From among the potential cp-asiRNAs tested, cp-asiTLR3 39 (2, 4) was selected for further study.

Example 14: Additional TLR3 cp-asiRNA Structures

Other potential cp-asiTLR3 structure having different strand length was synthesized and tested for its ability to inhibit TLR3 expression (Table 10)

TABLE 10

| Name | Additional cp-asiRNA sequences Sequence (5' to 3') | SEQ ID NO: |
|---|---|---|
| TLR3cp-asiRNA S 39 | mGAmAGmAGmGAm-AUmGUmUU*mA*A*cholesterol | 412 |
| TLR3cp-asiRNA AS 39(19) | UUAAACAUUCCUC-UmU*mC*G*C*A | 413 |
| TLR3cp-asiRNA AS 39(2,4) | UUAAACAUUCCUC-UmUmCG*C*A*A*A | 414 |

(m = 2'-O-Methyl RNA.
* = phosphorothioate bond).

The ability of dose dependent of each of the potential cp-asiRNAs listed in Table 10 to inhibit TLR3 expression in HaCaT cells was tested. HaCaT cells were cultured in Dulbecco's modified Eagle's medium (DMEM, Gibco) containing 10% fetal bovine serum (FBS, Gibco) and 100 units/ml Penicillin 100 μg/ml Streptomycin. The potential cp-asiRNAs listed in Table 10 were incubated at 95° C. for 2 minutes and at 37° C. for 1 hour in Opti-MEM (Gibco). Proper strand annealing of the potential cp-asiRNAs was confirmed by gel electrophoresis. On that day cp-asiRNAs treatment, 5×10⁴ cells were seeded 24 well plates then cultured in the presence of the potential cp-asiRNAs in Opti-MEM for 24 hours, at which point the cp-asiRNA-containing Opti-MEM media was replaced with a serum-containing media. Twenty-four hours later, TLR3 expression levels in HaCaT cells were determined.

Figure 19:
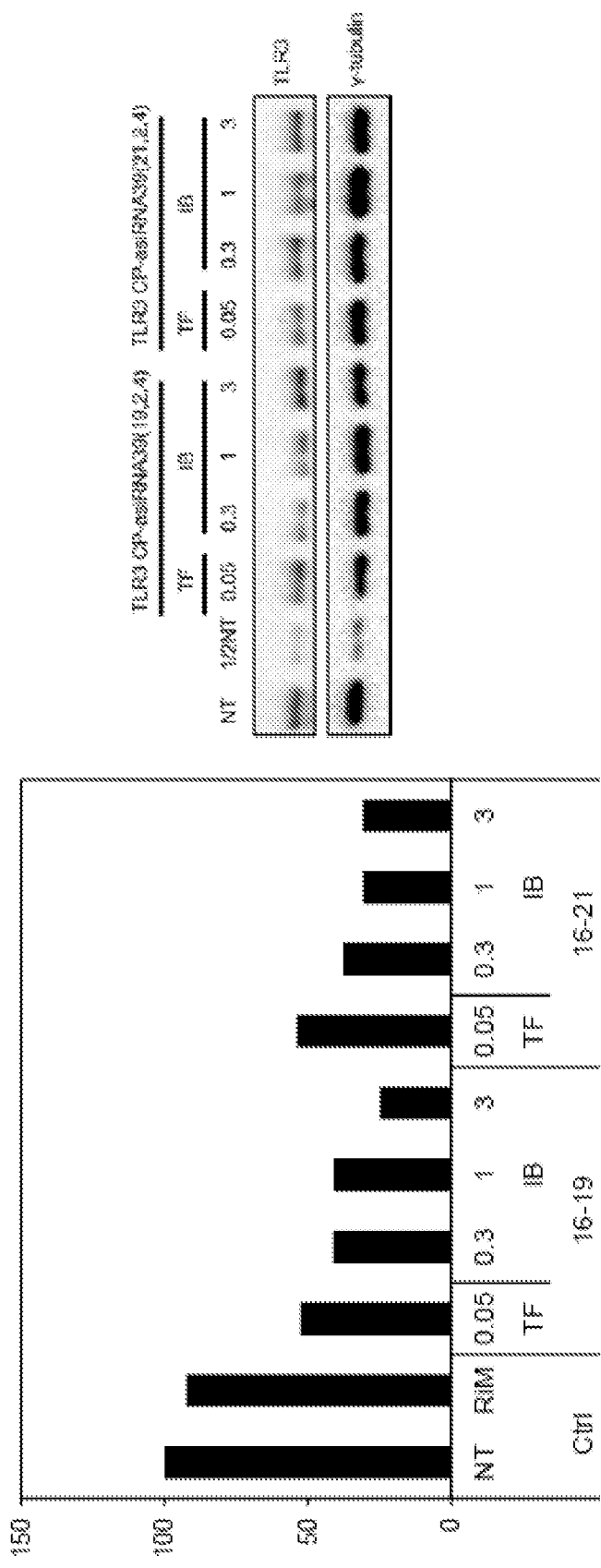
FIG. 19 shows the inhibition of TLR3 mRNA and protein expression by exemplary cp-asiRNAs. The indicated cp-asiRNAs were contacted to HaCaT cells without transfection vehicle and, after 48 hours, the degree of TLR3 expression was determined using qRT-PCR and Western blot.

As seen the FIG. 19, TLR3 expression potential cp-asiRNAs consist of 21 nucleotide antisense strands and potential cp-asiRNAs consist of 19 nucleotide antisense strands exhibited the similar levels of TLR3 inhibition. The cp-asiTLR3 (39) 21 and cp-asiTLR3 (39) 19 were selected for future experimentation.

The efficacy of cp-asiTLR3 (39) 21 and cp-asiTLR3 (39) 19 in low concentration on the production TLR3 protein was tested. The cp-asiRNAs were incubated at 95° C. for 2 minutes and at 37° C. for 1 hour in Opti-MEM (Gibco). Proper strand annealing of the potential cp-asiRNAs was confirmed by gel electrophoresis. HaCaT cells were cultured in Dulbecco's modified Eagle's medium (DMEM, Gibco) containing 10% fetal bovine serum (FBS, Gibco) and 100 units/ml Penicillin and 100 ug/ml Streptomycin. On the day of treatment, 5×10⁴ HaCaT cells were seeded in 12-well plates then cultured in the presence of the potential cp-asiRNAs in Opti-MEM.

Twenty-four hours later, TLR3 protein levels in HaCaT were determined via western blot. Briefly, the treated HaCaT cells were lysed with Mammalian protein Extraction Buffer (GE Healthcare). 10 ug of the total protein extract were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-TLR3 antibody (Abcam) and anti-γ-tubulin antibody (Bethyl). The membrane was then washed with TBST for 10 minutes three times and was incubated for 1 hour at the room temperature in 5% skim milk with HRP-conjugated secondary antibody (Santa Cruz). The membrane was washed with TBST for 10 minutes and treated with ECL substrate (Thermo scientific). The Target protein bands were then imaged using a Chemidoc instrument (Bio-rad).

Figure 20:
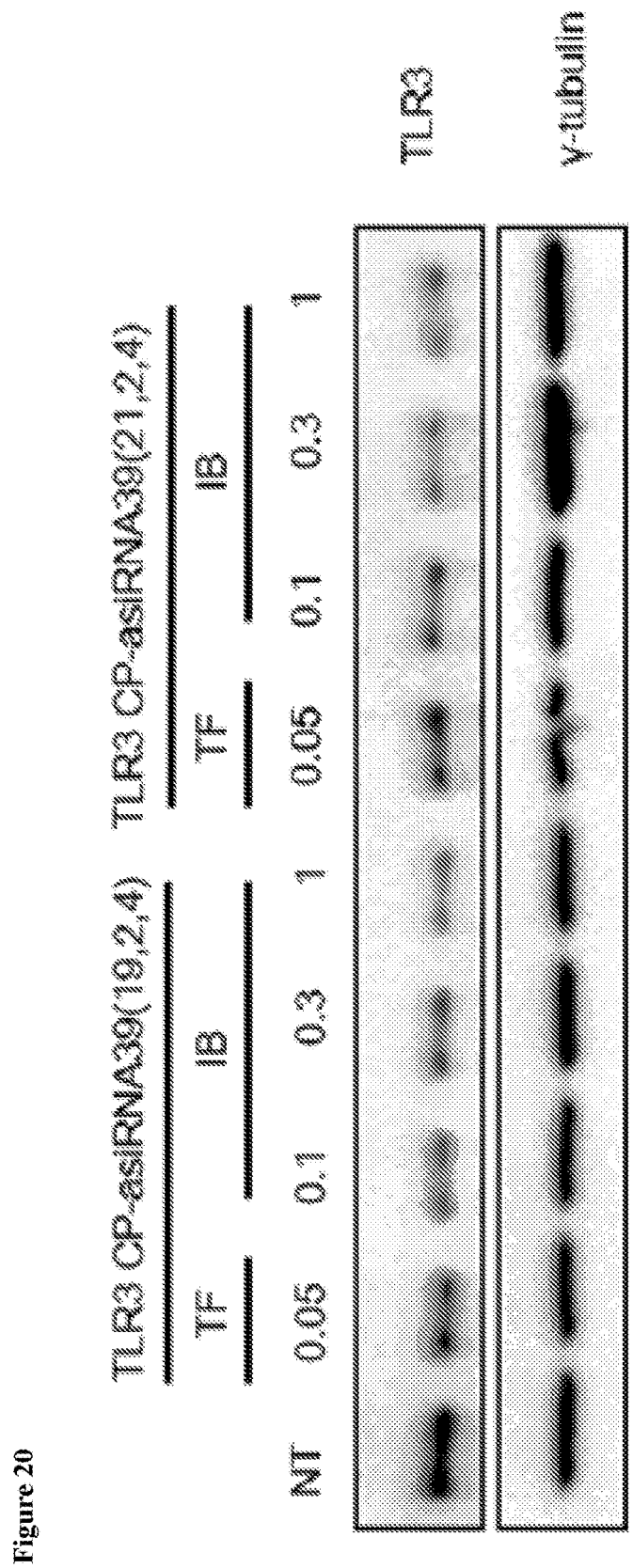
FIG. 20 shows the inhibition of TLR3 protein expression by exemplary cp-asiRNAs. The indicated cp-asiRNAs were contacted to HaCaT cells without transfection vehicle and, after 48 hours, protein was extracted and a western blot performed. (NT=no treatment).

As seen in FIG. 20, TLR3 expression potential cp-asiRNAs having 21 nucleotide antisense strands and potential cp-asiRNAs having 19 nucleotide antisense strands exhibited the similar levels of TLR3 inhibition in low concentration.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating age-related macular degeneration (AMD) in a subject, comprising administering to the subject an RNA duplex of an antisense strand of at least 19 nucleotides (nt) in length and a sense strand of 16 nt in length, wherein:
   the sequence of the antisense strand comprises SEQ ID NO: 54 or SEQ ID NO: 56;
   the sequence of the sense strand is SEQ ID NO: 53 or SEQ ID NO: 55;
   a cholesterol moiety is attached to the 3' end of the sense strand; and
   the antisense strand and the sense strand form a complex in which the 5' end of the antisense strand and the 3' end of the sense strand form a blunt end.

2. The method of claim 1, wherein the antisense strand is 19 to 21 nt in length.

3. The method of claim 1, wherein the antisense strand is 24 to 121 nt in length.

4. The method of claim 1, wherein the RNA duplex is capable of inhibiting MyD88 expression by a cell.

5. The method of claim 1, wherein the RNA duplex is delivered to cells using a delivery vehicle.

6. The method of claim 1, wherein the RNA duplex further comprises a 2'-O-methylated nucleoside and/or a phosphorothioate bond.

7. The method of claim 6, wherein the RNA duplex comprises a 2'-O-methylated nucleoside positioned at the 3' end of the sense strand and/or at the 3' end of the antisense strand.

8. The method of claim 6, wherein the RNA duplex comprises a phosphorothioate bond.

9. The method of claim 1, wherein the RNA duplex is capable of penetrating the cellular membrane of a cell in the absence of a delivery vehicle.

10. The method of claim 1, wherein the sequence of the antisense strand is SEQ ID NO: 54 or SEQ ID NO: 95, and sequence of the sense strand is SEQ ID NO: 53.

11. The method of claim 1, wherein the sequence of the antisense strand is SEQ ID NO: 56 or SEQ ID NO: 98, and the sequence of the sense strand is SEQ ID NO: 55.

12. The method of claim 3, wherein the RNA duplex comprises a 2'-O-methylated nucleoside positioned at the 3' end of the sense strand and/or at the 3' end of the antisense strand.

13. The method of claim 1, wherein the AMD is wet AMD.

14. The method of claim 1, wherein the AMD is dry AMD.

15. The method of claim 1, comprising administering a second agent for treatment of AMD.

16. The method of claim 15, wherein the second agent is an anti-vascular endothelial growth factor (VEGF) therapeutic.

17. The method of claim 1, comprising administering the RNA complex duplex to the eye of the subject.

18. The method of claim 1, wherein the RNA complex duplex is administered by intravitreal injection.

19. The method of claim 1, wherein the RNA duplex is administered as a pharmaceutically acceptable formulation.

* * * * *

SEQUENCE LISTING

```
<160> NUMBER OF SEQ ID NOS: 414

<210> SEQ ID NO 1
<211> LENGTH: 2862
<212> TYPE: DNA
<213> ORGANISM: Homo sapiens

<400> SEQUENCE: 1
agattcctac ttcttacgcc ccccacatca cccgcctcga gacctcaagg gtagaggtgg      60 gcaccccgc ctccgcactt ttgctcgggg ctccagattg tagggcaggg cggcgcttct     120
cggaaagcga aagccggcgg ggcggggcgg gtgccgcagg agaaagagga agcgctggca     180
gacaatgcga cccgaccgcg ctgaggctcc aggaccgccc gccatggctg caggaggtcc     240
cggcgcgggg tctgcggccc cggtctcctc cacatcctcc cttcccctgg ctgctctcaa     300
catgcgagtg cggcgccgcc tgtctctgtt cttgaacgtg cggacacagg tggcggccga     360
ctggaccgcg ctggcggagg agatggactt tgagtacttg gagatccggc aactggagac     420
acaagcggac cccactggca ggctgctgga cgcctggcag ggacgccctg gcgcctctgt     480
aggccgactg ctcgagctgc ttaccaagct gggccgcgac gacgtgctgc tggagctggg     540
acccagcatt gaggaggatt gccaaaagta tatcttgaag cagcagcagg aggaggctga     600 gaagcccttta caggtggccg ctgtagacag cagtgtccca cggacagcag agctggcggg     660
catcaccaca cttgatgacc ccctggggca tatgcctgag cgtttcgatg ccttcatctg     720
ctattgcccc agcgacatcc agtttgtgca ggagatgatc cggcaactgg aacagacaaa     780
ctatcgactg aagttgtgtg tgtctgaccg cgatgtcctg cctggcacct gtgtctggtc     840
tattgctagt gagctcatcg aaaagaggtg ccgccggatg gtggtggttg tctctgatga     900
ttacctgcag agcaaggaat gtgacttcca gaccaaattt gcactcagcc tctctccagg     960
tgcccatcag aagcgactga tccccatcaa gtacaaggca atgaagaaag agttcccag    1020 catcctgagg ttcatcactg tctgcgacta caccaacccc tgcaccaaat cttggttctg    1080
gactcgcctt gccaaggcct tgtccctgcc ctgaagactg ttctgaggcc ctgggtgtgt    1140
gtgtatctgt ctgcctgtcc atgtacttct gccctgcctc ctcctttcgt tgtaggagga    1200
atctgtgctc tacttacctc tcaattcctg gagatgccaa cttcacagac acgtctgcag    1260
cagctggaca tcacatttca tgtcctgcat ggaaccagtg gctgtgagtg gcatgtccac    1320
ttgctggatt atcagccagg acactataga acaggaccag ctgagactaa gaaggaccag    1380
cagagccagc tcagctctga gccattcaca catcttcacc ctcagtttcc tcacttgagg    1440
agtgggatgg ggagaacaga gagtagctgt gtttgaatcc ctgtaggaaa tggtgaagca    1500
tagctctggg tctcctgggg gagaccaggc ttggctgcgg gagagctggc tgttgctgga    1560
ctacatgctg gccactgctg tgaccacgac actgctgggg cagcttcttc cacagtgatg    1620
cctactgatg cttcagtgcc tctgcacacc gcccattcca cttcctcctt ccccacaggg    1680
caggtgggga agcagtttgg cccagcccaa ggagacccca ccttgagcct tatttcctaa    1740
```

```
tgggtccacc tctcatctgc atctttcaca cctcccagct tctgcccaac cttcagcagt   1800
gacaagtccc caagagactc gcctgagcag cttgggctgc ttttcatttc cacctgtcag   1860
gatgcctgtg tcatgctct cagctccacc tggcatgaga agggatcctg gcctctggca    1920
tattcatcaa gtatgagttc tggggatgag tcactgtaat gatgtgagca gggagccttc   1980
ctccctgggc cacctgcaga gagctttccc accaactttg taccttgatt gccttacaaa   2040
gttatttgtt tacaaacagc gaccatataa aagcctcctg ccccaaagct tgtgggcaca   2100
tgggcacata cagactcaca tacagacaca cacatatatg tacagacatg tactctcaca   2160
cacacaggca ccagcataca cacgtttttc taggtacagc tcccaggaac agctaggtgg   2220
gaaagtccca tcactgaggg agcctaacca tgtccctgaa caaaaattgg gcactcatct   2280 attcctttc tcttgtgtcc ctactcattg aaaccaaact ctggaaagga cccaatgtac    2340
cagtatttat acctctaatg aagcacagag agaggaagag agctgcttaa actcacacaa   2400
caatgaactg cagacacagc tgttctctcc ctctctcctt cccagagcaa tttatacttt   2460
accctcaggc tgtcctctgg ggagaaggtg ccatggtctt aggtgtctgt gccccaggac   2520
agaccctagg accctaaatc aatagaaaaa tgcatatctt tgctccactt tcagccaggc   2580
tggagcaagg taccttttct taggatcttg ggagggaatg gatgcccctc tctgcatgat   2640
cttgttgagg catttagctg ccatgcacct gtccccttt aatactgggc attttaaagc    2700
catctcaaga ggcatcttct acatgttttg tacgcattaa aataatttca aagatatctg   2760
agaaaagccg atatttgcca ttcttcctat atcctggaat atatcttgca tcctgagttt   2820
ataataataa ataatattct accttggaaa aaaaaaaaa aa                       2862

<210> SEQ ID NO 2
<211> LENGTH: 3057
<212> TYPE: DNA
<213> ORGANISM: Homo sapiens

<400> SEQUENCE: 2
cactttcgag agtgccgtct atttgccaca cacttccctg atgaaatgtc tggatttgga    60
ctaaagaaaa aaggaaaggc tagcagtcat ccaacagaat catgagacag actttgcctt   120
gtatctactt tggggggggc cttttgccct ttgggatgct gtgtgcatcc tccaccacca   180
agtgcactgt tagccatgaa gttgctgact gcagccacct gaagttgact caggtacccg   240
atgatctacc cacaaacata acagtgttga accttaccca taatcaactc agaagattac   300
cagccgccaa cttcacaagg tatagccagc taactagctt ggatgtagga tttaacacca   360
tctcaaaact ggagccagaa ttgtgccaga aacttcccat gttaaaagtt ttgaacctcc   420
agcacaatga gctatctcaa ctttctgata aaacctttgc cttctgcacg aatttgactg   480
aactccatct catgtccaac tcaatccaga aaattaaaaa taatccctt gtcaagcaga    540 agaatttaat cacattagat ctgtctcata atggcttgtc atctacaaaa ttaggaactc   600
aggttcagct ggaaaatctc caagagcttc tattatcaaa aataaaatt caagcgctaa    660 aaagtgaaga actggatatc tttgccaatt catctttaaa aaaattagag ttgtcatcga   720
atcaaattaa agagttttct ccagggtgtt ttcacgcaat tggaagatta tttggcctct   780
ttctgaacaa tgtccagctg ggtcccagcc ttacagagaa gctatgtttg gaattagcaa   840
acacaagcat tcggaatctg tctctgagta acagccagct gtccaccacc agcaatacaa   900
ctttcttggg actaaagtgg acaaatctca ctatgctcga tctttcctac aacaacttaa   960
```

-continued

```
atgtggttgg taacgattcc tttgcttggc ttccacaact agaatatttc ttcctagagt    1020
ataataatat acagcatttg ttttctcact ctttgcacgg ctttttcaat gtgaggtacc    1080
tgaatttgaa acggtctttt actaaacaaa gtatttccct tgcctcactc cccaagattg    1140 atgattttc ttttcagtgg ctaaaatgtt tggagcacct taacatggaa gataatgata    1200
ttccaggcat aaaaagcaat atgttcacag gattgataaa cctgaaatac ttaagtctat    1260
ccaactcctt tacaagtttg cgaactttga caaatgaaac atttgtatca cttgctcatt    1320
ctcccttaca catactcaac ctaaccaaga ataaaatctc aaaatagag agtgatgctt     1380 tctcttggtt gggccaccta gaagtacttg acctgggcct taatgaaatt gggcaagaac    1440
tcacaggcca ggaatggaga ggtctagaaa atattttcga aatctatctt tcctacaaca    1500
agtacctgca gctgactagg aactcctttg ccttggtccc aagccttcaa cgactgatgc    1560
tccgaagggt ggcccttaaa aatgtggata gctctccttc accattccag cctcttcgta    1620
acttgaccat tctggatcta agcaacaaca acatagccaa cataaatgat gacatgttgg    1680
agggtcttga gaaactagaa attctcgatt tgcagcataa caacttagca cggctctgga    1740
aacacgcaaa ccctggtggt cccatttatt tcctaagggg tctgtctcac ctccacatcc    1800
ttaacttgga gtccaacggc tttgacgaga tcccagttga ggtcttcaag gatttatttg    1860
aactaaagat catcgattta ggattgaata atttaaacac acttccagca tctgtcttta    1920
ataatcaggt gtctctaaag tcattgaacc ttcagaagaa tctcataaca tccgttgaga    1980
agaaggtttt cgggccagct ttcaggaacc tgactgagtt agatatgcgc tttaatccct    2040
ttgattgcac gtgtgaaagt attgcctggt ttgttaattg gattaacgag acccatacca    2100
acatccctga gctgtcaagc cactacctt gcaacactcc acctcactat catgggttcc     2160
cagtgagact ttttgataca tcatcttgca aagacagtgc ccccttttgaa ctctttttca    2220 tgatcaatac cagtatcctg ttgatttta tctttattgt acttctcatc cactttgagg     2280
gctggaggat atcttttttat tggaatgttt cagtacatcg agttcttggt ttcaaagaaa    2340
tagacagaca gacagaacag tttgaatatg cagcatatat aattcatgcc tataaagata    2400
aggattgggt ctgggaacat ttctcttcaa tggaaaagga agaccaatct ctcaaatttt    2460
gtctggaaga aagggacttt gaggcgggtg ttttttgaact agaagcaatt gttaacagca    2520
tcaaaagaag cagaaaaatt attttttgtta taacacacca tctattaaaa gacccattat    2580
gcaaaagatt caaggtacat catgcagttc aacaagctat tgaacaaaat ctggattcca    2640
ttatattggt tttccttgag gagattccag attataaact gaaccatgca ctctgtttgc    2700
gaagaggaat gtttaaatct cactgcatct tgaactggcc agttcagaaa gaacggatag    2760
gtgcctttcg tcataaattg caagtagcac ttggatccaa aaactctgta cattaaattt    2820
atttaaatat tcaattagca aaggagaaac tttctcaatt taaaaagttc tatggcaaat    2880
ttaagttttc cataaaggtg ttataatttg tttattcata tttgtaaatg attatattct    2940
atcacaatta catctcttct aggaaaatgt gtctccttat ttcaggccta tttttgacaa    3000
ttgacttaat tttacccaaa ataaaacata taagcacgta aaaaaaaaaa aaaaaaa      3057
```

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 3
ggcggccgac uggacc                                                    16

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gguccagucg gccgccacc                                                 19

<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uggcggccga cuggac                                                    16

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guccagucgg ccgccaccu                                                 19

<210> SEQ ID NO 7
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
guggcggccg acugga                                                    16

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uccagucggc cgccaccug                                                 19

<210> SEQ ID NO 9
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9

-continued cuggcggagg agaugg                                                  16

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10 ccaucccuc cgccagcgc                                                19

<210> SEQ ID NO 11
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcuggcggag gagaug                                                  16

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
caucuccucc gccagcgcg                                               19

<210> SEQ ID NO 13
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aguacuugga gauccg                                                  16

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cggaucucca aguacucaa                                               19

<210> SEQ ID NO 15
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15

```
gaguacuugg agaucc                                                     16

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaucuccaa guacucaaa                                                  19

<210> SEQ ID NO 17
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gccuuuacag guggcc                                                     16

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggccaccugu aaaggcuuc                                                  19

<210> SEQ ID NO 19
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
agccuuuaca gguggc                                                     16

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gccaccugua aaggcuucu                                                  19

<210> SEQ ID NO 21
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aagccuuuac aggugg                                                     16
```

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ccaccuguaa aggcuucuc                                                19

<210> SEQ ID NO 23
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gaagccuuua caggug                                                   16

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
caccuguaaa ggcuucuca                                                19

<210> SEQ ID NO 25
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agaagccuuu acaggu                                                   16

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
accuguaaag gcuucucag                                                19

<210> SEQ ID NO 27
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
agaugauccg gcaacu                                                   16

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aguugccgga ucaucuccu                                                   19

<210> SEQ ID NO 29
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gagaugaucc ggcaac                                                      16

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
guugccggau caucuccug                                                   19

<210> SEQ ID NO 31
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ggagaugauc cggcaa                                                      16

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uugccggauc aucuccugc                                                   19

<210> SEQ ID NO 33
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aggagaugau ccggca                                                      16

```
<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugccggauca ucuccugca                                                  19

<210> SEQ ID NO 35
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
caggagauga uccggc                                                     16

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gccggaucau cuccugcac                                                  19

<210> SEQ ID NO 37
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gcaggagaug auccgg                                                     16

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccggaucauc uccugcaca                                                  19

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugcaggagau gauccg                                                     16

<210> SEQ ID NO 40
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cggaucaucu ccugcacaa                                                  19

<210> SEQ ID NO 41
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
gugcaggaga ugaucc                                                     16

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggaucaucuc cugcacaaa                                                  19

<210> SEQ ID NO 43
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ugugcaggag augauc                                                     16

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gaucaucucc ugcacaaac                                                  19

<210> SEQ ID NO 45
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uugugcagga gaugau                                                     16

<210> SEQ ID NO 46
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aucaucuccu gcacaaacu                                                   19

<210> SEQ ID NO 47
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuugugcagg agauga                                                      16

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ucaucuccug cacaaacug                                                   19

<210> SEQ ID NO 49
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
guuugugcag gagaug                                                      16

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
caucuccugc acaaacugg                                                   19

<210> SEQ ID NO 51
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aguuugugca ggagau                                                      16

<210> SEQ ID NO 52
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 52
aucuccugca caaacugga                                                   19

<210> SEQ ID NO 53
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gugacuucca gaccaa                                                      16

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uuggucugga agucacauu                                                   19

<210> SEQ ID NO 55
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ugugacuucc agacca                                                      16

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uggucuggaa gucacauuc                                                   19

<210> SEQ ID NO 57
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
augugacuuc cagacc                                                      16

<210> SEQ ID NO 58
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 58
ggucuggaag ucacauucc                                                19

<210> SEQ ID NO 59
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aaugugacuu ccagac                                                   16

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gucuggaagu cacauuccu                                                19

<210> SEQ ID NO 61
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gaaugugacu uccaga                                                   16

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ucuggaaguc acauuccuu                                                19

<210> SEQ ID NO 63
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggaaugugac uuccag                                                   16

<210> SEQ ID NO 64
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 64
cuggaaguca cauuccuug                                              19

<210> SEQ ID NO 65
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
aggaauguga cuucca                                                 16

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uggaagucac auuccuugc                                              19

<210> SEQ ID NO 67
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
aaggaaugug acuucc                                                 16

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ggaagucaca uuccuugcu                                              19

<210> SEQ ID NO 69
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
caaggaaugu gacuuc                                                 16

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 70
gaagucacau uccuugcuc                                                    19

<210> SEQ ID NO 71
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gcaaggaaug ugacuu                                                       16

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
aagucacauu ccuugcucu                                                    19

<210> SEQ ID NO 73
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agcaaggaau gugacu                                                       16

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
agucacauuc cuugcucug                                                    19

<210> SEQ ID NO 75
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gagcaaggaa ugugac                                                       16

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 76
gucacauucc uugcucugc                                              19

<210> SEQ ID NO 77
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agagcaagga auguga                                                 16

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ucacauuccu ugcucugca                                              19

<210> SEQ ID NO 79
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
cagagcaagg aaugug                                                 16

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cacauuccuu gcucugcag                                              19

<210> SEQ ID NO 81
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gucccugccc ugaaga                                                 16

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 82
ucuucagggc agggacaag                                                19

<210> SEQ ID NO 83
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ugucccugcc cugaag                                                   16

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cuucagggca gggacaagg                                                19

<210> SEQ ID NO 85
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uugucccugc ccugaa                                                   16

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uucagggcag ggacaaggc                                                19

<210> SEQ ID NO 87
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gcaccugugu cugguc                                                   16

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
```

```
gaccagacac aggugccag                                                    19
```

<210> SEQ ID NO 89
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89

```
ggcaccugug ucuggu                                                       16
```

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90

```
accagacaca ggugccagg                                                    19
```

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

```
gagtcaacgg atttggtcgt                                                   20
```

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

```
gacaagcttc ccgttctcag                                                   20
```

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
aagttatttg tttacaaaca gcgacca                                           27
```

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggaagaatgg caaatatcgg ct                                          22

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
uuggucugga agucacauuc c                                           21

<210> SEQ ID NO 96
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uuggucugga agucacauuc cuugcucugc a                                31

<210> SEQ ID NO 97
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ugugacuucc agacca                                                 16

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uggucuggaa gucacauucc u                                           21

<210> SEQ ID NO 99
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uggucuggaa gucacauucc uugcucugca g                                31

<210> SEQ ID NO 100
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gugacuucca gaccaa                                                 16

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 101
uuggucugga agucacauu                                              19

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 102
uuggucugga agucacauuc c                                           21

<210> SEQ ID NO 103
<211> LENGTH: 16
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 103
ugugacuucc agacca                                                 16

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 104
uggucuggaa gucacauuc                                              19

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 105
uggucuggaa gucacauucc u                                           21

<210> SEQ ID NO 106
<211> LENGTH: 16
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 106
gugacuucca gaccaa                                                 16

```
<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uuggucugga agucacauuc c                                             21

<210> SEQ ID NO 108
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gugacuucca gaccaa                                                   16

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
uuggucugga agucacauuc c                                             21

<210> SEQ ID NO 110
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gugacuucca gaccaa                                                   16

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uuggucugga agucacauuc c                                             21

<210> SEQ ID NO 112
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gugacuucca gaccaa                                                   16
```

```
<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uuggucugga agucacauuc c                                              21

<210> SEQ ID NO 114
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gugacuucca gaccaa                                                    16

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uuggucugga agucacauuc c                                              21

<210> SEQ ID NO 116
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gugacuucca gaccaa                                                    16

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uuggucugga agucacauuc c                                              21

<210> SEQ ID NO 118
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gugacuucca gaccaa                                                    16

<210> SEQ ID NO 119
```

<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uuggucugga agucacauuc c               21

<210> SEQ ID NO 120
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gugacuucca gaccaa               16

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uuggucugga agucacauuc c               21

<210> SEQ ID NO 122
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gugacuucca gaccaa               16

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uuggucugga agucacauuc c               21

<210> SEQ ID NO 124
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gugacuucca gaccaa               16

<210> SEQ ID NO 125
<211> LENGTH: 21

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
uuggucugga agucacauuc c                                              21

<210> SEQ ID NO 126
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ugugacuucc agacca                                                    16

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uggucuggaa gucacauucc u                                              21

<210> SEQ ID NO 128
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ugugacuucc agacca                                                    16

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uggucuggaa gucacauucc u                                              21

<210> SEQ ID NO 130
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ugugacuucc agacca                                                    16

<210> SEQ ID NO 131
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 131
uggucuggaa gucacauucc u                                              21

<210> SEQ ID NO 132
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ugugacuucc agacca                                                    16

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uggucuggaa gucacauucc u                                              21

<210> SEQ ID NO 134
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ugugacuucc agacca                                                    16

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
uggucuggaa gucacauucc u                                              21

<210> SEQ ID NO 136
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ugugacuucc agacca                                                    16

<210> SEQ ID NO 137
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 137
uggucuggaa gucacauucc u                                              21

<210> SEQ ID NO 138
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ugugacuucc agacca                                                    16

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uggucuggaa gucacauucc u                                              21

<210> SEQ ID NO 140
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ugugacuucc agacca                                                    16

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uggucuggaa gucacauucc u                                              21

<210> SEQ ID NO 142
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ugugacuucc agacca                                                    16

<210> SEQ ID NO 143
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 143
uggucuggaa gucacauucc u                                              21

<210> SEQ ID NO 144
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
ugugacuucc agacca                                                    16

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uggucuggaa gucacauucc u                                              21

<210> SEQ ID NO 146
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gugacuucca gaccaa                                                    16

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uuggucugga agucacauuc c                                              21

<210> SEQ ID NO 148
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gugacuucca gaccaa                                                    16

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 149
uuggucugga agucacauuc c                                              21

<210> SEQ ID NO 150
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gugacuucca gaccaa                                                    16

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uuggucugga agucacauuc c                                              21

<210> SEQ ID NO 152
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gugacuucca gaccaa                                                    16

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uuggucugga agucacauuc c                                              21

<210> SEQ ID NO 154
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gugacuucca gaccaa                                                    16

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide <210> SEQ ID NO 156
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uuggucugga agucacauuc c                                              21

<210> SEQ ID NO 156
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gugacuucca gaccaa                                                    16

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uuggucugga agucacauuc c                                              21

<210> SEQ ID NO 158
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gugacuucca gaccaa                                                    16

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uuggucugga agucacauuc c                                              21

<210> SEQ ID NO 160
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gugacuucca gaccaa                                                    16

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 161
uuggucugga agucacauuc c                                              21

<210> SEQ ID NO 162
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ugugacuucc agacca                                                    16

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uggucuggaa gucacauucc u                                              21

<210> SEQ ID NO 164
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
ugugacuucc agacca                                                    16

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uggucuggaa gucacauucc u                                              21

<210> SEQ ID NO 166
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ugugacuucc agacca                                                    16

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
```
uggucuggaa gucacauucc u                                              21

<210> SEQ ID NO 168
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ugugacuucc agacca                                                    16

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
uggucuggaa gucacauucc u                                              21

<210> SEQ ID NO 170
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gugacuucca gaccaa                                                    16

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uuggucugga agucacauuc c                                              21

<210> SEQ ID NO 172
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gugacuucca gaccaa                                                    16

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
uuggucugga agucacauu         19

<210> SEQ ID NO 174
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ugugacuucc agacca         16

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uggucuggaa gucacauucc u         21

<210> SEQ ID NO 176
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
ugugacuucc agacca         16

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uggucuggaa gucacauuc         19

<210> SEQ ID NO 178
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
aucuuuccua caacaa         16

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
uuguuguagg aaagaucgag c         21

<210> SEQ ID NO 180
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180 ucuuccuac aacaac                                                    16

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
guuguuguag gaaagaucga g                                             21

<210> SEQ ID NO 182
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ggcccuuaaa aaugug                                                   16

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
cacauuuuua agggccaccc u                                             21

<210> SEQ ID NO 184
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gcccuuaaaa augugg                                                   16

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
ccacauuuuu aagggccacc c                                             21

```
<210> SEQ ID NO 186
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
cccuuaaaaa ugugga                                                        16

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uccacauuuu uaagggccac c                                                  21

<210> SEQ ID NO 188
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ccuuaaaaau guggau                                                        16

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
auccacauuu uuaagggcca c                                                  21

<210> SEQ ID NO 190
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
cuuaaaaaug uggaua                                                        16

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
uauccacauu uuuaagggcc a                                                  21
```

<210> SEQ ID NO 192
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
ucguaacuug accauu                                                       16

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
aauggucaag uuacgaagag g                                                 21

<210> SEQ ID NO 194
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
cguaacuuga ccauuc                                                       16

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gaauggucaa guuacgaaga g                                                 21

<210> SEQ ID NO 196
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
guaacuugac cauucu                                                       16

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
agaaugguca aguuacgaag a                                                 21

<210> SEQ ID NO 198

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uaacuugacc auucug                                                       16

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
cagaaugguc aaguuacgaa g                                                 21

<210> SEQ ID NO 200
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
aacuugacca uucugg                                                       16

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ccagaauggu caaguuacga a                                                 21

<210> SEQ ID NO 202
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
acuugaccau ucugga                                                       16

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uccagaaugg ucaaguuacg a                                                 21

<210> SEQ ID NO 204
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
aacaacaaca uagcca                                                          16

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uggcuauguu guuguugcuu a                                                    21

<210> SEQ ID NO 206
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
acaacaacau agccaa                                                          16

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uuggcuaugu uguuguugcu u                                                    21

<210> SEQ ID NO 208
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
caacaacaua gccaac                                                          16

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
guuggcuaug uuguuguugc u                                                    21

<210> SEQ ID NO 210
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 210
aacaacauag ccaaca                                                    16

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
uguuggcuau guuguuguug c                                              21

<210> SEQ ID NO 212
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
acaacauagc caacau                                                    16

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
auguuggcua uguuguuguu g                                              21

<210> SEQ ID NO 214
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
caacauagcc aacaua                                                    16

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uauguuggcu auguuguugu u                                              21

<210> SEQ ID NO 216
<211> LENGTH: 16
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 216
aacauagcca acauaa                                                         16

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uuauguuggc uauguuguug u                                                   21

<210> SEQ ID NO 218
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
acauagccaa cauaaa                                                         16

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uuuauguugg cuauguuguu g                                                   21

<210> SEQ ID NO 220
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
auagccaaca uaaaug                                                         16

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cauuuauguu ggcuauguug u                                                   21

<210> SEQ ID NO 222
<211> LENGTH: 16
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 222
uagccaacau aaauga                                                          16

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ucauuuaugu uggcuauguu g                                                    21

<210> SEQ ID NO 224
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
aaucucucaa auuuug                                                          16

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
caaaauuuga gagauugguc u                                                    21

<210> SEQ ID NO 226
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ugcacucugu uugcga                                                          16

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
ucgcaaacag agugcauggu u                                                    21

<210> SEQ ID NO 228
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 228
gcacucuguu ugcgaa                                              16

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uucgcaaaca gagugcaugg u                                        21

<210> SEQ ID NO 230
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cacucuguuu gcgaag                                              16

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
cuucgcaaac agagugcaug g                                        21

<210> SEQ ID NO 232
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
acucuguuug cgaaga                                              16

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ucuucgcaaa cagagugcau g                                        21

<210> SEQ ID NO 234
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 234
cucuguuugc gaagag						16

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
cucuucgcaa acagagugca u						21

<210> SEQ ID NO 236
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ucuguuugcg aagagg						16

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
ccucuucgca aacagagugc a						21

<210> SEQ ID NO 238
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cuguuugcga agagga						16

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
uccucuucgc aaacagagug c						21

<210> SEQ ID NO 240
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 240
uguuugcgaa gaggaa                                                    16

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
uuccucuucg caaacagagu g                                              21

<210> SEQ ID NO 242
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
guuugcgaag aggaau                                                    16

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
auuccucuuc gcaaacagag u                                              21

<210> SEQ ID NO 244
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uuugcgaaga ggaaug                                                    16

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
cauuccucuu cgcaaacaga g                                              21

<210> SEQ ID NO 246
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
```

```
uugcgaagag gaaugu                                                      16
```

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247

```
acauccucu ucgcaaacag a                                                 21
```

<210> SEQ ID NO 248
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248

```
ugcgaagagg aauguu                                                      16
```

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249

```
aacauuccuc uucgcaaaca g                                                21
```

<210> SEQ ID NO 250
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250

```
gcgaagagga auguuu                                                      16
```

<210> SEQ ID NO 251
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251

```
aaacauuccu cuucgcaaac a                                                21
```

<210> SEQ ID NO 252
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252

```
cgaagaggaa uguuua                                              16

<210> SEQ ID NO 253
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uaaacauucc ucuucgcaaa c                                        21

<210> SEQ ID NO 254
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gaagaggaau guuuaa                                              16

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
uuaaacauuc cucuucgcaa a                                        21

<210> SEQ ID NO 256
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
aagaggaaug uuuaaa                                              16

<210> SEQ ID NO 257
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
uuuaaacauu ccucuucgca a                                        21

<210> SEQ ID NO 258
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
agaggaaugu uuaaau                                              16
```

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
auuuaaacau uccucuucgc a                                          21

<210> SEQ ID NO 260
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
gaggaauguu uaaauc                                                16

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gauuuaaaca uuccucuucg c                                          21

<210> SEQ ID NO 262
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
aggaauguuu aaaucu                                                16

<210> SEQ ID NO 263
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
agauuuaaac auuccucuuc g                                          21

<210> SEQ ID NO 264
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
ggaauguuua aaucuc                                                16

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gagauuuaaa cauuccucuu c                                                21

<210> SEQ ID NO 266
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
cuugaacugg ccaguu                                                      16

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
aacuggccag uucaagaugc a                                                21

<210> SEQ ID NO 268
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
uugaacuggc caguuc                                                      16

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
gaacuggcca guucaagaug c                                                21

<210> SEQ ID NO 270
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ugaacuggcc aguuca                                                      16

```
<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
ugaacuggcc aguucaagau g                                              21

<210> SEQ ID NO 272
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
gaacuggcca guucag                                                    16

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
cugaacuggc caguucaaga u                                              21

<210> SEQ ID NO 274
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
aacuggccag uucaga                                                    16

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ucugaacugg ccaguucaag a                                              21

<210> SEQ ID NO 276
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
acuggccagu ucagaa                                                    16

<210> SEQ ID NO 277
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
uucugaacug gccaguucaa g                                              21

<210> SEQ ID NO 278
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
cuggccaguu cagaaa                                                    16

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
uuucugaacu ggccaguuca a                                              21

<210> SEQ ID NO 280
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uggccaguuc agaaag                                                    16

<210> SEQ ID NO 281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
cuuucugaac uggccaguuc a                                              21

<210> SEQ ID NO 282
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
ggccaguuca gaaaga                                                    16

<210> SEQ ID NO 283
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ucuuucugaa cuggccaguu c                                              21

<210> SEQ ID NO 284
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
gccaguucag aaagaa                                                    16

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
uucuuucuga acuggccagu u                                              21

<210> SEQ ID NO 286
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ccaguucaga aagaac                                                    16

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
guucuuucug aacuggccag u                                              21

<210> SEQ ID NO 288
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
caguucagaa agaacg                                                    16

<210> SEQ ID NO 289
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 289
cguucuuucu gaacuggcca g                                               21

<210> SEQ ID NO 290
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
aguucagaaa gaacgg                                                     16

<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ccguucuuuc ugaacuggcc a                                               21

<210> SEQ ID NO 292
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
guucagaaag aacgga                                                     16

<210> SEQ ID NO 293
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uccguucuuu cugaacuggc c                                               21

<210> SEQ ID NO 294
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
uucagaaaga acggau                                                     16

<210> SEQ ID NO 295
<211> LENGTH: 21
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 295
auccguucuu ucugaacugg c                                             21

<210> SEQ ID NO 296
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
ucagaaagaa cggaua                                                   16

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
uauccguucu uucugaacug g                                             21

<210> SEQ ID NO 298
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
aauugcaagu agcacu                                                   16

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
agugcuacuu gcaauuuaug a                                             21

<210> SEQ ID NO 300
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
auugcaagua gcacuu                                                   16

<210> SEQ ID NO 301
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 301
aagugcuacu ugcaauuuau g                                              21

<210> SEQ ID NO 302
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
uugcaaguag cacuug                                                    16

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
caagugcuac uugcaauuua u                                              21

<210> SEQ ID NO 304
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ugcaaguagc acuugg                                                    16

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
ccaagugcua cuugcaauuu a                                              21

<210> SEQ ID NO 306
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gcaaguagca cuugga                                                    16

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 307
uccaagugcu acuugcaauu u                                              21

<210> SEQ ID NO 308
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
caaguagcac uuggau                                                    16

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
auccaagugc uacuugcaau u                                              21

<210> SEQ ID NO 310
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
aaguagcacu uggauc                                                    16

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gauccaagug cuacuugcaa u                                              21

<210> SEQ ID NO 312
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
ugcccccuuu gaacuc                                                    16

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 313
gaguucaaag ggggcacugu c            21

<210> SEQ ID NO 314
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ucugggaaca uuucuc            16

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
gagaaauguu cccagaccca a            21

<210> SEQ ID NO 316
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
cagcaucaaa agaagc            16

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
gcuucuuuug augcuguuaa c            21

<210> SEQ ID NO 318
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
cacgugugaa aguauu            16

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 319
aauacuuuca cacgugcaau c                                          21

<210> SEQ ID NO 320
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
gucucaccuc cacauc                                                16

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
gauguggagg ugagacagac c                                          21

<210> SEQ ID NO 322
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
ugucucaccu ccacau                                                16

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
auguggaggu gagacagacc c                                          21

<210> SEQ ID NO 324
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
agauucaagg uacauc                                                16

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
```

-continued gauguaccuu gaaucuuuug c                                       21

<210> SEQ ID NO 326
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
ggaaacacgc aaaccc                                             16

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
ggguuugcgu guuccagag c                                        21

<210> SEQ ID NO 328
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
uggaaacacg caaacc                                             16

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
gguuugcgug uuccagagc c                                        21

<210> SEQ ID NO 330
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uugagaaacu agaaau                                             16

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
auuucuaguu ucucaagacc c   21

<210> SEQ ID NO 332
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
cuugagaaac uagaaa   16

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
uuucuaguuu cucaagaccc u   21

<210> SEQ ID NO 334
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
aacauccguu gagaag   16

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
cuucucaacg gauguuauga g   21

<210> SEQ ID NO 336
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336 gugccccuu ugaacu   16

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
aguucaaagg gggcacuguc u   21

<210> SEQ ID NO 338
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338 agugccccu uugaac                                                      16

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
guucaaaggg ggcacugucu u                                               21

<210> SEQ ID NO 340
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
cagugccccc uuugaa                                                     16

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
uucaaagggg gcacugucuu u                                               21

<210> SEQ ID NO 342
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
ggaggauauc uuuuua                                                     16

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
uaaaaagaua uccuccagcc c                                               21

```
<210> SEQ ID NO 344
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
uggaggauau cuuuuu                                                       16

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
aaaaagauau ccuccagccc u                                                 21

<210> SEQ ID NO 346
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
acugaaccau gcacuc                                                       16

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
gagugcaugg uucaguuuau a                                                 21

<210> SEQ ID NO 348
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
ugaaccaugc acucug                                                       16

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
cagagugcau gguucaguuu a                                                 21
```

```
<210> SEQ ID NO 350
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
gaaccaugca cucugu                                                        16

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
acagagugca ugguucaguu u                                                  21

<210> SEQ ID NO 352
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aaccaugcac ucuguu                                                        16

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
aacagagugc augguucagu u                                                  21

<210> SEQ ID NO 354
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
accaugcacu cuguuu                                                        16

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
aaacagagug caugguucag u                                                  21

<210> SEQ ID NO 356
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
ccaugcacuc uguuug                                                         16

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
caaacagagu gcaugguuca g                                                   21

<210> SEQ ID NO 358
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
caugcacucu guuugc                                                         16

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
gcaaacagag ugcaugguuc a                                                   21

<210> SEQ ID NO 360
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
cugcaucuug aacugg                                                         16

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
ccaguucaag augcagugag a                                                   21

<210> SEQ ID NO 362
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
acugcaucuu gaacug                                                    16

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
caguucaaga ugcagugaga u                                              21

<210> SEQ ID NO 364
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
cacugcaucu ugaacu                                                    16

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
aguucaagau gcagugagau u                                              21

<210> SEQ ID NO 366
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
ucacugcauc uugaac                                                    16

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
guucaagaug cagugagauu u                                              21

<210> SEQ ID NO 368
<211> LENGTH: 16
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 368
uaaauugcaa guagca                                                       16

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
ugcuacuugc aauuuaugac g                                                 21

<210> SEQ ID NO 370
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
auaaauugca aguagc                                                       16

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
gcuacuugca auuuaugacg a                                                 21

<210> SEQ ID NO 372
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
cgucauaaau ugcaag                                                       16

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
cuugcaauuu augacgaaag g                                                 21

<210> SEQ ID NO 374
<211> LENGTH: 16
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 374
ucgucauaaa uugcaa                                                          16

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
uugcaauuua ugacgaaagg c                                                    21

<210> SEQ ID NO 376
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uucgucauaa auugca                                                          16

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
ugcaauuuau gacgaaaggc a                                                    21

<210> SEQ ID NO 378
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
ugcacucugu uugcga                                                          16

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ucgcaaacag agugcauggu u                                                    21

<210> SEQ ID NO 380
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 380
ucgcaaacag agugcauggu u                                              21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
ucgcaaacag agugcauggu u                                              21

<210> SEQ ID NO 382
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
acucuguuug cgaaga                                                    16

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ucuucgcaaa cagagugcau g                                              21

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
ucuucgcaaa cagagugcau g                                              21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
ucuucgcaaa cagagugcau g                                              21

<210> SEQ ID NO 386
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 386
uguuugcgaa gaggaa                                                    16

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
uuccucuucg caaacagagu g                                              21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
uuccucuucg caaacagagu g                                              21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
uuccucuucg caaacagagu g                                              21

<210> SEQ ID NO 390
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
guuugcgaag aggaau                                                    16

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391 auccucuuc gcaaacagag u                                               21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 392 auccucuuc gcaaacagag u                                              21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393 auccucuuc gcaaacagag u                                              21

<210> SEQ ID NO 394
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
gaagaggaau guuuaa                                                   16

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
uuaaacauuc cucuucgcaa a                                             21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
uuaaacauuc cucuucgcaa a                                             21

<210> SEQ ID NO 397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uuaaacauuc cucuucgcaa a                                             21

<210> SEQ ID NO 398
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 398
ggccaguuca gaaaga                                                    16

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
ucuuucugaa cuggccaguu c                                              21

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ucuuucugaa cuggccaguu c                                              21

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
ucuuucugaa cuggccaguu c                                              21

<210> SEQ ID NO 402
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
guucagaaag aacgga                                                    16

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
uccguucuuu cugaacuggc c                                              21

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
```
uccguucuuu cugaacuggc c         21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
uccguucuuu cugaacuggc c         21

<210> SEQ ID NO 406
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ucagaaagaa cggaua         16

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
uauccguucu uucugaacug g         21

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
uauccguucu uucugaacug g         21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
uauccguucu uucugaacug g         21

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410

```
tgccccttt gaactctttt                                                    20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
aaaaacaccc gcctcaaagt                                                   20

<210> SEQ ID NO 412
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
gaagaggaau guuuaa                                                       16

<210> SEQ ID NO 413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uuaaacauuc cucuucgca                                                    19

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uuaaacauuc cucuucgcaa a                                                 21
```